(12) United States Patent
LaPointe et al.

(10) Patent No.: US 10,344,334 B2
(45) Date of Patent: Jul. 9, 2019

(54) METHOD OF DIAGNOSING NEOPLASMS

(71) Applicants: CLINICAL GENOMICS PTY. LTD., North Ryde, New South Wales (AU); COMMONWEALTH SCIENTIFIC AND INDUSTRIAL RESEARCH ORGANISATION, Campbell, Australian Capital Territory (AU)

(72) Inventors: Lawrence Charles LaPointe, West Pennant Hills (AU); Robert Dunne, Darlington (AU); Graeme P. Young, Malvern (AU); Peter Molloy, Chatswood (AU); Susanne Pedersen, North Ryde (AU); Glenn Southwell Brown, Epping (AU); Lloyd Douglas Graham, North Epping (AU)

(73) Assignees: CLINICAL GENOMICS PTY. LTD., North Ryde (AU); COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 0 days.

(21) Appl. No.: 14/824,522

(22) Filed: Aug. 12, 2015

(65) Prior Publication Data
US 2016/0130657 A1 May 12, 2016

Related U.S. Application Data

(62) Division of application No. 12/739,559, filed as application No. PCT/AU2008/001569 on Oct. 23, 2008, now abandoned.

(60) Provisional application No. 60/982,114, filed on Oct. 23, 2007.

(51) Int. Cl.
| | | |
|---|---|---|
| C12Q 1/68 | (2018.01) | |
| C12Q 1/6886 | (2018.01) | |
| G01N 33/574 | (2006.01) | |

(52) U.S. Cl.
CPC ..... *C12Q 1/6886* (2013.01); *G01N 33/57446* (2013.01); *C12Q 2600/112* (2013.01); *C12Q 2600/158* (2013.01); *C12Q 2600/16* (2013.01); *G01N 2800/06* (2013.01)

(58) Field of Classification Search
None
See application file for complete search history.

(56) References Cited

U.S. PATENT DOCUMENTS

| | | |
|---|---|---|
| 5,045,453 A | 9/1991 | Katopodis |
| 2007/0141066 A1 | 6/2007 | Phillips et al. |
| 2011/0160072 A1 | 6/2011 | LaPointe et al. |

FOREIGN PATENT DOCUMENTS

| | | |
|---|---|---|
| WO | WO 03/039443 A2 | 5/2003 |
| WO | WO 2006/048291 A2 | 5/2006 |
| WO | WO 2008/021290 A2 | 2/2008 |

OTHER PUBLICATIONS

Alon U. et al., "Broad Patterns of Gene Expression Revealed by Clustering Analysis of Tumor and Normal Colon Tissues Probed by Oligonucleotide Arrays", Proc. Natl. Acad. Sci. USA 96:6745-6750 (Jun. 1999).
Ausubel F. et al., "Current Protocols in Molecular Biology", Suppl. 56 (2001), Suppl. 37 (1997), Suppl. 32 (1995), Suppl. 26 (1994), Suppl. 20 (1992), Suppl. 17 (1992).
Bonner T.I. et al., "Reduction in the Rate of DNA Reassociation by Sequence Divergence", J. Mol. Biol. 81:123-135 (1973).
Derisi J. et al., "Use of a cDNA Microarray to Analyse Gene Expression Patterns in Human Cancer", Nature Genetics 14:457-460 (Dec. 1996).
Germer S. et al., "High-Throughput SNP Allele-Frequency Determination in Pooled DNA Samples by Kinetic PCR", Genome Research 10:258-266 (2000).
Guo Z. et al., "Direct Fluorescence Analysis of Genetic Polymorphisms by Hybridization with Oligonucleotide Arrays on Glass Supports", Nucleic Acids Research 22(24):5456-5465 (1994).
Heid C. A. et al., "Real Time Quantitative PCR", Genome Research 6:986-994 (1996).
Hubbell E. et al., "Robust Estimators for Expression Analysis", Bioinformatics 18(12):1585-1592 (2002).
Irizarry R. A. et al., "Summaries of Affymetrix GeneChip Probe Level Data", Nucleic Acids Research 31(4e15):1-8 (2003).
Kraus M. H. et al., "Detection and Isolation of Novel Protein-Tyrosine Kinase Genes Employing Reduced Stringency Hybridization", Methods in Enzymology 200:546-556 (1991).

(Continued)

*Primary Examiner* — Antonio Galisteo Gonzalez
(74) *Attorney, Agent, or Firm* — Scully Scott Murphy & Presser

(57) ABSTRACT

Disclosed are nucleic acid, RNA, and protein expression profiles which are indicative of the onset, predisposition to the onset and/or progression of a large intestine neoplasm. More particularly disclosed are nucleic acid molecules, the expression profiles of which are indicative of the onset and/or progression of a colorectal neoplasm, such as an adenoma or an adenocarcinoma. The expression profiles of the present invention are useful in a range of applications including, but not limited to, those relating to the diagnosis and/or monitoring of colorectal neoplasms, such as colorectal adenomas and adenocarcinomas. Further disclosed are methods of screening a subject for the onset, predisposition to the onset and/or progression of a large intestine neoplasm by screening for modulation in the expression profile of the disclosed nucleic acid molecule markers.

13 Claims, 29 Drawing Sheets

Specification includes a Sequence Listing.

(56) References Cited

OTHER PUBLICATIONS

Maskos U. et al., "Oligonucleotide Hybridisations on Glass Supports: a Novel Linker for Oligonucleotide Synthesis and Hybridisation Properties of Oligonucleotides Synthesized In Situ", Nucleic Acids Research 20(7):1679-1684 (1992).
Moore A. et al., "Measuring Ttransferrin Receptor Gene Expression by NMR Imaging", Biochimica et Biophysica Acta 1402:239-249 (1998).
Nielsen P.E., "Applications of Peptide Nucleic Acids", Current Opinion in Biotechnology 10:71-75 (1999).
Nielsen P.E. et al., "Sequence-Selective Recognition of DNA by Strand Displacement with a Thymine-Substituted Polyamide", Science 254(5037):1497-1500 (Dec. 6, 1991).
Pease A.C. et al., "Light-Generated Oligonucleotide Arrays for Rapid DNA Sequence Analysis", Proc. Natl. Acad. Sci. USA 91:5022-5026 (May 1994).
Pevzner P.A. et al., "Improved Chips for Sequencing by Hybridization", Journal of Biomolecular Structure & Dynamics 9(2):399-410 (1991).
Porte, H. et al., "Neoplastic Progression of Human Colorectal Cancer is Associated with Overexpression of the Stromelysin-3 and BM-40/SPARC Genes" International Journal of Cancer, 64(1):70-75 (Feb. 20, 1995).
Sano T. et al., "A Streptavidin-Protein A Chimera That Allows One-Step Production of a Variety of Specific Antibody Conjugates", Biotechnology 9:1378-1381 (Dec. 1991).
Schena M. et al., "Quantitative Monitoring of Gene Expression Patterns with a Complementary DNA Microarray", Science 270(5235):467-470 (Oct. 20, 1995).
Smith S.B. et al., "Direct Mechanical Measurements of the Elasticity of Single DNA Molecules by Using Magnetic Beads", Science 258:1122-1126 (Nov. 13, 1992).
Smyth G.K., "Limma: Linear Models for Microarray Data", Bioinformatics and Computational Biology Solutions using R and Bioconductor, pp. 397-420 (2005).
Smyth G.K., "Linear Models and Empirical Bayes Methods for Assessing Differential Expression in Microarray Experiments", Statistical Applications in Genetics and Molecular Biology 3(1):27 pages (2004).
Sundberg S.A. et al., "Microchip-Based Systems for Target Validation and HTS", Drug Discovery Today 5(12) (Suppl.):S92-S103 (Jan. 1, 2000).
Urdea M.S. et al., "Branched DNA Amplification Multimers for the Sensitive, Direct Detection of Human Hepatitis Viruses", Nucleic Acids Research, Symposium Service No. 24:197-200 (1991).
Wedemeyer N. et al., "Flow Cytometric Quantification of Competitive Reverse Transcription-PCR Products", Clinical Chemistry 48(9):1398-1405 (2002).
Weissleder R. et al., "In vivo Magnetic Resonance Imaging of Transgene Expression", Nature Medicine 6(3):351-354 (Mar. 2000).
"Details for HG-U95E: 87972_S_AT" Internet Citation (Jan. 1, 2000) pp. 1-2, XP007915510, https://www.affysetrix.com/analysis/netaffx/fullrecord.affx?pk=HG-U.
Human Genome U133 Array; Affimextrix GeneChip Human Genome Arrays; pp. 1-4 (2004).
Supplementary European Search Report dated Dec. 2, 2010 issued in corresponding European Application No. EP 08 84 3297.6.
International Search Report dated Dec. 22, 2008 issued in corresponding International Application No. PCT/AU2008/001569.
Gardina P.J. et al., "Alternative Splicing and Differential Gene Expression in Colon Cancer Detected by a Whole Genome Exon Array", BMC Genomics 7(1):325 (pp. 1-18) (Dec. 27, 2006).
Huang R.S. et al., "A Genome-Wide Approach to Identify Genetic Variants that Contribute to Etoposide-Induced Cytotoxicity", PNAS 104(23):9758-97963 (Jun. 5, 2007).
Yoshida R. et al., "A Statistical Framework for Genome-Wide Discovery of Biomarker Splice Variations with GeneChip Human Exon 1.0 ST Arrays", Genome-Wide Discovery of Biomarker Splice Variations 17(1):88-99 (Jan. 1, 2006).
"Shows that the Affymetrix Array Human Exon 1.0 Comprises Probe for SEQ ID No. 21-31 of EP 08 843297", Publication taken from paper XP055036877 in which this array was used (Jun. 5, 2007), XP55036885.
"Shows that the Affymetrix Array Human Exon 1.0 Comprises Probe for SEQ ID No. 2-20 of EP 08 843297", Publication taken from paper XP055036877 in which this array was used (Jun. 5, 2007), XP55036893.
European Examination Report dated Sep. 13, 2012 received from Application No. 08 843 297.6.

LOCATION OF AFFYMETRIX TRANSCRIPT CLUSTERS IN hCG_1815491

FIGURE 22

SEQ ID NO:1

*\*\*\*NOTE: Specification of chromosomal map regions refers to coordinates on human chromosome 16 using NCBI entry ID NT_010498.15 /Hs16_10655 in the NCBI 36 March 2006 genome\*\*\**

(Grey shading: Exon sequences – See Appendix B for further information)

[Illegible nucleotide sequence text]

FIGURE 23 hCG_1815491 exon sequences

*\*\*\*NOTE: Specification of chromosomal map regions refers to coordinates on the (+) strand of human chromosome 16 as specified by the NCBI entry ID NT_010498.15 /Hs16_10655 in the NCBI 36 March 2006 genome. The nucleotide sequences listed below correspond to the sense strand of hCG_1815491 \*\*\**

SEQ ID NO:2 (exon segment E1), 184 nucleotides, genomic map region 8577597-8577414

```
atgtactttatttcgcgatctcacactaacccagcgcgcacggcaccgctcggtgctgcgctctcgtgca
cgcgcgttggctcctccctccgtctgctccctcccccagacaccgccaccaagaggcctgagcggttcag
actacattctccgagagccctgggtccgcccagccca
```

SEQ ID NO:3 (exon segment E2), 724 nucleotides, genomic map region 8577328 - 8576605

```
tctcggcgccagagggggcggggaggggcggggtctcgatcgcgctattgtcatggagacgggaagctggctgc
agcggcggcggggaccgtggggccgaggtggctgccagccggccaatgtctaagcgaggcggagcggccagg
cggccgagcctgggggagcgcgcagccggccagtggcggcctcgccggcggctcttccggctcgcagta
ggccgagtcgtcgccggagctcctgggagcagcgtcccgccctgctccctcgctccgcctcttgcggc
ccacggccctcagcgccgccccggctccgccgcgcagccgcagccctggcgctaacggtcggtaac
ggccgcgcgcgccgccgcggggctcgcgcagccacgagggagcgtccgcggccgcgcgccgcgcgg
cggaggagaggtgagccccgccgggcaggcctctggcgcgcgcgtccgccctctagtcgtgtccctc
gtgggcgaacggacgcggcggtgccccgcgccgaccagacgtcccgtgggctagggcctgggcctcgggcc
ggtcggcgccggtcgagcctctccgggtgtcggggttcggggcgggcgcgcgtgggcgtggctcctctgtcc
acgctgttccttcgtcgcgcgggctctcgtccgggacacggctttccggagtagagccttggag
```

SEQ ID NO:4 (exon segment E2a), 448 nucleotides, genomic map region 8577328 - 8576881

```
tctcggcgccagagggggcggggaggggcggggtctcgatcgcgctattgtcatggagacgggaagctggctgc
agcggcggcggggaccgtggggccgaggtggctgccagccggccaatgtctaagcgaggcggagcggccagg
cggccgagcctgggggagcgcgcagccggccagtggcggcctcgccggcggctcttccggctcgcagta
ggccgagtcgtcgccggagctcctgggagcagcgtcccgccctgctccctcgctccgcctcttgcggc
ccacggccctcagcgccgccccggctccgccgcgcagccgcagccctggcgctaacggtcggtaac
ggccgcgcgcgccgccgcggggctcgcgcagccacgagggagcgtccgcggccgcgcgccgcgcgg
cggaggagag
```

SEQ ID NO:5 (exon segment E2b), 274 nucleotides, genomic map region 8576878 - 8576605
```
gagccccgccgggccaggccctctggcgcgcgccgtccgccctctagtcgtgtccctcgtgggcgaacg
gacgcggcggtgccccgcgccgaccagacgtcccgtgggctagggcctgggcctcggcgcgtcggcgcg
gtcgagcctctccgggtgtcggggttcggggcgggcgcgcgtgggcgtggctcctctgtccacgctgttccc
ttcgtcgccgcggctctcgtccgggacacggctttccggagtagagccttggag
```

SEQ ID NO:6 (exon segment E3), 113 nucleotides, genomic map region 8573324 - 8573212
```
Gtgttaagtgtgatgcttccataatacatttggatgctgtcagctaagttcacttctgaactaagggttc
ctccaaatgttggctgaaattcatccaaggctggtctgcaa
```

FIGURE 23 (cont'd)

SEQ ID NO:7 (exon segment E3a), 284 nucleotides, genomic map region 8573324-8573041
gtgttaagtgtgatgcttccataatacatttggatgctgtcagctaagttcacttctgaactaagggttcct
ccaaatgttggctgaaattcatcccaaggctggtctgcaagtgagtgtctgcacacagtttgcttgtatgtgg
agtcgatccaaaatagcatcaatgttggttttaccaaagtatttattattgataatagaggctaagtacaaaa
tgtagagaatgtcagctacttgaggcctttgattattaaaaattttattaatgcattaaacaaga

SEQ ID NO:8 (exon segment E4), 87 nucleotides, genomic map region 8572798 - 8572712
ttacctatttcttttaagaataaatttagtgggaatatcagttccagtcatgggtaccaaacttttttagtga
cagagtacacacag

SEQ ID NO:9 (exon segment E5), 370 nucleotides, genomic map region 8571761 - 8571392
Agtctgcaattcataatggagctactgtactggctattggaaggaggagattctgaagataaggaggtaatat
tatctcttttaaaagaatactttcctctgtaatcctgaatctttattacatgtaagaactttgtgcagtagac
agcaatttctttgaatttggtatatggaaacaattttattttcctctgctaagttttgagcctgcctcttct
agtgccatggactgcattggtagagctgagaaatatcatttagccatactcagcaccttaaaatagcttctt
tctgagaattagatctgtgaaggtgtcctgcacagttcttgtagatgtcatttagtttgtggttgacgtgca
tgcat

SEQ ID NO:10 (exon segment E5a), 66 nucleotides, genomic map region 8571761 - 8571696
agtctgcaattcataatggagctactgtactggctattggaaggaggagattctgaagataaggag

SEQ ID NO:11 (exon segment E5b), 194 nucleotides, genomic map region 8571889 - 8571696
catgcttttgagaagtgtatcatctaggaagaaaatcaaatggagtattggtaattaaattgtaattccatg
aaggaaggaagtggtgcaaaagatgaagctaactattctgttttctttttaagagtctgcaattcataatg
gagctactgtactggctattggaaggaggagattctgaagataaggag

SEQ ID NO:12 (exon segment E6), 113 nucleotides, genomic map region 8568521-8568409
gtaaaacctgtttagaaattaaaaatgagttacgatttaaagaaaattcagatgactcattgtgagtgctagt
tctcttgtaggatgccactggaaatgttgaaatgaaaaat

SEQ ID NO:13 (exon segment E6a), 30 nucleotides, genomic map region 8568438 - 8568409
gatgccactggaaatgttgaaatgaaaaat

SEQ ID NO:14 (exon segment E6c), 41 nucleotides, genomic map region 8568449-8568409
ttctcttgtaggatgccactggaaatgttgaaatgaaaaat

FIGURE 23 (cont'd)

SEQ ID NO:15 (exon segment E6d), 1750 nucleotides, genomic map region 8570158 - 8568409

```
tttaatagaaggaaaatataaatttaatatctgggcaattgagacctttaaacttactttaaaagtatgatct
tgatgtatatgatactgttttgtctttgctatattaacagaattagagggtgttctgcaattcaaatacctt
atatattccaaattttattctctataatggactttttaaaataaaaggtatatgtgcttcaagagggcaaatt
tgaatcatgagctaatttgctaagcatcagattatagaaaagcatccttgattaatttggaactgtgaaggg
ggcgggtaaaactgttttctgcagaaatttactagtgcagcaaccatttaaattaaatgtttgttaacataat
agtgatggcattttctcctcccctccttgtggttttgtccaactagatgttacagtggcagttgcactgact
gttaagtgtttaaatgatgacaccattatgtgaagtgattttgaaatgagagattccagccaagaattacatc
tgctcccatctccttcaaatcatactctctggcagtacagattatgattgatttgtttgtgacagattgcagg
aaacagtcattgattttcaatatttaccttaaaattatttacagttgtaaccatggggaggtattttcatg
ggctgtcagccctgaaagactaggataatattccctgctctctgacaagacaaattacctgtaatgagtgca
gtagctgaagggtatacttttattttaaaatatgtcaataaccccagtgactaaacgaatattgatttagcat
aatgaagcctgagtaacgtgaaaatgagcttttcaaggggcatggtaaagtcttttctttttagctggttgta
agaagcttttgattcttttcagccagctggtaggaatatagaattttataagcaaaccatcaggaatgatagt
gttgtttctgataagcaacatccaaatattttgaccctgcttttagtggtttttttcaaatcttattttgagt
cttactttttagtcatagaatagctactgatttgatgcggtcttttaactgacttaatattttttacaattcaat
atattttgcattggaatctccagtaatgaatattaaaatatatgtacaatcatttgtagatgatatcaattat
attaagacatttcagatgggctattgtagtatttaatgtgccgtatttttatggtagaataattctcagtctct
ggacatcaagattgctttcagtgggaatgaagattaattttacttcagtcctgattttttaggcatcaatgcat
gttttcatttttgtcagacttttaccctcttttaatgtaattctcaacttcttatggatttacttcccaatac
ataaaatccttcaaaacaagaatgataataattttttatacttttttataaaaataaatttattttttagtccatc
aaggtgtctgaagattttatgcctaggtatctccatatctaacttgataaggaaaataggataaacaatgctg
gtaatagcaggaaagtaagtatttgaataagatgtcaaactgatatttcatgtgaacctaactcattttatgg
taactaataattatcttatttaaatcaat aggtaaaacctgtttagaaattaaaaatgagttacgatttaaag
aaaattcagatgactcattgtgagtgct agttctcttgt aggatgccactggaaatgttgaaatgaaaaat
```

SEQ ID NO:16 (exon segment E6e), 2228 nucleotides, genomic map region 8569201 - 8566974

```
tgataagcaacatccaaatattttgaccctgcttttagtggtttttttcaaatcttattttgagtcttacttt
tagtcatagaatagctactgatttgatgcggtcttttaactgacttaatattttttacaatttcaatatatttg
cattggaatctccagtaatgaatattaaaatatatgtacaatcatttgtagatgatatcaattatattaagac
atttcagatgggctattgtagtatttaatgtgccgtatttttatggtagaataattctcagtctctggacatca
agattgctttcagtgggaatgaagattaattttacttcagtcctgattttttaggcatcaatgcatgttttcat
ttttgtcagacttttaccctcttttaatgtaattctcaacttcttatggatttacttcccaatacataaaatc
cttcaaaacaagaatgataataattttttatacttttttataaaaataaatttattttttagtccatcaaggtgtc
tgaagattttatgcctaggtatctccatatctaacttgataaggaaaataggataaacaatgctggtaatagc
aggaaagtaagtatttgaataagatgtcaaactgatatttcatgtgaacctaactcattttatggtaactaat
aattatcttatttaaatcaataggtaaaacctgtttagaaattaaaaatgagttacgatttaaagaaaattca
gatgactcattgtgagtgctagttctcttgtaggatgccactggaaatgttgaaatgaaaaatgtaagtatat
cttttggtggaaaaaaggatagtctctaggacacaaaattactgttttattttttctcaggagtttgcctaa
gggtgtgacagatgatctctgtcacttgtcttagttgtgtcctgcaataaactggatgctttataaaatacta
gacctgtgatttcgtatgctgtaatatttcatttctccatcacccctccaaattattttcttagtttggagtaa
aataataaatgtattatagtcaacatctcttgacccctcttagtttcagctaaactaagcatgtgtgtttgt
gtgttcatttatagttcatgtgtagaactatgtgaattaaatttaagaaacatgtaaagtagaggaaatagt
ttctggagaaattttcttttggatattatgcctttccattgctttctctgctgaaagcaaaaaa
agtaccctaccctgttctcctttagggaaaaactattcctataaagtattttaaatcgtgcaagtcattgc
ctagggttagctaaaacattctttttaaaaggagaaaatgccctggcttaacatttcttgtatttgtat
ctattaagataaacagtttactttgatacagtacataccaatctacttaattttttttcaggattccttttta
ctatgtttggtctgaccttttatgataacttaatatgggaacaaattagcatataattctattttccatgtga
cctcaaccagttgcagaattgtaccactactttagggggcaattgacagtttatgtagactatagcatta
attgttcccaaatgttcagtgcatcctggctaatgtgttattgaaggtgttttcacgtaagcagttagaggaa
gcacttcacccctattactaagttattaaaatgcctcctaaaggtagcattttaaattagtatacataattga
```

FIGURE 23 (cont'd)

```
ttagtaatttgtcttctcccaagcataaaacagcatagcagagttaagtgtgaccagtgaagtataagatatt
agggattgatggtgacaatgatcatagcaactaaatggattttttttttcttttagattcagccgttggtctt
tgaaatttcctgtgatgtgtttcaatctagatgcaaagaacatggaaaaatcaaagtgctcgagtggtttaaa
tatgttttgggtattcctgtttatagactataatacttttccaattaaaatcctcagttgtcacgcagaagaa
ggttaagctgtatttgattgccagttttactgaaaatgcttagtatttacagtatcaccaaatatattttgt
ttagccaaggtataggaaaaataaaataaattgtataggttgacttttttctaaaatgtctttattggattga
atgaatgtttatacctgaaaaaaaaggttcaaaaaaa
```

SEQ ID NO:17 (exon segment E7), 603 nucleotides, genomic map region 8567576 - 8566974

```
tgcatcctggctaatgtgttattgaaggtgttttcacgtaagcagttagaggaagcacttcaccctattact
aagttattaaaatgcctcctaaaggtagcattttaaattagtatacataattgattagtaatttgtcttctcc
caagcataaaacagcatagcagagttaagtgtgaccagtgaagtataagatattagggattgatggtgacaat
gatcatagcaactaaatggattttttttttcttttagattcagccgttggtctttgaaatttcctgtgatgtg
tttcaatctagatgcaaagaacatggaaaaatcaaagtgctcgagtggtttaaatatgttttgggtattcctg
tttatagactataatacttttccaattaaaatcctcagttgtcacgcagaagaaggttaagctgtatttgatt
gccagttttactgaaaatgcttagtatttacagtatcaccaaatatattttgtttagccaaggtataggaaa
aataaaataaattgtataggttgacttttttctaaaatgtctttattggattgaatgaatgtttatacctgaa
aaaaaaggttcaaaaaaa
```

SEQ ID NO:18 (exon segment E7a), 347 nucleotides, genomic map region 8567320-8566974

```
Attcagccgttggtctttgaaatttcctgtgatgtgtttcaatctagatgcaaagaacatggaaaaatcaa
agtgctcgagtggtttaaatatgttttgggtattcctgtttatagactataatacttttccaattaaaatcct
cagttgtcacgcagaagaaggttaagctgtatttgattgccagttttactgaaaatgcttagtatttacagt
atcaccaaatatattttgtttagccaaggtataggaaaaataaaataaattgtataggttgacttttttctaa
aatgtctttattggattgaatgaatgtttatacctgaaaaaaaaaggttcaaaaaaa
```

SEQ ID NO:19 (exon segment UE6/7), 832 nucleotides, genomic map region 8568408 – 8567577

```
Gtaagtatatcttttggtggaaaaaaggatagtctctaggacacaaaattactgttttatttttttctcagga
gtttgcctaagggtgtgacagatgatctctgtcacttgtcttagttgtgtcctgcaataaactggatgcttta
taaaatactagacctgtgatttcgtatgctgtaatatttcatttctccatcaccccctccaaattatttcttag
tttggagtaaaataataaatgtatatagtcaacatctcttgacccctcttagtttcagctaaactaagcat
gtgtgtttgtgtgttcattttatagttcatgtgtagaactatgtgaattaaatttaagaaacatgtaaagtag
aggaaatagtttctggagaaattttttcctttttggatattatgcccttttccattgcttttctctgcttgaa
agcaaaaaaagtaccctaccctgttctcctttaggaaaaactattcctataaagtattttaaatcgtgc
aagtcattgcctagggttagctaaaacattttttttaaaaggagaaaatgccctggctttaacattttctt
gtatttgtatctattaagataaacagtttacttgatacagtacataccatctacttaatttttttccagg
attccttttactatgtttggtctgacctttatgataacttaatatgggaacaaattagcatataattctatt
ttccatgtgacctcaaccagttgcagaattgtaccactactttagggggggcaatttgacagtttatgtagac
tatagcattaattgttcccaaatgttcag
```

SEQ ID NO:20 (exon segment E8), 276 nucleotides, genomic map region 8566289-8566014

```
gtatagcacagcatcacaacctggatactgacattgatgcagtcaagacagagaacattt
atatcatgaggaggatccctcattaccgccctttgatatccaccctacttccagaccat
ctcactcctccttaaccctggcaaccactagcatgttctccatttctataaatttgcct
ttataggaatgttatataattgcaattaaagtgtgtaaccttttggggtttgactcacc
ggcatcattttctggagattcagcttatatgtgtca
```

FIGURE 24

AFFYMETRIX PROBESET 238021_s_at

HG-U133_PLUS_2:238021_S_AT (SEQ ID NO:32)
agccgttggtctttgaaatttcctgtgatgtgtttcaatctagatgcaaagaacatggaa
aaatcaaagtgctcgagtggtttaaatatgttttgggtattcctgtttatagactataat
acttttccaattaaaatcctcagttgtcacgcagaagaaggttaagctgtatttgattgc
cagttttactgaaaatgcttagtattttacagtatcaccaaatatattttgtttagccaa
ggtatagga AFFYMETRIX PROBESET 238022_at HG-U133_PLUS_2:238022_AT (SEQ ID NO:33)
tgctgtcagctaagttcacttctgaactaaggggttcctccaaatgttggctgaaattca
tcccaaggctggtctgcaaagtctgcaattcataatggagctactgtactggctattgga
aggaggagattctgaagataaggaggtaaaacctgtttagaaattaaaaatgagttacga
tttaaagaaaattcagatgactcattgtgagtgctagttctcttgtaggatgccactgga
aatgttgaaatgaaaaatattcagccgttggtc

METHOD OF DIAGNOSING NEOPLASMS

FIELD OF THE INVENTION

The present invention relates generally to a nucleic acid molecule, the RNA and protein expression profiles of which are indicative of the onset, predisposition to the onset and/or progression of a large intestine neoplasm. More particularly, the present invention is directed to a nucleic acid molecule, the expression profiles of which are indicative of the onset and/or progression of a colorectal neoplasm, such as an adenoma or an adenocarcinoma. The expression profiles of the present invention are useful in a range of applications including, but not limited to, those relating to the diagnosis and/or monitoring of colorectal neoplasms, such as colorectal adenomas and adenocarcinomas. Accordingly, in a related aspect the present invention is directed to a method of screening a subject for the onset, predisposition to the onset and/or progression of a large intestine neoplasm by screening for modulation in the expression profile of said nucleic acid molecule markers.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Adenomas are benign tumours, or neoplasms, of epithelial origin which are derived from glandular tissue or exhibit clearly defined glandular structures. Some adenomas show recognisable tissue elements, such as fibrous tissue (fibroadenomas) and epithelial structure, while others, such as bronchial adenomas, produce active compounds that might give rise to clinical syndromes.

Adenomas may progress to become an invasive neoplasm and are then termed adenocarcinomas. Accordingly, adenocarcinomas are defined as malignant epithelial tumours arising from glandular structures, which are constituent parts of many organs of the body. The term adenocarcinoma is also applied to tumours showing a glandular growth pattern. These tumours may be sub-classified according to the substances that they produce, for example mucus secreting and serous adenocarcinomas, or to the microscopic arrangement of their cells into patterns, for example papillary and follicular adenocarcinomas. These carcinomas may be solid or cystic (cystadenocarcinomas). Each organ may produce tumours showing a variety of histological types, for example the ovary may produce both mucinous and cystadenocarcinoma.

Adenomas in different organs behave differently. In general, the overall chance of carcinoma being present within an adenoma (i.e. a focus of cancer having developed within a benign lesion) is approximately 5%. However, this is related to size of an adenoma. For instance, in the large bowel (colon and rectum specifically) occurrence of a cancer within an adenoma is rare in adenomas of less than 1 centimeter. Such a development is estimated at 40 to 50% in adenomas which are greater than 4 centimeters and show certain histopathological change such as villous change, or high grade dysplasia. Adenomas with higher degrees of dysplasia have a higher incidence of carcinoma. In any given colorectal adenoma, the predictors of the presence of cancer now or the future occurrence of cancer in the organ include size (especially greater than 9 mm) degree of change from tubular to villous morphology, presence of high grade dysplasia and the morphological change described as "serrated adenoma". In any given individual, the additional features of increasing age, familial occurrence of colorectal adenoma or cancer, male gender or multiplicity of adenomas, predict a future increased risk for cancer in the organ—so-called risk factors for cancer. Except for the presence of adenomas and its size, none of these is objectively defined and all those other than number and size are subject to observer error and to confusion as to precise definition of the feature in question. Because such factors can be difficult to assess and define, their value as predictors of current or future risk for cancer is imprecise.

Once a sporadic adenoma has developed, the chance of a new adenoma occurring is approximately 30% within 26 months.

Colorectal adenomas represent a class of adenomas which are exhibiting an increasing incidence, particularly in more affluent countries. The causes of adenoma, and of progression to adenocarcinoma, are still the subject of intensive research. To date it has been speculated that in addition to genetic predisposition, environmental factors (such as diet) play a role in the development of this condition. Most studies indicate that the relevant environmental factors relate to high dietary fat, low fibre, low vegetable intake, smoking, obesity, physical inactivity and high refined carbohydrates.

Colonic adenomas are localised areas of dysplastic epithelium which initially involve just one or several crypts and may not protrude from the surface, but with increased growth in size, usually resulting from an imbalance in proliferation and/or apoptosis, they may protrude. Adenomas can be classified in several ways. One is by their gross appearance and the major descriptors include degrees of protrusion: flat sessile (i.e. protruding but without a distinct stalk) or pedunculated (i.e. having a stalk). Other gross descriptors include actual size in the largest dimension and actual number in the colon/rectum. While small adenomas (less than say 5 or 10 millimeters) exhibit a smooth tan surface, pedunculated and especially larger adenomas tend to have a cobblestone or lobulated red-brown surface. Larger sessile adenomas may exhibit a more delicate villous surface. Another set of descriptors include the histopathological classification; the prime descriptors of clinical value include degree of dysplasia (low or high), whether or not a focus of invasive cancer is present, degree of change from tubular gland formation to villous gland formation (hence classification is tubular, villous or tubulovillous), presence of admixed hyperplastic change and of so-called "serrated" adenomas and its subgroups. Adenomas can be situated at any site in the colon and/or rectum although they tend to be more common in the rectum and distal colon. All of these descriptors, with the exception of number and size, are relatively subjective and subject to interobserver disagreement.

The various descriptive features of adenomas are of value not just to ascertain the neoplastic status of any given adenomas when detected, but also to predict a person's future risk of developing colorectal adenomas or cancer. Those features of an adenoma or number of adenomas in an individual that point to an increased future risk for cancer or recurrence of new adenomas include: size of the largest adenoma (especially 10 mm or larger), degree of villous change (especially at least 25% such change and particularly 100% such change), high grade dysplasia, number (3 or more of any size or histological status) or presence of serrated adenoma features. None except size or number is objective and all are relatively subjective and subject to interobserver disagreement. These predictors of risk for future neoplasia (hence "risk") are vital in practice because they are used to determine the rate and need for and frequency of future colonoscopic surveillance. More accurate risk classification might thus reduce workload of colonoscopy, make it more cost-effective and reduce the risk of complications from unnecessary procedures.

Adenomas are generally asymptomatic, therefore rendering difficult their diagnosis and treatment at a stage prior to when they might develop invasive characteristics and so became cancer. It is technically impossible to predict the presence or absence of carcinoma based on the gross appearance of adenomas, although larger adenomas are more likely to show a region of malignant change than are smaller adenomas. Sessile adenomas exhibit a higher incidence of malignancy than pedunculated adenomas of the same size. Some adenomas result in blood loss which might be observed or detectable in the stools; while sometimes visible by eye, it is often, when it occurs, microscopic or "occult". Larger adenomas tend to bleed more than smaller adenomas. However, since blood in the stool, whether overt or occult, can also be indicative of non-adenomatous conditions, the accurate diagnosis of adenoma is rendered difficult without the application of highly invasive procedures such as colonoscopy combined with tissue acquisition by either removal (i.e. polypectomy) or biopsy and subsequent histopathological analysis.

Accordingly, there is an on-going need to elucidate the causes of adenoma and to develop more informative diagnostic protocols or aids to diagnosis that enable one to direct colonoscopy at people more likely to have adenomas. These adenomas may be high risk, advanced or neither of these. Furthermore, it can be difficult after colonoscopy to be certain that all adenomas have been removed, especially in a person who has had multiple adenomas. An accurate screening test may minimise the need to undertake an early second colonoscopy to ensure that the colon has been cleared of neoplasms. Accordingly, the identification of molecular markers for adenomas would provide means for understanding the cause of adenomas and cancer, improving diagnosis of adenomas including development of useful screening tests, elucidating the histological stage of an adenoma, characterising a patient's future risk for colorectal neoplasia on the basis of the molecular state of an adenoma and facilitating treatment of adenomas.

To date, research has focused on the identification of gene mutations which lead to the development of colorectal neoplasms. In work leading up to the present invention, however, it has been determined that changes in expression profiles of genes which may also expressed in healthy individuals are indicative of the development of neoplasms of the large intestine, such as adenomas and adenocarcinomas. More specifically, there has been identified a gene, an increase in the expression of which is indicative of the onset of a large intestine adenoma or adenocarcinoma. Yet more particularly, it has been determined that this gene, which comprises SEQ ID NO:1 and is herein called hCG_1815491, encodes 18 identified exon segments, several of which are expressed in two or more splice variants forms. hCG_1815491 has now been found to transcribe to at least 11 variant RNA transcript forms. It has still further been determined that although the levels of multiple transcribed forms of hCG_1815491 show some level of increase in expression in the context of neoplasia development, hCG_1815491 is, in fact, alternatively spliced in a neoplastic specific manner, thereby enabling a level of diagnostic and prognostic discrimination which is rarely available in the context of a single gene and has been unavailable in terms of the diagnosis of colorectal neoplasias. The findings of the present invention have therefore facilitated the development of a screening method to diagnose the onset, or predisposition thereto, of adenocarcinoma, adenoma and/or the monitoring of conditions characterised by the development of these types of neoplasms.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains amino acid and nucleotide sequence information prepared using the programme Patent In Version 3.4, presented herein after the bibliography. Each amino acid and nucleotide sequence is identified in the sequence listing by the numeric indicator <210> followed by the sequence identifier (eg. <210>1, <210>2, etc). The length, type of sequence (amino acid, DNA, etc.) and source organism for each sequence is indicated by information provided in the numeric indicator fields <211>m <212> and <213>, respectively. Amino acid and nucleotide sequences referred to in the specification are identified by the indicator SEQ ID NO: followed by the sequence identifier (eg. SEQ ID NO:1, SEQ ID NO: 2, etc). The sequence identifier referred to in the specification correlates to the information provided in numeric indicator field <400> in the sequence listing, which is followed by the sequence identifier (eg. <400>1, <400>2, etc). That is SEQ ID NO: 1 as detailed in the specification correlates to the sequence indicated as <400>1 in the sequence listing.

One aspect of the present invention is directed to a method of screening for the onset or predisposition to the onset of a large intestine neoplasm in an individual, said method comprising measuring the level of expression of hCG_1815491 in a biological sample from said individual wherein a higher level of expression of hCG_1815491 or variant thereof relative to control levels is indicative of a neoplastic large intestine cell or a cell predisposed to the onset of a neoplastic state.

The present invention more particularly provides a method of screening for the onset or predisposition to the onset of a large intestine neoplasm in an individual, said method comprising measuring the level of expression of a gene comprising a sequence of nucleotides as set forth in SEQ ID NO:1 or a sequence having at least 90% similarity to SEQ ID NO:1 across the length of the gene, or variant of SEQ ID NO:1, in a biological sample from said individual wherein a higher level of expression of said gene or variant thereof relative to control levels is indicative of a neoplastic large intestine cell or a cell predisposed to the onset of a neoplastic state.

Another aspect of the present invention provides a method of screening for the onset or predisposition to the onset of a large intestine neoplasm in an individual, said method comprising measuring the level of expression of one or more RNA transcripts, which transcripts comprise an RNA sequence characterised by the sequence of one of:
(i) SEQ ID NO:21, or a sequence having at least 90% similarity across the length of the sequence, or variant of SEQ ID NO:21;
(ii) SEQ ID NO:22, or a sequence having at least 90% similarity across the length of the sequence, or variant of SEQ ID NO:22;
(iii) SEQ ID NO:23, or a sequence having at least 90% similarity across the length of the sequence, or variant of SEQ ID NO:23;
(iv) SEQ ID NO:24, or a sequence having at least 90% similarity across the length of the sequence, or variant of SEQ ID NO:24;
(v) SEQ ID NO:25, or a sequence having at least 90% similarity across the length of the sequence, or variant of SEQ ID NO:25;
(vi) SEQ ID NO:26, or a sequence having at least 90% similarity across the length of the sequence, or variant of SEQ ID NO:26;
(vii) SEQ ID NO:27, or a sequence having at least 90% similarity across the length of the sequence, or variant of SEQ ID NO:27;
(viii) SEQ ID NO:28, or a sequence having at least 90% similarity across the length of the sequence, or variant of SEQ ID NO:28;
(ix) SEQ ID NO:29, or a sequence having at least 90% similarity across the length of the sequence, or variant of SEQ ID NO:29;
(x) SEQ ID NO:30, or a sequence having at least 90% similarity across the length of the sequence, or variant of SEQ ID NO:30;
(xi) SEQ ID NO:31, or a sequence having at least 90% similarity across the length of the sequence, or variant of SEQ ID NO:31
in a biological sample from said individual wherein a higher level of said RNA transcript or variant thereof relative to control levels is indicative of a neoplastic large intestine cell or a cell predisposed to the onset of a neoplastic state.

In still another aspect the RNA transcript, the level of expression of which is assessed in accordance with the method of the present invention, is one or more of the transcripts characterised by the sequence of one of:
(i) SEQ ID NO:21, or a sequence having at least 90% similarity across the length of the sequence, or variant of SEQ ID NO:21;
(ii) SEQ ID NO:24, or a sequence having at least 90% similarity across the length of the sequence, or variant of SEQ ID NO:24;
(iii) SEQ ID NO:27, or a sequence having at least 90% similarity across the length of the sequence, or variant of SEQ ID NO:27;
(iv) SEQ ID NO:22, or a sequence having at least 90% similarity across the length of the sequence, or variant of SEQ ID NO:22;
(v) SEQ ID NO:23, or a sequence having at least 90% similarity across the length of the sequence, or variant of SEQ ID NO:23;
(vi) SEQ ID NO:30, or a sequence having at least 90% similarity across the length of the sequence, or variant of SEQ ID NO:30;
(vii) SEQ ID NO:31, or a sequence having at least 90% similarity across the length of the sequence, or variant of SEQ ID NO:31;
(viii) SEQ ID NO:25, or a sequence having at least 90% similarity across the length of the sequence, or variant of SEQ ID NO:25.

In yet another aspect said RNA transcript is one or more of the transcripts characterised by the sequence of one of:
(i) SEQ ID NO:21, or a sequence having at least 90% similarity across the length of the sequence, or variant of SEQ ID NO:21;
(ii) SEQ ID NO:24, or a sequence having at least 90% similarity across the length of the sequence, or variant of SEQ ID NO:24;
(iii) SEQ ID NO:27, or a sequence having at least 90% similarity across the length of the sequence, or variant of SEQ ID NO:27;
(iv) SEQ ID NO:22, or a sequence having at least 90% similarity across the length of the sequence, or variant of SEQ ID NO:22.

In a further aspect there is provided a method of screening for the onset or predisposition to the onset of a large intestine neoplasm in an individual, said method comprising measuring the level of expression of an RNA transcript, which transcript comprises one or more exon segments selected from:
(i) an exon segment defined by SEQ ID NO:2, or a sequence having at least 90% similarity across the length of the sequence, or variant of SEQ ID NO:2;
(ii) an exon segment defined by SEQ ID NO:3, or a sequence having at least 90% similarity across the length of the sequence, or variant of SEQ ID NO:3
(iii) an exon segment defined by SEQ ID NO:4, or a sequence having at least 90% similarity across the length of the sequence, or variant of SEQ ID NO:4;
(iv) an exon segment defined by SEQ ID NO:5, or a sequence having at least 90% similarity across the length of the sequence, or variant of SEQ ID NO:5;
(v) an exon segment defined by SEQ ID NO:6, or a sequence having at least 90% similarity across the length of the sequence, or variant of SEQ ID NO:6;
(vi) an exon segment defined by SEQ ID NO:7, or a sequence having at least 90% similarity across the length of the sequence, or variant of SEQ ID NO:7;
(vii) an exon segment defined by SEQ ID NO:8, or a sequence having at least 90% similarity across the length of the sequence, or variant of SEQ ID NO:8;
(viii) an exon segment defined by SEQ ID NO:9, or a sequence having at least 90% similarity across the length of the sequence, or variant of SEQ ID NO:9;
(ix) an exon segment defined by SEQ ID NO:10, or a sequence having at least 90% similarity across the length of the sequence, or variant of SEQ ID NO:10;
(x) an exon segment defined by SEQ ID NO:11, or a sequence having at least 90% similarity across the length of the sequence, or variant of SEQ ID NO:11;
(xi) an exon segment defined by SEQ ID NO:12, or a sequence having at least 90% similarity across the length of the sequence, or variant of SEQ ID NO:12 an exon segment defined by SEQ ID NO:13, or a sequence having at least 90% similarity across the length of the sequence, or variant of SEQ ID NO:13

(xiii) an exon segment defined by SEQ ID NO:14, or a sequence having at least 90% similarity across the length of the sequence, or variant of SEQ ID NO:14
(xiv) an exon segment defined by SEQ ID NO:15, or a sequence having at least 90% similarity across the length of the sequence, or variant of SEQ ID NO:15
(xv) an exon segment defined by SEQ ID NO:16, or a sequence having at least 90% similarity across the length of the sequence, or variant of SEQ ID NO:16
(xvi) an exon segment defined by SEQ ID NO:17, or a sequence having at least 90% similarity across the length of the sequence, or variant of SEQ ID NO:17
(xvii) an exon segment defined by SEQ ID NO:18, or a sequence having at least 90% similarity across the length of the sequence, or variant of SEQ ID NO:18
(xviii) an exon segment defined by SEQ ID NO:19, or a sequence having at least 90% similarity across the length of the sequence, or variant of SEQ ID NO:19; or
(xix) an exon segment defined by SEQ ID NO:20, or a sequence having at least 90% similarity across the length of the sequence, or variant of SEQ ID NO:20
in a biological sample from said individual wherein a higher level of said RNA transcript or variant thereof relative to control levels is indicative of a neoplastic large intestine cell or a cell predisposed to the onset of a neoplastic state.

More particularly there is provided a method of screening for the onset or predisposition to the onset of a large intestine neoplasm in an individual, said method comprising measuring the level of expression of an RNA transcript, which transcript comprises one or more exon segments selected from:
(i) an exon segment defined by SEQ ID NO:3, or a sequence having at least 90% similarity across the length of the sequence, or variant of SEQ ID NO:3
(ii) an exon segment defined by SEQ ID NO:4, or a sequence having at least 90% similarity across the length of the sequence, or variant of SEQ ID NO:4;
(iii) an exon segment defined by SEQ ID NO:5, or a sequence having at least 90% similarity across the length of the sequence, or variant of SEQ ID NO:5;
(iv) an exon segment defined by SEQ ID NO:6, or a sequence having at least 90% similarity across the length of the sequence, or variant of SEQ ID NO:6;
(v) an exon segment defined by SEQ ID NO:7, or a sequence having at least 90% similarity across the length of the sequence, or variant of SEQ ID NO:7;
(vi) an exon segment defined by SEQ ID NO:8, or a sequence having at least 90% similarity across the length of the sequence, or variant of SEQ ID NO:8;
(vii) an exon segment defined by SEQ ID NO:9, or a sequence having at least 90% similarity across the length of the sequence, or variant of SEQ ID NO:9; or
(viii) an exon segment defined by SEQ ID NO:10, or a sequence having at least 90% similarity across the length of the sequence, or variant of SEQ ID NO:10;
(ix) an exon segment defined by SEQ ID NO:11, or a sequence having at least 90% similarity across the length of the sequence, or variant of SEQ ID NO:11;
(x) an exon segment defined by SEQ ID NO:12, or a sequence having at least 90% similarity across the length of the sequence, or variant of SEQ ID NO:12;
(xi) an exon segment defined by SEQ ID NO:13, or a sequence having at least 90% similarity across the length of the sequence, or variant of SEQ ID NO:13;
(xii) an exon segment defined by SEQ ID NO:14, or a sequence having at least 90% similarity across the length of the sequence, or variant of SEQ ID NO:14;
(xiii) an exon segment defined by SEQ ID NO:15, or a sequence having at least 90% similarity across the length of the sequence, or variant of SEQ ID NO:15;
(xiv) an exon segment defined by SEQ ID NO:18, or a sequence having at least 90% similarity across the length of the sequence, or variant of SEQ ID NO:18;
(xv) an exon segment defined by SEQ ID NO:19, or a sequence having at least 90% similarity across the length of the sequence, or variant of SEQ ID NO:19
in a biological sample from said individual wherein a higher level of said RNA transcript or variant thereof relative to control levels is indicative of a neoplastic large intestine cell or a cell predisposed to the onset of a neoplastic state.

Yet more particularly there is provided a method of screening for the onset or predisposition to the onset of a large intestine neoplasm in an individual, said method comprising measuring the level of expression of an RNA transcript selected from:
(i) an RNA transcript which comprises each of the exon segments defined by SEQ ID NO:5, SEQ ID NO:6, SEQ ID NO:10 and SEQ ID NO:12, or a sequence having at least 90% similarity across the length of these sequences, or variants of SEQ ID NO:5, SEQ ID NO:6, SEQ ID NO:10 and SEQ ID NO:12;
(ii) an RNA transcript which comprises each of the exon segments defined by SEQ ID NO:5, SEQ ID NO:6, SEQ ID NO:10 and SEQ ID NO:14, or a sequence having at least 90% similarity across the length of these sequences, or variants of SEQ ID NO:5, SEQ ID NO:6, SEQ ID NO:10 and SEQ ID NO:14;
(iii) an RNA transcript which comprises each of the exon segments defined by SEQ ID NO:3 and SEQ ID NO:6, or a sequence having at least 90% similarity across the length of these sequences, or variants of SEQ ID NO:3 and SEQ ID NO:6;
(iv) an RNA transcript which comprises each of the exon segments defined by SEQ ID NO:11, SEQ ID NO:12 and SEQ ID NO:18, or a sequence having at least 90% similarity across the length of these sequences, or variants of SEQ ID NO:11, SEQ ID NO:12 and SEQ ID NO:18;
(v) an RNA transcript which comprises each of the exon segments defined by SEQ ID NO:4 and SEQ ID NO:7, or a sequence having at least 90% similarity across the length of these sequences, or variants of SEQ ID NO:4 and SEQ ID NO:7;
(vi) an RNA transcript which comprises each of the exon segments defined by SEQ ID NO:6, SEQ ID NO:10 and SEQ ID NO:13, or a sequence having at least 90% similarity across the length of these sequences, or variants of SEQ ID NO:6, SEQ ID NO:10 and SEQ ID NO:13;
(vii) an RNA transcript which comprises each of the exon segments defined by SEQ ID NO:6 and SEQ ID NO:8, or a sequence having at least 90% similarity across the length of these sequences, or variants of SEQ ID NO:6 and SEQ ID NO:8;
(viii) an RNA transcript which comprises each of the exon segments defined by SEQ ID NO:19 and SEQ ID NO:18, or a sequence having at least 90% similarity across the length of these sequences, or variants of SEQ ID NO:19 and SEQ ID NO:18;
(ix) an RNA transcript which comprises each of the exon segments defined by SEQ ID NO:15 and SEQ ID NO:18, or a sequence having at least 90% similarity across the length of these sequences, or variants of SEQ ID NO:15 and SEQ ID NO:18;
(x) an RNA transcript which comprises each of the exon segments defined by SEQ ID NO:6 and SEQ ID NO:9, or a sequence having at least 90% similarity across the length of these sequences, or variants of SEQ ID NO:6 and SEQ ID NO:9; or
(xi) an RNA transcript which comprises each of the exon segments defined by SEQ ID NO:4, SEQ ID NO:6, SEQ ID NO:10 and SEQ ID NO:12, or a sequence having at least 90% similarity across the length of these sequences, or variants of SEQ ID NO:4, SEQ ID NO:6, SEQ ID NO:10 and SEQ ID NO:12 in a biological sample from said individual wherein a higher level of said RNA transcript or variant thereof relative to control levels is indicative of a neoplastic large intestine cell or a cell predisposed to the onset of a neoplastic state.

Still more particularly there is provided a method of screening for the onset or predisposition to the onset of a large intestine neoplasm in an individual, said method comprising measuring the level of expression of an RNA transcript, which transcript is selected from:
(i) an RNA transcript which comprises each of the exon segments defined by SEQ ID NO:5, SEQ ID NO:6, SEQ ID NO:10 and SEQ ID NO:12, or a sequence having at least 90% similarity across the length of these sequences, or variants of SEQ ID NO:5, SEQ ID NO:6, SEQ ID NO:10 and SEQ ID NO:12;
(ii) an RNA transcript which comprises each of the exon segments defined by SEQ ID NO:5, SEQ ID NO:6, SEQ ID NO:10 and SEQ ID NO:14, or a sequence having at least 90% similarity across the length of these sequences, or variants of SEQ ID NO:5, SEQ ID NO:6, SEQ ID NO:10 and SEQ ID NO:14;
(iii) an RNA transcript which comprises each of the exon segments defined by SEQ ID NO:11, SEQ ID NO:12, SEQ ID NO:18 and SEQ ID NO:24, or a sequence having at least 90% similarity across the length of these sequences, or variants of SEQ ID NO:11, SEQ ID NO:12, SEQ ID NO:18 and SEQ ID NO:24; or
(iv) an RNA transcript which comprises each of the exon segments defined by SEQ ID NO:6 and SEQ ID NO:8, or a sequence having at least 90% similarity across the length of these sequences, or variants of SEQ ID NO:6 and SEQ ID NO:8.

in a biological sample from said individual wherein a higher level of said RNA transcript or variant thereof relative to control levels is indicative of a neoplastic large intestine cell or a cell predisposed to the onset of a neoplastic state.

In another further aspect, there is therefore provided a method of screening for the onset or predisposition to the onset of a large intestine neoplasm in an individual, said method comprising measuring the level of expression of one or more RNA transcripts, which transcripts comprise an RNA sequence characterised by the sequence of one of:
(i) SEQ ID NO:21 or a sequence having at least 90% similarity across the length of the sequence, or variant of SEQ ID NO:21;
(ii) SEQ ID NO:24 or a sequence having at least 90% similarity across the length of the sequence, or variant of SEQ ID NO:24;
(iii) SEQ ID NO:25 or a sequence having at least 90% similarity across the length of the sequence, or variant of SEQ ID NO:25;
(iv) SEQ ID NO:26 or a sequence having at least 90% similarity across the length of the sequence, or variant of SEQ ID NO:26;
(v) SEQ ID NO:27 or a sequence having at least 90% similarity across the length of the sequence, or variant of SEQ ID NO:27;
(vi) SEQ ID NO:29 or a sequence having at least 90% similarity across the length of the sequence, or variant of SEQ ID NO:29;
(vii) SEQ ID NO:30 or a sequence having at least 90% similarity across the length of the sequence, or variant of SEQ ID NO:30; or
(viii) SEQ ID NO:31 or a sequence having at least 90% similarity across the length of the sequence, or variant of SEQ ID NO:31;

in a biological sample from said individual wherein a higher level of expression of the genes or transcripts of group (i) and/or group (ii) relative to background levels is indicative of a neoplastic cell or a cell predisposed to the onset of a neoplastic state.

In yet another aspect said transcripts comprise an RNA sequence characterised by the sequence of one of:
(i) SEQ ID NO:21 or a sequence having at least 90% similarity across the length of the sequence, or variant of SEQ ID NO:21;
(ii) SEQ ID NO:22 or a sequence having at least 90% similarity across the length of the sequence, or variant of SEQ ID NO:22;
(iii) SEQ ID NO:23 or a sequence having at least 90% similarity across the length of the sequence, or variant of SEQ ID NO:23;
(iv) SEQ ID NO:24 or a sequence having at least 90% similarity across the length of the sequence, or variant of SEQ ID NO:24; or
(v) SEQ ID NO:27 or a sequence having at least 90% similarity across the length of the sequence, or variant of SEQ ID NO:27;

in a biological sample from said individual wherein a higher level of expression of the genes or transcripts of group (i) and/or group (ii) relative to background levels is indicative of a neoplastic cell or a cell predisposed to the onset of a neoplastic state.

Still another aspect of the present invention provides a diagnostic kit for assaying biological samples comprising an agent for detecting one or more neoplastic marker reagents useful for facilitating the detection by the agent in the first compartment. Further means may also be included, for example, to receive a biological sample. The agent may be any suitable detecting molecule.

BRIEF DESCRIPTION OF THE DRAWINGS

Figure 22:
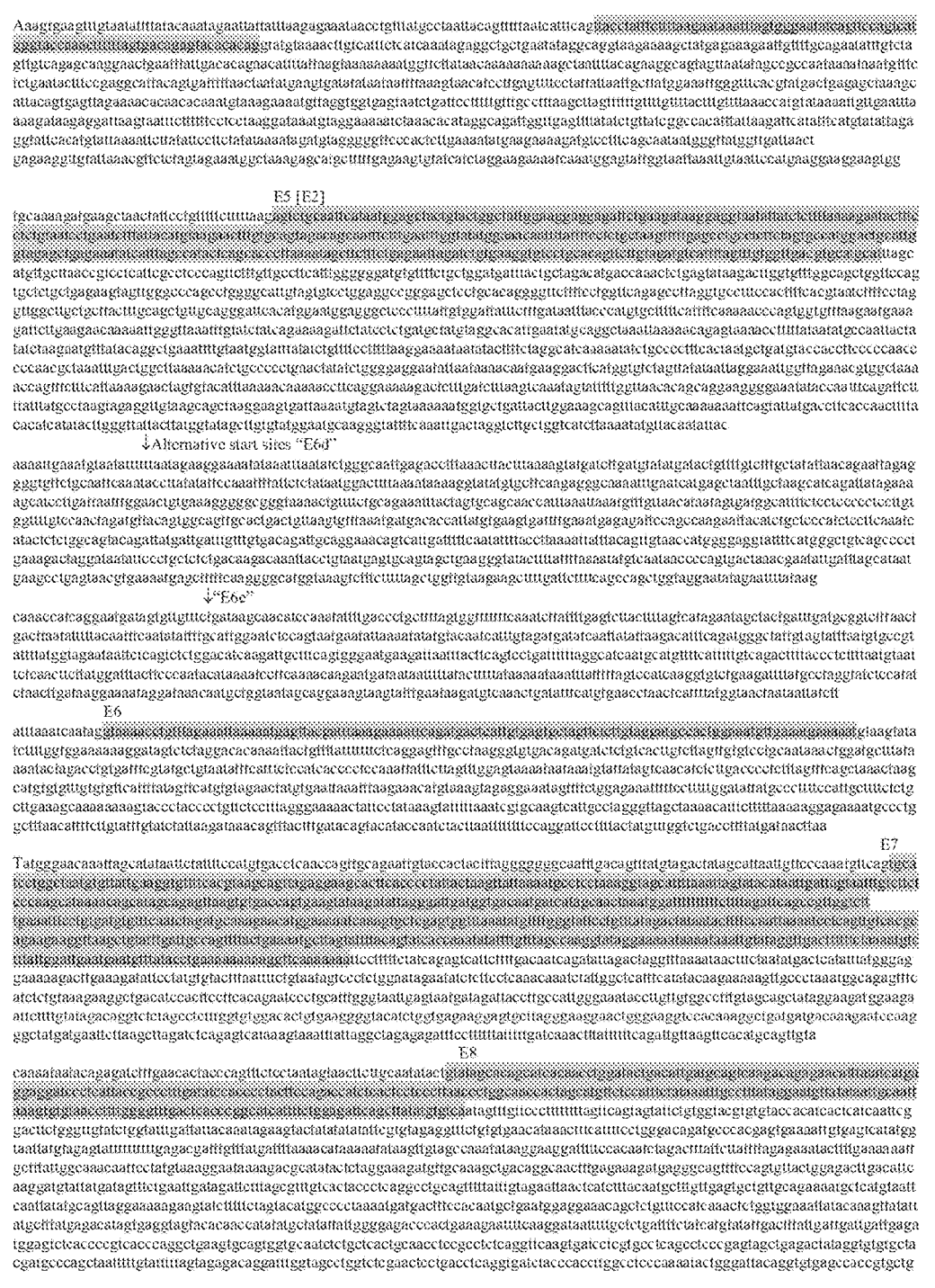
Figure 22:
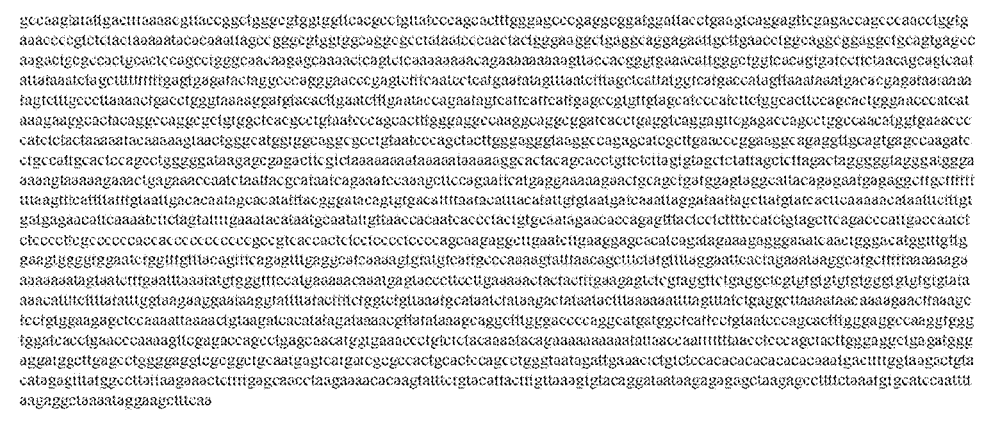

FIG. 22. SEQ ID NO:1 is specified by a 17,008 nucleotide sequence located on the minus strand of human chromosome 16 in the map region 8579310 to 8562303 (+strand nomenclature) as specified by the NCBI contig ref: NT_010498.15|Hs16_10655, NCBI 36 March 2006 genome. Grey shading indicates location of nucleotide segments, i.e. exons, utilised in the RNA variants further described in FIG. 23.

FIG. 23. SEQ ID NO: 2 to SEQ ID NO: 20 identified to be alternatively spliced to generate the 10 RNA variants depicted in FIG. 4.

FIG. 24. Nucleotide sequences targeted by Affymetrix probeset ID 238021_s_at and probeset ID 238022_at.

DETAILED DESCRIPTION OF THE INVENTION

Figure 1:
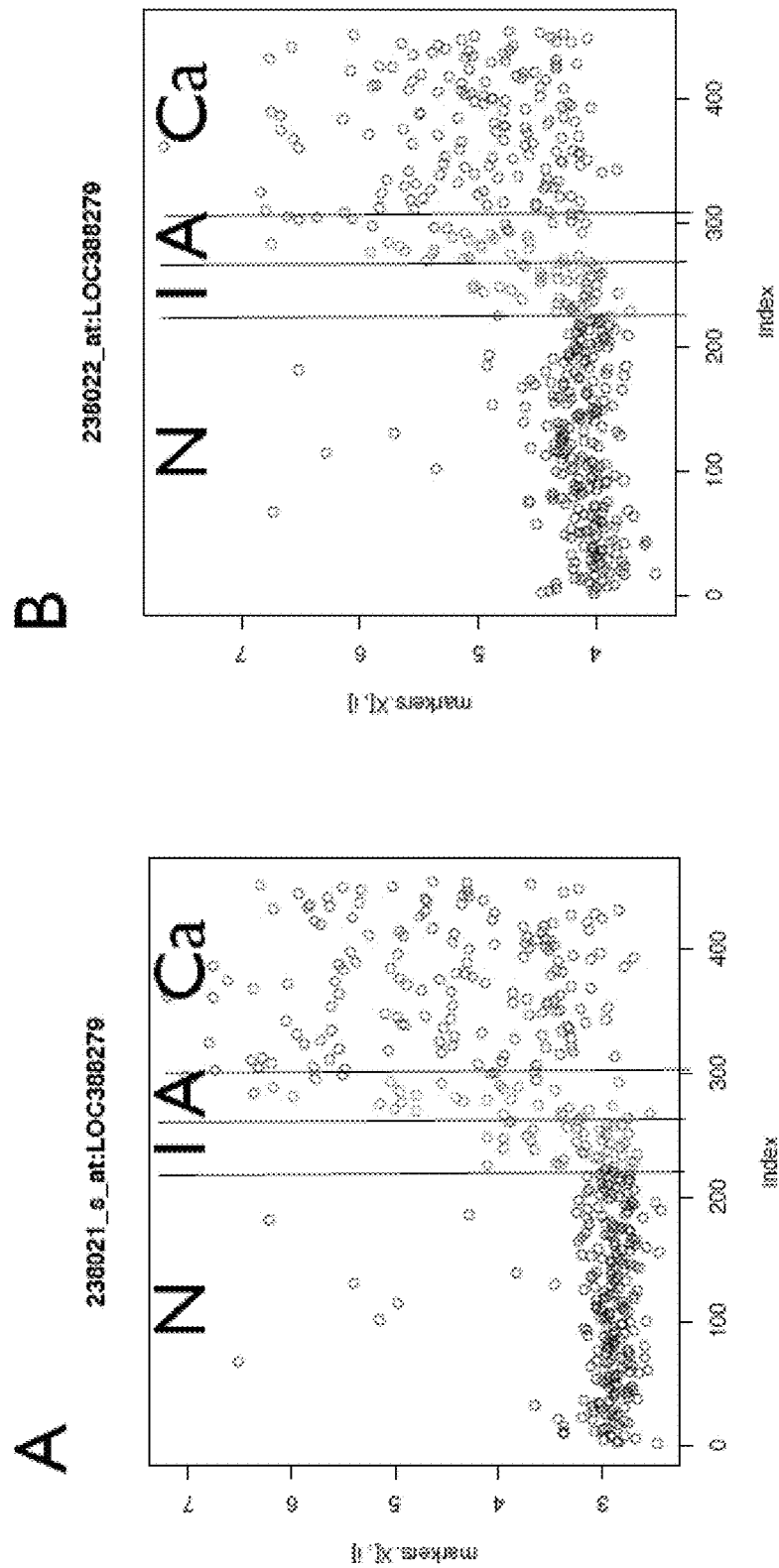
FIG. 1. Detection of hCG_1815491 gene expression. The expression from hCG_1815491 in colon tissue specimens from 222 non-diseased controls (black, area designated with an "N"), 42 colitis tissues (red, are designated by an "I"), 29 adenoma (green, area designated by an "A") and 161 adenocarcinoma (blue, area designated by "Ca") were measured by hybridization to Affymetrix probeset IDs 238021_s_at (A) and 238022_at (B). The two Affymetrix probeset IDs were included on the commercially available Affymetrix GeneChip HGU133A & HGU13B. Gene expression profiles from RNA extracted from the total of 454 colon tissue specimens were obtained from GeneLogic Inc (Gaithersburg, Md. USA). A quality control analysis was performed to remove arrays not meeting essential quality control measures as defined by the manufacturer. Transcript expression levels were calculated by both Microarray Suite (MAS) 5.0 (Affymetrix) and the Robust Multichip Average (RMA) normalization techniques (Affymetrix. GeneChip expression data analysis fundamentals. Affymetrix, Santa Clara, Calif. USA, 2001; Hubbell et al. Bioinformatics, 18:1585-1592, 2002; Irizarry et al. Nucleic Acid Research, 31, 2003) MAS normalized data was used for performing standard quality control routines and the final data set was normalized with RMA for all subsequent analyses.

The present invention is predicated, in part, on the elucidation of a gene expression profile, specifically that of hCG_1815491, which characterises large intestine cellular populations in terms of their neoplastic state. This finding has now facilitated the development of routine means of screening for the onset or predisposition to the onset of a large intestine neoplasm based on screening for upregulation of the expression of this molecule, relative to control expression levels. To this end, in addition to assessing expression levels of hCG_1815491 relative to normal or non-neoplastic levels, it has been determined that hCG_1815491 is alternatively spliced in a neoplastic specific manner, thereby enabling a high level of discrimination.

In accordance with the present invention, it has been determined that hCG_1815491 is modulated, in terms of differential changes to its levels of expression, depending on whether the cell expressing that gene is neoplastic or not. It should be understood that reference to a gene "expression product" or "expression of a gene" is a reference to either a transcription product (such as primary RNA or mRNA) or a translation product such as protein. This gene and its expression products, whether they be RNA transcripts or encoded proteins, are collectively referred to as the "neoplastic marker".

Accordingly, one aspect of the present invention is directed to a method of screening for the onset or predisposition to the onset of a large intestine neoplasm in an individual, said method comprising measuring the level of expression of hCG_1815491 in a biological sample from said individual wherein a higher level of expression of hCG_1815491 or variant thereof relative to control levels is indicative of a neoplastic large intestine cell or a cell predisposed to the onset of a neoplastic state.

Reference to "large intestine" should be understood as a reference to a cell derived from one of the six anatomical regions of the large intestine, which regions commence after the terminal region of the ileum, these being:
  (i) the cecum;
  (ii) the ascending colon;
  (iii) the transverse colon;
  (iv) the descending colon;
  (v) the sigmoid colon; and
  (vi) the rectum.

Reference to "neoplasm" should be understood as a reference to a lesion, tumour or other encapsulated or unencapsulated mass or other form of growth which comprises neoplastic cells. A "neoplastic cell" should be understood as a reference to a cell exhibiting abnormal growth. The term "growth" should be understood in its broadest sense and includes reference to proliferation. In this regard, an example of abnormal cell growth is the uncontrolled proliferation of a cell. Another example is failed apoptosis in a cell, thus prolonging its usual life span. The neoplastic cell may be a benign cell or a malignant cell. In a preferred embodiment, the subject neoplasm is an adenoma or an adenocarcinoma. Without limiting the present invention to any one theory or mode of action, an adenoma is generally a benign tumour of epithelial origin which is either derived from epithelial tissue or exhibits clearly defined epithelial structures. These structures may take on a glandular appearance. It can comprise a malignant cell population within the adenoma, such as occurs with the progression of a benign adenoma to a malignant adenocarcinoma.

Preferably, said neoplastic cell is an adenoma or adenocarcinoma and even more preferably a colorectal adenoma or adenocarcinoma.

Reference to "hCG_1815491" and its transcribed and translated expression products should be understood as a reference to all forms of this gene and to fragments thereof. As would be appreciated by the person of skill in the art, genes are known to exhibit allelic or polymorphic variation between individuals. Accordingly, reference to "hCG_1815491" should be understood to extend to such variants which, in terms of the present diagnostic applications, achieve the same outcome despite the fact that minor genetic variations between the actual nucleic acid sequences may exist between individuals. Reference to "variants" should also be understood to extend to alternative transcriptional forms of hCG_1815491, such as splice variants or variants which otherwise exhibit variation to exon expression and arrangement, such as in terms of multiple exon combinations or alternate 5'- or 3'-ends. The present invention should therefore be understood to extend to all forms of RNA (eg mRNA, primary RNA transcript, miRNA, etc), cDNA and peptide isoforms which arise from alternative splicing or any other mutation, polymorphic or allelic variation. It should also be understood to include reference to any subunit polypeptides such as precursor forms which may be generated, whether existing as a monomer, multimer, fusion protein or other complex.

Figure 4:
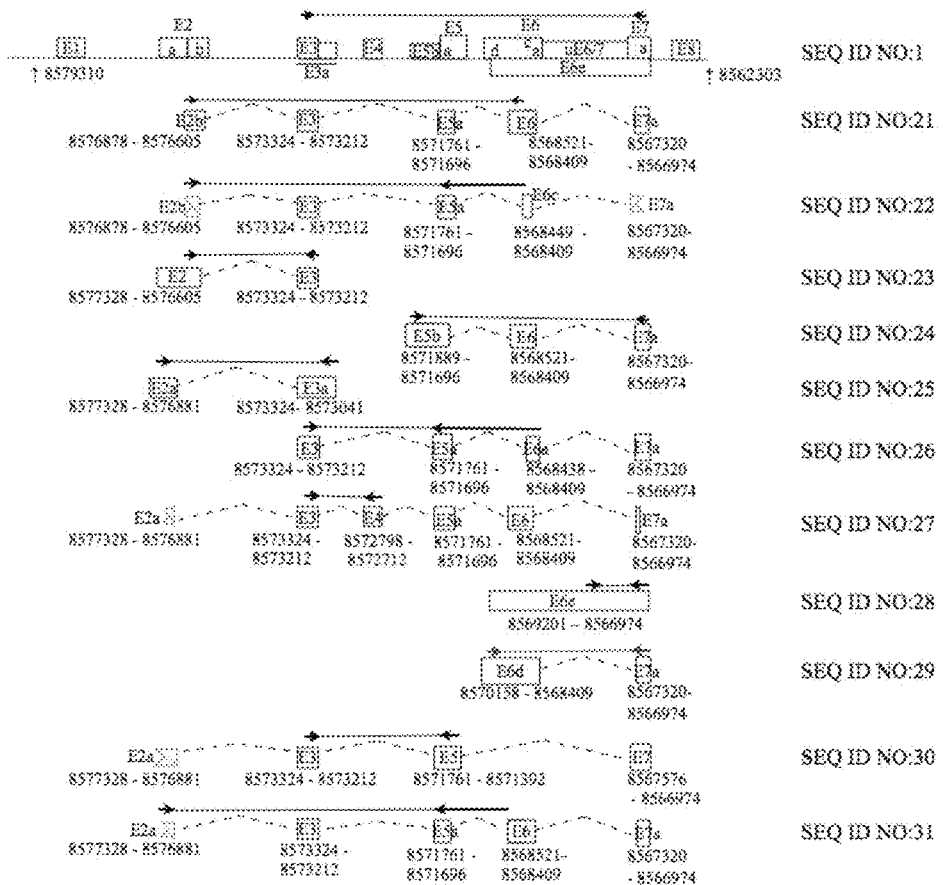
FIG. 4. Schematic representation of predicted RNA variants derived from hCG_1815491. cDNA clones derived from map region 8579310 to 8562303 (SEQ ID NO:1) on human chromosome 16 were used to locate exon sequences. Arrows: Oligo nucleotide primer sets (Table 5) were designed to allow measurement of individual RNA variants by PCR. Oligonucleotide primers covering splice junctions are shown as spanning intron sequences which is not included in the actual oligonucleotide primer sequence. Exon nucleotide sequence and genomic locations are given in FIGS. 22 and 23. The relationship of exon "E" numbering and SEQ ID NO. numbering is further defined in Table 1.

Without limiting the present invention to any one theory or mode of action, the hCG_1815491 genomic sequence comprises SEQ ID NO:1. The SEQ ID NO:1 nucleic acid molecule has been determined to generate at least 18 alternatively spliced exon segments, as follows:
(i) Exon segment E1 which is defined by SEQ ID NO:2
(ii) Exon segment E2 which is defined by SEQ ID NO:3
(iii) Exon segment E2a which is defined by SEQ ID NO:4
(iv) Exon segment E2b which is defined by SEQ ID NO:5
(v) Exon segment E3 which is defined by SEQ ID NO:6
(vi) Exon segment E3a which is defined by SEQ ID NO:7
(vii) Exon segment E4 which is defined by SEQ ID NO:8
(viii) Exon segment E5 which is defined by SEQ ID NO:9
(ix) Exon segment E5a which is defined by SEQ ID NO:10
(x) Exon segment E5b which is defined by SEQ ID NO:11
(xi) Exon segment E6 which is defined by SEQ ID NO:12
(xii) Exon segment E6a which is defined by SEQ ID NO:13
(xiii) Exon segment E6c which is defined by SEQ ID NO:14
(xiv) Exon segment E6d which is defined by SEQ ID NO:15
(xv) Exon segment E6e which is defined by SEQ ID NO:16
(xvi) Exon segment E7 which is defined by SEQ ID NO:17
(xvii) Exon segment E1a which is defined by SEQ ID NO:18
(xviii) Exon segment UE6/7 which is defined by SEQ ID NO:19
(xix) Exon segment E8 which is defined by SEQ ID NO:20.
SEQ ID NO:1 has at least 8 putative exon segments (SEQ ID NO:2, SEQ ID NO:3, SEQ ID NO:6, SEQ ID NO:8, SEQ ID NO:9, SEQ ID NO:12, SEQ ID NO:17, SEQ ID NO:20) of which several are alternatively spliced. It has been still further determined that from this genomic structure there are transcribed at least 11 different RNA transcripts which each comprise one of the sequences depicted in SEQ ID NOs: 21-31, Table 1 and are schematically depicted in FIG. 4. It would be appreciated that the sequences which are depicted in SEQ ID NOs:21-31 take the form of DNA since they have been assembled using SEQ ID NO:1. However, the RNA transcripts which are generated either in vivo or in vitro would be characterised by comprising a corresponding sequence, albeit in RNA form.

Accordingly, in terms of the method of the present invention, screening for the "level of expression" of hCG_1815491 may be achieved in a variety of ways including screening for any of the forms of RNA transcribed from hCG_1815491, cDNA generated therefrom or a protein expression product. Changes to the levels of any of these products is indicative of changes to the expression of the subject gene. Still further, the molecule which is identified and measured may be a whole molecule or a fragment thereof. For example, one is more likely to identify only fragments of RNA or protein molecules in a stool sample although provided that said fragment comprises sufficient sequence to indicate that its origin with the hCG_1815491 gene is more likely than not (such as one or more of the exon segments or exons detailed above), fragmented hCG_1815491 molecules are useful in the context of the method of the present invention. For example, the identification of RNA transcripts corresponding to one or more of the exon segments herein defined, alone or in combination, is a useful means of screening for changes to hCG_1815491 expression.

The present invention therefore more particularly provides a method of screening for the onset or predisposition to the onset of a large intestine neoplasm in an individual, said method comprising measuring the level of expression of a gene comprising a sequence of nucleotides as set forth in SEQ ID NO:1 or a sequence having at least 90% similarity to SEQ ID NO:1 across the length of the gene, or variant of SEQ ID NO:1, in a biological sample from said individual wherein a higher level of expression of said gene or variant thereof relative to control levels is indicative of a neoplastic large intestine cell or a cell predisposed to the onset of a neoplastic state.

Reference to "gene" herein should be understood as a reference to any genomic locus or set of loci which give rise to RNA transcripts from one or more promoters, including transcripts formed by the splicing of two or more exons as hereinbefore described. It would be appreciated that not all RNA transcripts are necessarily translated to a protein expression product.

In one embodiment of the present invention, said hCG_1815491 expression levels are assessed by screening for the levels of expression of one or more of the RNA transcripts which are generated from the SEQ ID NO:1 genomic sequence.

Accordingly, in accordance with this embodiment there is provided a method of screening for the onset or predisposition to the onset of a large intestine neoplasm in an individual, said method comprising measuring the level of expression of one or more RNA transcripts, which transcripts comprise an RNA sequence characterised by the sequence of one of:
(i) SEQ ID NO:21, or a sequence having at least 90% similarity across the length of the sequence, or variant of SEQ ID NO:21;
(ii) SEQ ID NO:22, or a sequence having at least 90% similarity across the length of the sequence, or variant of SEQ ID NO:22;
(iii) SEQ ID NO:23, or a sequence having at least 90% similarity across the length of the sequence, or variant of SEQ ID NO:23;
(iv) SEQ ID NO:24, or a sequence having at least 90% similarity across the length of the sequence, or variant of SEQ ID NO:24;

(v) SEQ ID NO:25, or a sequence having at least 90% similarity across the length of the sequence, or variant of SEQ ID NO:25;
(vi) SEQ ID NO:26, or a sequence having at least 90% similarity across the length of the sequence, or variant of SEQ ID NO:26;
(vii) SEQ ID NO:27, or a sequence having at least 90% similarity across the length of the sequence, or variant of SEQ ID NO:27;
(viii) SEQ ID NO:28, or a sequence having at least 90% similarity across the length of the sequence, or variant of SEQ ID NO:28;
(ix) SEQ ID NO:29, or a sequence having at least 90% similarity across the length of the sequence, or variant of SEQ ID NO:29;
(x) SEQ ID NO:30, or a sequence having at least 90% similarity across the length of the sequence, or variant of SEQ ID NO:30;
(xi) SEQ ID NO:31, or a sequence having at least 90% similarity across the length of the sequence, or variant of SEQ ID NO:31 in a biological sample from said individual wherein a higher level of said RNA transcript or variant thereof relative to control levels is indicative of a neoplastic large intestine cell or a cell predisposed to the onset of a neoplastic state.

Reference to said RNA transcript being "characterised by" the sequence of any one of SEQ ID NOs:21-31 should be understood to mean that the subject RNA transcript comprises a corresponding RNA form of the DNA sequence information which is depicted in SEQ ID NOs:21-31. That is, each of the DNA nucleotides depicted in these sequences should be replaced with the corresponding RNA version of that nucleotide.

Preferably, the RNA transcript, the level of expression of which is assessed in accordance with the method of the present invention, is one or more of the transcripts characterised by the sequence of one of:
(i) SEQ ID NO:21, or a sequence having at least 90% similarity across the length of the sequence, or variant of SEQ ID NO:21;
(ii) SEQ ID NO:24, or a sequence having at least 90% similarity across the length of the sequence, or variant of SEQ ID NO:24;
(iii) SEQ ID NO:27, or a sequence having at least 90% similarity across the length of the sequence, or variant of SEQ ID NO:27;
(iv) SEQ ID NO:22, or a sequence having at least 90% similarity across the length of the sequence, or variant of SEQ ID NO:22;
(v) SEQ ID NO:23, or a sequence having at least 90% similarity across the length of the sequence, or variant of SEQ ID NO:23;
(vi) SEQ ID NO:30, or a sequence having at least 90% similarity across the length of the sequence, or variant of SEQ ID NO:30;
(vii) SEQ ID NO:31, or a sequence having at least 90% similarity across the length of the sequence, or variant of SEQ ID NO:31;
(viii) SEQ ID NO:25, or a sequence having at least 90% similarity across the length of the sequence, or variant of SEQ ID NO:25.

Even more preferably, said RNA transcript is one or more of the transcripts characterised by the sequence of one of:
(i) SEQ ID NO:21, or a sequence having at least 90% similarity across the length of the sequence, or variant of SEQ ID NO:21;
(ii) SEQ ID NO:24, or a sequence having at least 90% similarity across the length of the sequence, or variant of SEQ ID NO:24;
(iii) SEQ ID NO:27, or a sequence having at least 90% similarity across the length of the sequence, or variant of SEQ ID NO:27;
(iv) SEQ ID NO:22, or a sequence having at least 90% similarity across the length of the sequence, or variant of SEQ ID NO:22.

Most preferably, said RNA transcript is characterised by SEQ ID NO:2.

In accordance with these aspects of the present invention, one may screen for the RNA transcript itself or for an expression product translated from said RNA transcript.

It should be understood that one may choose to screen for any one or more of said transcripts in a single sample of interest.

As detailed hereinbefore, hCG_1815491 has been determined to comprise 18 alternatively spliced exon segments which give rise to at least 11 RNA transcripts. It has now been determined that screening for the expression of one or more of the exon segments themselves is indicative of the neoplastic state of the individual in issue. It has still further been determined that the identification of certain combinations of these exons is particularly useful in this regard. To this end, it should be appreciated that the specific exon combinations which are hereinafter discussed may, in some RNA transcripts, have been spliced such that they are joined. In other transcripts, the subject exons may not be joined to one another but may be positioned, relative to one another, either proximally or distally along the transcript.

According to this embodiment there is therefore provided a method of screening for the onset or predisposition to the onset of a large intestine neoplasm in an individual, said method comprising measuring the level of expression of an RNA transcript, which transcript comprises one or more exon segments selected from:
(i) an exon segment defined by SEQ ID NO:2, or a sequence having at least 90% similarity across the length of the sequence, or variant of SEQ ID NO:2;
(ii) an exon segment defined by SEQ ID NO:3, or a sequence having at least 90% similarity across the length of the sequence, or variant of SEQ ID NO:3
(iii) an exon segment defined by SEQ ID NO:4, or a sequence having at least 90% similarity across the length of the sequence, or variant of SEQ ID NO:4;
(iv) an exon segment defined by SEQ ID NO:5, or a sequence having at least 90% similarity across the length of the sequence, or variant of SEQ ID NO:5;
(v) an exon segment defined by SEQ ID NO:6, or a sequence having at least 90% similarity across the length of the sequence, or variant of SEQ ID NO:6;
(vi) an exon segment defined by SEQ ID NO:7, or a sequence having at least 90% similarity across the length of the sequence, or variant of SEQ ID NO:7;
(vii) an exon segment defined by SEQ ID NO:8, or a sequence having at least 90% similarity across the length of the sequence, or variant of SEQ ID NO:8;
(viii) an exon segment defined by SEQ ID NO:9, or a sequence having at least 90% similarity across the length of the sequence, or variant of SEQ ID NO:9;
(ix) an exon segment defined by SEQ ID NO:10, or a sequence having at least 90% similarity across the length of the sequence, or variant of SEQ ID NO:10;
(x) an exon segment defined by SEQ ID NO:11, or a sequence having at least 90% similarity across the length of the sequence, or variant of SEQ ID NO:11;

(xi) an exon segment defined by SEQ ID NO:12, or a sequence having at least 90% similarity across the length of the sequence, or variant of SEQ ID NO:12 an exon segment defined by SEQ ID NO:13, or a sequence having at least 90% similarity across the length of the sequence, or variant of SEQ ID NO:13

(xiii) an exon segment defined by SEQ ID NO:14, or a sequence having at least 90% similarity across the length of the sequence, or variant of SEQ ID NO:14

(xiv) an exon segment defined by SEQ ID NO:15, or a sequence having at least 90% similarity across the length of the sequence, or variant of SEQ ID NO:15

(xv) an exon segment defined by SEQ ID NO:16, or a sequence having at least 90% similarity across the length of the sequence, or variant of SEQ ID NO:16

(xvi) an exon segment defined by SEQ ID NO:17, or a sequence having at least 90% similarity across the length of the sequence, or variant of SEQ ID NO:17

(xvii) an exon segment defined by SEQ ID NO:18, or a sequence having at least 90% similarity across the length of the sequence, or variant of SEQ ID NO:18

(xviii) an exon segment defined by SEQ ID NO:19, or a sequence having at least 90% similarity across the length of the sequence, or variant of SEQ ID NO:19; or (xix) an exon segment defined by SEQ ID NO:20, or a sequence having at least 90% similarity across the length of the sequence, or variant of SEQ ID NO:20 in a biological sample from said individual wherein a higher level of said RNA transcript or variant thereof relative to control levels is indicative of a neoplastic large intestine cell or a cell predisposed to the onset of a neoplastic state.

More particularly there is provided a method of screening for the onset or predisposition to the onset of a large intestine neoplasm in an individual, said method comprising measuring the level of expression of an RNA transcript, which transcript comprises one or more exon segments selected from:

(i) an exon segment defined by SEQ ID NO:3, or a sequence having at least 90% similarity across the length of the sequence, or variant of SEQ ID NO:3

(ii) an exon segment defined by SEQ ID NO:4, or a sequence having at least 90% similarity across the length of the sequence, or variant of SEQ ID NO:4;

(iii) an exon segment defined by SEQ ID NO:5, or a sequence having at least 90% similarity across the length of the sequence, or variant of SEQ ID NO:5;

(iv) an exon segment defined by SEQ ID NO:6, or a sequence having at least 90% similarity across the length of the sequence, or variant of SEQ ID NO:6;

(v) an exon segment defined by SEQ ID NO:7, or a sequence having at least 90% similarity across the length of the sequence, or variant of SEQ ID NO:7;

(vi) an exon segment defined by SEQ ID NO:8, or a sequence having at least 90% similarity across the length of the sequence, or variant of SEQ ID NO:8;

(v) an exon segment defined by SEQ ID NO:9, or a sequence having at least 90% similarity across the length of the sequence, or variant of SEQ ID NO:9; or (viii) an exon segment defined by SEQ ID NO:10, or a sequence having at least 90% similarity across the length of the sequence, or variant of SEQ ID NO:10;

(ix) an exon segment defined by SEQ ID NO:11, or a sequence having at least 90% similarity across the length of the sequence, or variant of SEQ ID NO:11;

(x) an exon segment defined by SEQ ID NO:12, or a sequence having at least 90% similarity across the length of the sequence, or variant of SEQ ID NO:12;

(xi) an exon segment defined by SEQ ID NO:13, or a sequence having at least 90% similarity across the length of the sequence, or variant of SEQ ID NO:13;

(xii) an exon segment defined by SEQ ID NO:14, or a sequence having at least 90% similarity across the length of the sequence, or variant of SEQ ID NO:14;

(xiii) an exon segment defined by SEQ ID NO:15, or a sequence having at least 90% similarity across the length of the sequence, or variant of SEQ ID NO:15;

(xiv) an exon segment defined by SEQ ID NO:18, or a sequence having at least 90% similarity across the length of the sequence, or variant of SEQ ID NO:18;

(xv) an exon segment defined by SEQ ID NO:19, or a sequence having at least 90% similarity across the length of the sequence, or variant of SEQ ID NO:19 in a biological sample from said individual wherein a higher level of said RNA transcript or variant thereof relative to control levels is indicative of a neoplastic large intestine cell or a cell predisposed to the onset of a neoplastic state.

Yet more particularly there is provided a method of screening for the onset or predisposition to the onset of a large intestine neoplasm in an individual, said method comprising measuring the level of expression of an RNA transcript selected from:

(i) an RNA transcript which comprises each of the exon segments defined by SEQ ID NO:5, SEQ ID NO:6, SEQ ID NO:10 and SEQ ID NO:12, or a sequence having at least 90% similarity across the length of these sequences, or variants of SEQ ID NO:5, SEQ ID NO:6, SEQ ID NO:10 and SEQ ID NO:12;

(ii) an RNA transcript which comprises each of the exon segments defined by SEQ ID NO:5, SEQ ID NO:6, SEQ ID NO:10 and SEQ ID NO:14, or a sequence having at least 90% similarity across the length of these sequences, or variants of SEQ ID NO:5, SEQ ID NO:6, SEQ ID NO:10 and SEQ ID NO:14;

(iii) an RNA transcript which comprises each of the exon segments defined by SEQ ID NO:3 and SEQ ID NO:6, or a sequence having at least 90% similarity across the length of these sequences, or variants of SEQ ID NO:3 and SEQ ID NO:6;

(iv) an RNA transcript which comprises each of the exon segments defined by SEQ ID NO:11, SEQ ID NO:12 and SEQ ID NO:18, or a sequence having at least 90% similarity across the length of these sequences, or variants of SEQ ID NO:11, SEQ ID NO:12 and SEQ ID NO:18;

(v) an RNA transcript which comprises each of the exon segments defined by SEQ ID NO:4 and SEQ ID NO:7, or a sequence having at least 90% similarity across the length of these sequences, or variants of SEQ ID NO:4 and SEQ ID NO:7;

(vi) an RNA transcript which comprises each of the exon segments defined by SEQ ID NO:6, SEQ ID NO:10 and SEQ ID NO:13, or a sequence having at least 90% similarity across the length of these sequences, or variants of SEQ ID NO:6, SEQ ID NO:10 and SEQ ID NO:13;

(vii) an RNA transcript which comprises each of the exon segments defined by SEQ ID NO:6 and SEQ ID NO:8, or a sequence having at least 90% similarity across the length of these sequences, or variants of SEQ ID NO:6 and SEQ ID NO:8;

(viii) an RNA transcript which comprises each of the exon segments defined by SEQ ID NO:19 and SEQ ID NO:18, or a sequence having at least 90% similarity across the length of these sequences, or variants of SEQ ID NO:19 and SEQ ID NO:18;

(ix) an RNA transcript which comprises each of the exon segments defined by SEQ ID NO:15 and SEQ ID NO:18, or a sequence having at least 90% similarity across the length of these sequences, or variants of SEQ ID NO:15 and SEQ ID NO:18;

(x) an RNA transcript which comprises each of the exon segments defined by SEQ ID NO:6 and SEQ ID NO:9, or a sequence having at least 90% similarity across the length of these sequences, or variants of SEQ ID NO:6 and SEQ ID NO:9; or (xi) an RNA transcript which comprises each of the exon segments defined by SEQ ID NO:4, SEQ ID NO:6, SEQ ID NO:10 and SEQ ID NO:12, or a sequence having at least 90% similarity across the length of these sequences, or variants of SEQ ID NO:4, SEQ ID NO:6, SEQ ID NO:10 and SEQ ID NO:12 in a biological sample from said individual wherein a higher level of said RNA transcript or variant thereof relative to control levels is indicative of a neoplastic large intestine cell or a cell predisposed to the onset of a neoplastic state.

In a further aspect there is provided a method of screening for the onset or predisposition to the onset of a large intestine neoplasm in an individual, said method comprising measuring the level of expression of an RNA transcript, which transcript comprises one or more exon segments selected from:

(i) an exon segment defined by SEQ ID NO:5, or a sequence having at least 90% similarity across the length of the sequence, or variant of SEQ ID NO:5;

(ii) an exon segment defined by SEQ ID NO:6, or a sequence having at least 90% similarity across the length of the sequence, or variant of SEQ ID NO:6;

(iii) an exon segment defined by SEQ ID NO:8, or a sequence having at least 90% similarity across the length of the sequence, or variant of SEQ ID NO:8;

(iv) an exon segment defined by SEQ ID NO:10, or a sequence having at least 90% similarity across the length of the sequence, or variant of SEQ ID NO:10;

(v) an exon segment defined by SEQ ID NO:11, or a sequence having at least 90% similarity across the length of the sequence, or variant of SEQ ID NO:11;

(vi) an exon segment defined by SEQ ID NO:12, or a sequence having at least 90% similarity across the length of the sequence, or variant of SEQ ID NO:12;

(vii) an exon segment defined by SEQ ID NO:14, or a sequence having at least 90% similarity across the length of the sequence, or variant of SEQ ID NO:14; or (viii) an exon segment defined by SEQ ID NO:18, or a sequence having at least 90% similarity across the length of the sequence, or variant of SEQ ID NO:18.

in a biological sample from said individual wherein a higher level of said RNA transcript or variant thereof relative to control levels is indicative of a neoplastic large intestine cell or a cell predisposed to the onset of a neoplastic state.

Still more particularly there is provided a method of screening for the onset or predisposition to the onset of a large intestine neoplasm in an individual, said method comprising measuring the level of expression of an RNA transcript, which transcript is selected from:

(i) an RNA transcript which comprises each of the exon segments defined by SEQ ID NO:5, SEQ ID NO:6, SEQ ID NO:10 and SEQ ID NO:12, or a sequence having at least 90% similarity across the length of these sequences, or variants of SEQ ID NO:5, SEQ ID NO:6, SEQ ID NO:10 and SEQ ID NO:12;

(ii) an RNA transcript which comprises each of the exon segments defined by SEQ ID NO:5, SEQ ID NO:6, SEQ ID NO:10 and SEQ ID NO:14, or a sequence having at least 90% similarity across the length of these sequences, or variants of SEQ ID NO:5, SEQ ID NO:6, SEQ ID NO:10 and SEQ ID NO:14;

(iii) an RNA transcript which comprises each of the exon segments defined by SEQ ID NO:11, SEQ ID NO:12, SEQ ID NO:18 and SEQ ID NO:24, or a sequence having at least 90% similarity across the length of these sequences, or variants of SEQ ID NO:11, SEQ ID NO:12, SEQ ID NO:18 and SEQ ID NO:24; or (iv) an RNA transcript which comprises each of the exon segments defined by SEQ ID NO:6 and SEQ ID NO:8, or a sequence having at least 90% similarity across the length of these sequences, or variants of SEQ ID NO:6 and SEQ ID NO:8.

in a biological sample from said individual wherein a higher level of said RNA transcript or variant thereof relative to control levels is indicative of a neoplastic large intestine cell or a cell predisposed to the onset of a neoplastic state.

In yet still another aspect, the exon segments of said transcripts are spliced such that they are joined.

With regard to the issue of sequence similarity (also referred to as "identity"), terms used to describe sequence relationships between two or more polynucleotides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (*Nucl. Acids Res.* 25: 3389, 1997). A detailed discussion of sequence analysis can be found in Unit 19.3 of Ausubel et al. ("Current Protocols in Molecular Biology" John Wiley & Sons Inc, Chapter 15, 1994-1998). A range of other algorithms may be used to compare the nucleotide and amino acid sequences such as but not limited to PILEUP, CLUSTALW, SEQUENCHER or VectorNTI.

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, is calculated by comparing two optimally aligned sequences over the window of comparison, determining the number of positions at which the identical nucleic acid base (e.g. A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

As detailed above, and more specifically, nucleic acid sequence identities (homologies) may be evaluated using any of the variety of sequence comparison algorithms and programs known in the art. The extent of sequence identity (homology) may be determined using any computer program and associated parameters, including those described herein, such as BLAST 2.2.2. or FASTA version 3.0t78, with the default parameters. For example, the sequence comparison algorithm is a BLAST version algorithm. In one aspect, for nucleic acid sequence identity analysis, the BLAST nucleotide parameters comprise word size=11, expect=10, filter low complexity with DUST, cost to open gap=5, cost to extend gap=2, penalty for mismatch=−3, reward for match=1, Dropoff (X) for BLAST extensions in bits=20, final X dropoff value for gapped alignment=50, and all other options are set to default.

Exemplary algorithms and programs include, but are not limited to, TBLASTN, BLASTP, FASTA, TFASTA, and CLUSTALW (Pearson and Lipman, *Proc. Natl. Acad. Sci. USA* 85(8):2444-2448, 1988; Altschul et al., *J. Mol. Biol.* 215(3):403-410, 1990; Thompson et al., *Nucleic Acids Res.* 22(2):4673-4680, 1994; Higgins et al., *Methods Enzymol.* 266:383-402, 1996; Altschul et al., *Nature Genetics* 3:266-272, 1993). Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications.

BLAST, BLAST 2.0 and BLAST 2.2.2 algorithms are also used to practice the invention. They are described, e.g., in; Altschul et al. (1990), supra. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al. (1990) supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. The BLAST algorithm also performs a statistical analysis of the similarity between two sequences (see, e.g., Karlin & Altschul (1993) *Proc. Natl. Acad. Sci. USA* 90:5873). One measure of similarity provided by BLAST algorithm is the smallest sum probability (P(N)), which provides an indication of the probability by which a match between two nucleotide sequences would occur by chance.

The subject sequences are defined as exhibiting at least 90% similarity. In one embodiment, said percentage similarity is 91%, 92%, 93%, 94%, 95%, 96%, 97%, 98% or 99%.

It should be understood that the "individual" who is the subject of testing may be any human or non-human mammal. Examples of non-human mammals includes primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. deer, foxes). Preferably the mammal is a human.

The method of the present invention is predicated on the comparison of the level of hCG_1815491 in a biological sample with the control levels of this marker. The "control level" may be either a "normal level", which is the level of marker expressed by a corresponding large intestine cell or cellular population which is not neoplastic, or the background level which is detectable in a negative control sample.

The normal (or "non-neoplastic") level may be determined using tissues derived from the same individual who is the subject of testing. However, it would be appreciated that this may be quite invasive for the individual concerned and it is therefore likely to be more convenient to analyse the test results relative to a standard result which reflects individual or collective results obtained from individuals other than the patient in issue. This latter form of analysis is in fact the preferred method of analysis since it enables the design of kits which require the collection and analysis of a single biological sample, being a test sample of interest. The standard results which provide the normal level may be calculated by any suitable means which would be well known to the person of skill in the art. For example, a population of normal tissues can be assessed in terms of the level of the neoplastic marker of the present invention, thereby providing a standard value or range of values against which all future test samples are analysed. It should also be understood that the normal level may be determined from the subjects of a specific cohort and for use with respect to test samples derived from that cohort. Accordingly, there may be determined a number of standard values or ranges which correspond to cohorts which differ in respect of characteristics such as age, gender, ethnicity or health status. Said "normal level" may be a discrete level or a range of levels. An increase in the expression level of the subject genes relative to normal levels is indicative of the tissue being neoplastic.

Preferably, said control level is a non-neoplastic level.

According to these aspects of the present invention, said large intestine tissue is preferably colorectal tissue.

Still more preferably, said neoplasm is a colorectal adenoma or adenocarcinoma.

In a related aspect, it has been determined that a sub-population of the hCG_1815491 markers are not only expressed at levels higher than normal levels, their expression pattern is uniquely characterised by the fact that expression levels above that of background control levels are not detectable in non-neoplastic tissue. This determination has therefore enabled the development of qualitative screening systems which are simply designed to detect hCG_1815491 expression relative to a control background level. In accordance with this aspect of the present invention, said "control level" is therefore the "background level". Preferably, said background level is of the chosen testing methodology.

According to this aspect, there is therefore provided a method of screening for the onset or predisposition to the onset of a large intestine neoplasm in an individual, said method comprising measuring the level of expression of one or more RNA transcripts, which transcripts comprise an RNA sequence characterised by the sequence of one of:
(i) SEQ ID NO:21 or a sequence having at least 90% similarity across the length of the sequence, or variant of SEQ ID NO:21;
(ii) SEQ ID NO:24 or a sequence having at least 90% similarity across the length of the sequence, or variant of SEQ ID NO:24;
(iii) SEQ ID NO:25 or a sequence having at least 90% similarity across the length of the sequence, or variant of SEQ ID NO:25;
(iv) SEQ ID NO:26 or a sequence having at least 90% similarity across the length of the sequence, or variant of SEQ ID NO:26;
(v) SEQ ID NO:27 or a sequence having at least 90% similarity across the length of the sequence, or variant of SEQ ID NO:27;
(vi) SEQ ID NO:29 or a sequence having at least 90% similarity across the length of the sequence, or variant of SEQ ID NO:29;
(vii) SEQ ID NO:30 or a sequence having at least 90% similarity across the length of the sequence, or variant of SEQ ID NO:30; or
(viii) SEQ ID NO:31 or a sequence having at least 90% similarity across the length of the sequence, or variant of SEQ ID NO:31;
in a biological sample from said individual wherein a higher level of expression of the genes or transcripts of group (i) and/or group (ii) relative to background levels is indicative of a neoplastic cell or a cell predisposed to the onset of a neoplastic state.

In a most preferred embodiment, said transcripts comprise an RNA sequence characterised by the sequence of one of:
(i) SEQ ID NO:21 or a sequence having at least 90% similarity across the length of the sequence, or variant of SEQ ID NO:21;
(ii) SEQ ID NO:22 or a sequence having at least 90% similarity across the length of the sequence, or variant of SEQ ID NO:22;
(iii) SEQ ID NO:23 or a sequence having at least 90% similarity across the length of the sequence, or variant of SEQ ID NO:23;
(iv) SEQ ID NO:24 or a sequence having at least 90% similarity across the length of the sequence, or variant of SEQ ID NO:24; or
(v) SEQ ID NO:27 or a sequence having at least 90% similarity across the length of the sequence, or variant of SEQ ID NO:27;
in a biological sample from said individual wherein a higher level of expression of the genes or transcripts of group (i) and/or group (ii) relative to background levels is indicative of a neoplastic cell or a cell predisposed to the onset of a neoplastic state.

Most preferably, said RNA sequences are characterised by the sequence of either SEQ ID NO:21 or SEQ ID NO:22.

The detection method of the present invention can be performed on any suitable biological sample. To this end, reference to a "biological sample" should be understood as a reference to any sample of biological material derived from an animal such as, but not limited to, cellular material, biological fluids (eg. blood), faeces, tissue biopsy specimens, surgical specimens or fluid which has been introduced into the body of an animal and subsequently removed (such as, for example, the solution retrieved from an enema wash). The biological sample which is tested according to the method of the present invention may be tested directly or may require some form of treatment prior to testing. For example, a biopsy or surgical sample may require homogenisation prior to testing or it may require sectioning for in situ testing of the qualitative expression levels of individual genes. Alternatively, a cell sample may require permeabilisation prior to testing. Further, to the extent that the biological sample is not in liquid form, (if such form is required for testing) it may require the addition of a reagent, such as a buffer, to mobilise the sample.

To the extent that the neoplastic marker gene expression product is present in a biological sample, the biological sample may be directly tested or else all or some of the nucleic acid or protein material present in the biological sample may be isolated prior to testing. To this end, and as hereinbefore described, it would be appreciated that when screening for changes to the level of expression of hCG_1815491 or the specifically recited transcripts, one may screen for the RNA transcripts themselves, cDNA which has been transcribed therefrom or a translated protein product. In yet another example, the sample may be partially purified or otherwise enriched prior to analysis. For example, to the extent that a biological sample comprises a very diverse cell population, it may be desirable to enrich for a sub-population of particular interest. It is within the scope of the present invention for the target cell population or molecules derived therefrom to be pretreated prior to testing, for example, inactivation of live virus or being run on a gel. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation. Preferably, said sample is a faecal (stool) sample, enema wash, surgical resection, tissue biopsy or blood sample.

As detailed hereinbefore, the present invention is designed to screen for a neoplastic cell or cellular population, which is located in the large intestine. Accordingly, reference to "cell or cellular population" should be understood as a reference to an individual cell or a group of cells. Said group of cells may be a diffuse population of cells, a cell suspension, an encapsulated population of cells or a population of cells which take the form of tissue.

As detailed hereinbefore, reference to "expression" should be understood as a reference to the transcription and/or translation of a nucleic acid molecule. In this regard, the present invention is exemplified with respect to screening for hCG_1815491 expression products taking the form of RNA transcripts (eg primary RNA or mRNA). Reference to "RNA" should be understood to encompass reference to any form of RNA, such as primary RNA or mRNA. Without limiting the present invention in any way, the modulation of gene transcription leading to increased or decreased RNA synthesis will also correlate with the translation of some of these RNA transcripts to produce a protein product. Accordingly, the present invention also extends to detection methodology which is directed to screening for modulated levels or patterns of the neoplastic marker protein products as an indicator of the neoplastic state of a cell or cellular population. Although one method is to screen for RNA transcripts and/or the corresponding protein product, it should be understood that the present invention is not limited in this regard and extends to screening for any other form of neoplastic marker expression product such as, for example, a primary RNA transcript. It is well within the skill of the person of skill in the art to determine the most appropriate screening target for any given situation.

Reference to "nucleic acid molecule" should be understood as a reference to both deoxyribonucleic acid molecules and ribonucleic acid molecules and fragments thereof. The present invention therefore extends to both directly screening for RNA levels in a biological sample or screening for the complementary cDNA which has been reverse-transcribed from an RNA population of interest. It is well within the skill of the person of skill in the art to design methodology directed to screening for either DNA or RNA. As detailed above, the method of the present invention also extends to screening for the protein product translated from the subject RNA.

In terms of screening for the upregulation of hCG_1815491 it would also be well known to the person of skill in the art that changes which are detectable at the DNA level are indicative of changes to gene expression activity and therefore changes to expression product levels. Such changes include but are not limited to, changes to DNA methylation and chromatin proteins associated with the gene. Accordingly, reference herein to "screening the level of expression" and comparison of these "levels of expression" to control "levels of expression" should be understood as a reference to assessing DNA factors which are related to transcription, such as gene/DNA methylation patterns or association with specific chromosomal proteins.

The term "protein" should be understood to encompass peptides, polypeptides and proteins (including protein fragments). The protein may be glycosylated or unglycosylated and/or may contain a range of other molecules fused, linked, bound or otherwise associated to the protein such as amino acids, lipids, carbohydrates or other peptides, polypeptides or proteins. Reference herein to a "protein" includes a protein comprising a sequence of amino acids as well as a protein associated with other molecules such as amino acids, lipids, carbohydrates or other peptides, polypeptides or proteins.

The proteins encoded by hCG_1815491 may be in multimeric form meaning that two or more molecules are associated together. Where the same protein molecules are associated together, the complex is a homomultimer. An example of a homomultimer is a homodimer. Where at least one marker protein is associated with at least one non-marker protein, then the complex is a heteromultimer such as a heterodimer.

Reference to a "fragment" should be understood as a reference to a portion of the subject nucleic acid molecule or protein. As detailed hereinbefore, this is particularly relevant with respect to screening for modulated RNA levels in stool samples since the subject RNA is likely to have been degraded or otherwise fragmented due to the environment of the gut. One may therefore actually be detecting fragments of the subject RNA molecule, which fragments are identified by virtue of the use of a suitably specific probe.

Reference to the "onset" of a neoplasm, such as adenoma or adenocarcinoma, should be understood as a reference to one or more cells of that individual exhibiting dysplasia. In this regard, the adenoma or adenocarcinoma may be well developed in that a mass of dysplastic cells has developed. Alternatively, the adenoma or adenocarcinoma may be at a very early stage in that only relatively few abnormal cell divisions have occurred at the time of diagnosis. The present invention also extends to the assessment of an individual's predisposition to the development of a neoplasm, such as an adenoma or adenocarcinoma. Without limiting the present invention in any way, changed levels of the neoplastic marker may be indicative of that individual's predisposition to developing a neoplasia, such as the future development of an adenoma or adenocarcinoma or another adenoma or adenocarcinoma.

Although the preferred method is to diagnose neoplasia development or predisposition thereto, the detection of converse changes in the levels of said marker may be desired under certain circumstances, for example, to monitor the effectiveness of therapeutic or prophylactic treatment directed to modulating a neoplastic condition, such as adenoma or adenocarcinoma development. For example, where elevated levels of hCG_1815491 indicates that an individual has developed a condition characterised by adenoma or adenocarcinoma development, for example, screening for a decrease in the levels of this marker subsequently to the onset of a therapeutic regime may be utilised to indicate reversal or other form of improvement of the subject individual's condition.

The method of the present invention is therefore useful as a one off test or as an on-going monitor of those individuals thought to be at risk of neoplasia development or as a monitor of the effectiveness of therapeutic or prophylactic treatment regimes directed to inhibiting or otherwise slowing neoplasia development. In these situations, mapping the modulation of hCG_1815491 expression levels in any one or more classes of biological samples is a valuable indicator of the status of an individual or the effectiveness of a therapeutic or prophylactic regime which is currently in use. Accordingly, the method of the present invention should be understood to extend to monitoring for increases or decreases in hCG_1815491 expression levels in an individual relative to their normal level (as hereinbefore defined), or relative to one or more earlier marker expression levels determined from a biological sample of said individual.

Means of testing for the subject expressed neoplasm marker in a biological sample can be achieved by any suitable method, which would be well known to the person of skill in the art, such as but not limited to:

(i) In vivo detection.

Molecular Imaging may be used following administration of imaging probes or reagents capable of disclosing altered expression of the marker in the intestinal tissues.

Molecular imaging (Moore et al., *BBA*, 1402:239-249, 1988; Weissleder et al., *Nature Medicine* 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy.

(ii) Detection of up-regulation of RNA expression in the cells by Fluorescent In Situ Hybridization (FISH), or in extracts from the cells by technologies such as Quantitative Reverse Transcriptase Polymerase Chain Reaction (QRTPCR) or Flow cytometric qualification of competitive RT-PCR products (Wedemeyer et al., *Clinical Chemistry* 48:9 1398-1405, 2002).

(iii) Assessment of expression profiles of RNA, for example by array technologies (Alon et al., *Proc. Natl. Acad. Sci. USA:* 96, 6745-6750, June 1999).

A "microarray" is a linear or multi-dimensional array of preferably discrete regions, each having a defined area, formed on the surface of a solid support. The density of the discrete regions on a microarray is determined by the total numbers of target polynucleotides to be detected on the surface of a single solid phase support. As used herein, a DNA microarray is an array of oligonucleotide probes placed onto a chip or other surfaces used to detect complementary oligonucleotides from a complex nucleic acid mixture. Since the position of each particular group of probes in the array is known, the identities of the target polynucleotides can be determined based on their binding to a particular position in the microarray.

Recent developments in DNA microarray technology make it possible to conduct a large scale assay of a plurality of target nucleic acid molecules on a single solid phase support. U.S. Pat. No. 5,837,832 (Chee et al.) and related patent applications describe immobilizing an array of oligonucleotide probes for hybridization and detection of specific nucleic acid sequences in a sample. Target polynucleotides of interest isolated from a tissue of interest are hybridized to the DNA chip and the specific sequences detected based on the target polynucleotides' preference and degree of hybridization at discrete probe locations. One important use of arrays is in the analysis of differential gene expression, where the profile of expression of genes in different cells or tissues, often a tissue of interest and a control tissue, is compared and any differences in gene expression among the respective tissues are identified. Such information is useful for the identification of the types of genes expressed in a particular tissue type and diagnosis of conditions based on the expression profile.

In one example, RNA from the sample of interest is subjected to reverse transcription to obtain labelled cDNA. See U.S. Pat. No. 6,410,229 (Lockhart et al.)

The cDNA is then hybridized to oligonucleotides or cDNAs of known sequence arrayed on a chip or other surface in a known order. In another example, the RNA is isolated from a biological sample and hybridised to a chip on which are anchored cDNA probes. The location of the oligonucleotide to which the labelled cDNA hybridizes provides sequence information on the cDNA, while the amount of labelled hybridized RNA or cDNA provides an estimate of the relative representation of the RNA or cDNA of interest. See Schena, et al. *Science* 270:467-470 (1995). For example, use of a cDNA microarray to analyze gene expression patterns in human cancer is described by DeRisi, et al. (*Nature Genetics* 14:457-460 (1996)).

In a preferred embodiment, nucleic acid probes corresponding to the subject nucleic acids are made. The nucleic acid probes attached to the microarray are designed to be substantially complementary to the nucleic acids of the biological sample such that specific hybridization of the target sequence and the probes of the present invention occurs. This complementarity need not be perfect, in that there may be any number of base pair mismatches that will interfere with hybridization between the target sequence and the single stranded nucleic acids of the present invention. It is expected that the overall homology of the genes at the nucleotide level probably will be about 40% or greater, probably about 60% or greater, and even more probably about 80% or greater; and in addition that there will be corresponding contiguous sequences of about 8-12 nucleotides or longer. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions.

A nucleic acid probe is generally single stranded but can be partly single and partly double stranded. The strandedness of the probe is dictated by the structure, composition, and properties of the target sequence. In general, the oligonucleotide probes range from about 6, 8, 10, 12, 15, 20, 30 to about 100 bases long, with from about 10 to about 80 bases being preferred, and from about 15 to about 40 bases being particularly preferred. That is, generally entire genes are rarely used as probes. In some embodiments, much longer nucleic acids can be used, up to hundreds of bases. The probes are sufficiently specific to hybridize to a complementary template sequence under conditions known by those of skill in the art. The number of mismatches between the probe's sequences and their complementary template (target) sequences to which they hybridize during hybridization generally do not exceed 15%, usually do not exceed 10% and preferably do not exceed 5%, as-determined by BLAST (default settings).

Oligonucleotide probes can include the naturally-occurring heterocyclic bases normally found in nucleic acids (uracil, cytosine, thymine, adenine and guanine), as well as modified bases and base analogues. Any modified base or base analogue compatible with hybridization of the probe to a target sequence is useful in the practice of the invention. The sugar or glycoside portion of the probe can comprise deoxyribose, ribose, and/or modified forms of these sugars, such as, for example, 2'-O-alkyl ribose. In a preferred embodiment, the sugar moiety is 2'-deoxyribose; however, any sugar moiety that is compatible with the ability of the probe to hybridize to a target sequence can be used.

In one embodiment, the nucleoside units of the probe are linked by a phosphodiester backbone, as is well known in the art. In additional embodiments, internucleotide linkages can include any linkage known to one of skill in the art that is compatible with specific hybridization of the probe including, but not limited to phosphorothioate, methylphosphonate, sulfamate (e.g., U.S. Pat. No. 5,470,967) and polyamide (i.e., peptide nucleic acids). Peptide nucleic acids are described in Nielsen et al. (1991) *Science* 254: 1497-1500, U.S. Pat. No. 5,714,331, and Nielsen (1999) *Curr. Opin. Biotechnol.* 10:71-75.

In certain embodiments, the probe can be a chimeric molecule; i.e., can comprise more than one type of base or sugar subunit, and/or the linkages can be of more than one type within the same primer. The probe can comprise a moiety to facilitate hybridization to its target sequence, as are known in the art, for example, intercalators and/or minor groove binders. Variations of the bases, sugars, and internucleoside backbone, as well as the presence of any pendant group on the probe, will be compatible with the ability of the probe to bind, in a sequence-specific fashion, with its target sequence. A large number of structural modifications, are possible within these bounds. Advantageously, the probes according to the present invention may have structural characteristics such that they allow the signal amplification, such structural characteristics being, for example, branched DNA probes as those described by Urdea et al. (*Nucleic Acids Symp. Ser.*, 24:197-200 (1991)) or in the European Patent No. EP-0225,807. Moreover, synthetic methods for preparing the various heterocyclic bases, sugars, nucleosides and nucleotides that form the probe, and preparation of oligonucleotides of specific predetermined sequence, are well-developed and known in the art. A preferred method for oligonucleotide synthesis incorporates the teaching of U.S. Pat. No. 5,419,966.

Multiple probes may be designed for a particular target nucleic acid to account for polymorphism and/or secondary structure in the target nucleic acid, redundancy of data and the like. In some embodiments, where more than one probe per sequence is used, either overlapping probes or probes to different sections of a single target gene are used. That is, two, three, four or more probes, are used to build in a redundancy for a particular target. The probes can be overlapping (i.e. have some sequence in common), or are specific for distinct sequences of a gene. When multiple target polynucleotides are to be detected according to the present invention, each probe or probe group corresponding to a particular target polynucleotide is situated in a discrete area of the microarray.

Probes may be in solution, such as in wells or on the surface of a micro-array, or attached to a solid support. Examples of solid support materials that can be used include a plastic, a ceramic, a metal, a resin, a gel and a membrane. Useful types of solid supports include plates, beads, magnetic material, microbeads, hybridization chips, membranes, crystals, ceramics and self-assembling monolayers. One example comprises a two-dimensional or three-dimensional matrix, such as a gel or hybridization chip with multiple probe binding sites (Pevzner et al., *J. Biomol. Struc. & Dyn.* 9:399-410, 1991; Maskos and Southern, *Nuc. Acids Res.* 20:1679-84, 1992). Hybridization chips can be used to construct very large probe arrays that are subsequently hybridized with a target nucleic acid. Analysis of the hybridization pattern of the chip can assist in the identification of the target nucleotide sequence. Patterns can be manually or computer analyzed, but it is clear that positional sequencing by hybridization lends itself to computer analysis and automation. In another example, one may use an Affymetrix chip on a solid phase structural support in combination with a fluorescent bead based approach. In yet another example, one may utilise a cDNA microarray. In this regard, the oligonucleotides described by Lockkart et al. (i.e. Affymetrix synthesis probes in situ on the solid phase) are particularly preferred, that is, photolithography.

As will be appreciated by those in the art, nucleic acids can be attached or immobilized to a solid support in a wide variety of ways. By "immobilized" herein is meant the association or binding between the nucleic acid probe and the solid support is sufficient to be stable under the conditions of binding, washing, analysis, and removal. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as streptavidin, to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

Nucleic acid probes may be attached to the solid support by covalent binding such as by conjugation with a coupling agent or by covalent or non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (T. Sano and C. R. Cantor, *Bio/Technology* 9:1378-81 (1991)), or derivatives or combinations of these agents. Nucleic acids may be attached to the solid support by a photocleavable bond, an electrostatic bond, a disulfide bond, a peptide bond, a diester bond or a combination of these sorts of bonds. The array may also be attached to the solid support by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

In general, the probes are attached to the microarray in a wide variety of ways, as will be appreciated by those in the art. As described herein, the nucleic acids can either be synthesized first, with subsequent attachment to the microarray, or can be directly synthesized on the microarray.

The microarray comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. The solid phase support of the present invention can be of any solid materials and structures suitable for supporting nucleotide hybridization and synthesis. Preferably, the solid phase support comprises at least one substantially rigid surface on which the oligonucleotide primers can be immobilized and the reverse transcriptase reaction performed. The substrates with which the polynucleotide microarray elements are stably associated and may be fabricated from a variety of materials, including plastics, ceramics, metals, acrylamide, cellulose, nitrocellulose, glass, polystyrene, polyethylene vinyl acetate, polypropylene, polymethacrylate, polyethylene, polyethylene oxide, polysilicates, polycarbonates, Teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates may be two-dimensional or three-dimensional in form, such as gels, membranes, thin films, glasses, plates, cylinders, beads, magnetic beads, optical fibers, woven fibers, etc. A preferred form of array is a three-dimensional array. A preferred three-dimensional array is a collection of tagged beads. Each tagged bead has different oligonucleotide primers attached to it. Tags are detectable by signalling means such as color (Luminex, Illumina) and electromagnetic field (Phannaseq) and signals on tagged beads can even be remotely detected (e.g., using optical fibers). The size of the solid support can be any of the standard microarray sizes, useful for DNA microarray technology, and the size may be tailored to fit the particular machine being used to conduct a reaction of the invention. In general, the substrates allow optical detection and do not appreciably fluoresce.

In one embodiment, the surface of the microarray and the probe may be derivatized with chemical functional groups for subsequent attachment of the two. Thus, for example, the microarray is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known. In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside. In an additional embodiment, the immobilization to the solid support may be very strong, yet non-covalent. For example, biotinylated oligonucleotides can be made, which bind to surfaces covalently coated with streptavidin, resulting in attachment.

The arrays may be produced according to any convenient methodology, such as preforming the polynucleotide microarray elements and then stably associating them with the surface. Alternatively, the oligonucleotides may be synthesized on the surface, as is known in the art. A number of different array configurations and methods for their production are known to those of skill in the art and disclosed in WO 95/25116 and WO 95/35505 (photolithographic techniques), U.S. Pat. No. 5,445,934 (in situ synthesis by photolithography), U.S. Pat. No. 5,384,261 (in situ synthesis by mechanically directed flow paths); and U.S. Pat. No. 5,700,637 (synthesis by spotting, printing or coupling); the disclosure of which are herein incorporated in their entirety by reference. Another method for coupling DNA to beads uses specific ligands attached to the end of the DNA to link to ligand-binding molecules attached to a bead. Possible ligand-binding partner pairs include biotin-avidin/streptavidin, or various antibody/antigen pairs such as digoxygenin-antidigoxygenin antibody (Smith et al., *Science* 258:1122-1126 (1992)). Covalent chemical attachment of DNA to the support can be accomplished by using standard coupling agents to link the 5'-phosphate on the DNA to coated microspheres through a phosphoamidate bond. Methods for immobilization of oligonucleotides to solid-state substrates are well established. See Pease et al., *Proc. Natl. Acad. Sci. USA* 91(11):5022-5026 (1994). A preferred method of attaching oligonucleotides to solid-state substrates is described by Guo et al., *Nucleic Acids Res.* 22:5456-5465 (1994). Immobilization can be accomplished either by in situ DNA synthesis (Maskos and Southern, supra) or by covalent attachment of chemically synthesized oligonucleotides (Guo et al., supra) in combination with robotic arraying technologies.

In addition to the solid-phase technology represented by microarray arrays, gene expression can also be quantified using liquid-phase assays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR® Green 1, is an example of an intercalating dye, that preferentially binds to dsDNA resulting in a concomitant increase in the fluorescent signal. Sequence specific probes, such as used with TaqMan technology, consist of a fluorochrome and a quenching molecule covalently bound to opposite ends of an oligonucleotide. The probe is designed to selectively bind the target DNA sequence between the two oligonucleotide primers. When the DNA strands are synthesized during the PCR reaction, the fluorochrome is cleaved from the probe by the exonuclease activity of the polymerase resulting in signal dequenching. The probe signalling method can be more specific than the intercalating dye method, but in each case, signal strength is proportional to the dsDNA product produced. Each type of quantification method can be used in multi-well liquid phase arrays with each well representing oligonucleotide primers and/or probes specific to nucleic acid sequences of interest. When used with messenger RNA preparations of tissues or cell lines, an array of probe/primer reactions can simultaneously quantify the expression of multiple gene products of interest. See Germer et al., *Genome Res.* 10:258-266 (2000); Heid et al., *Genome Res.* 6:986-994 (1996).

(iv) Measurement of altered neoplastic marker protein levels in cell extracts, for example by immunoassay.

Testing for proteinaceous neoplastic marker expression product in a biological sample can be performed by any one of a number of suitable methods which are well known to those skilled in the art. Examples of suitable methods include, but are not limited to, antibody based screening of tissue sections, biopsy specimens or bodily fluid samples.

To the extent that antibody based methods of diagnosis are used, the presence of the marker protein may be determined in a number of ways such as by Western blotting, ELISA or flow cytometry procedures. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for the marker or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking, covalently binding or physically adsorbing, the polymer-antibody complex is washed in preparation for the test sample. An aliquot of the sample to be tested is then added to the solid phase complex and incubated for a period of time sufficient (e.g. 2-40 minutes) and under suitable conditions (e.g. 25° C.) to allow binding of any subunit present in the antibody. Following the incubation period, the antibody subunit solid phase is washed and dried and incubated with a second antibody specific for a portion of the antigen. The second antibody is linked to a reporter molecule which is used to indicate the binding of the second antibody to the antigen.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

(v) Without limiting the present invention to any one theory or mode of action, during development gene expression is regulated by processes that alter the availability of genes for expression in different cell lineages without any alteration in gene sequence, and these states can be inherited through a cell division—a process called epigenetic inheritance. Epigenetic inheritance is determined by a combination of DNA methylation (modification of cytosine to give 5-methyl cytosine, 5meC) and by modifications of the histone chromosomal proteins that package DNA. Thus methylation of DNA at CpG sites and modifications such as deacetylation of histone H3 on lysine 9, and methylation on lysine 9 or 27 are associated with inactive chromatin, while the converse state of a lack of DNA methylation, acetylation of lysine 9 of histone H3 is associated with open chromatin and active gene expression. In cancer, this epigenetic regulation of gene expression is frequently found to be disrupted (Esteller & Herman, 2000; Jones & Baylin, 2002). Genes such as tumour suppressor or metastasis suppressor genes are often found to be silenced by DNA methylation, while other genes may be hypomethylated and inappropriately expressed. Thus, among genes that elevated or inappropriate expression in cancer, this in some instances is characterised by a loss of methylation of the promoter or regulatory region of the gene.

A variety of methods are available for detection of aberrantly methylated DNA of a specific gene, even in the presence of a large excess of normal DNA (Clark 2007). Thus, elevated expression of certain genes may be detected through detection of the presence of hypomethylated sequences in tissue, bodily fluid or other patient samples.

Epigenetic alterations and chromatin changes in cancer are also evident in the altered association of modified histones with specific genes (Esteller, 2007); for example activated genes are often found associated with histone H3 that is acetylated on lysine 9 and methylated on lysine 4. The use of antibodies targeted to altered histones allows for the isolation of DNA associated with particular chromatin states and has potential use in cancer diagnosis.

(vi) Determining altered expression of protein neoplastic markers on the cell surface, for example by immunohistochemistry.

(vii) Determining altered protein expression based on any suitable functional test, enzymatic test or immunological test in addition to those detailed in points (iv) and (v) above.

A person of ordinary skill in the art could determine, as a matter of routine procedure, the appropriateness of applying a given method to a particular type of biological sample.

Without limiting the present invention in any way, and as detailed above, gene expression levels can be measured by a variety of methods known in the art. For example, gene transcription or translation products can be measured. Gene transcription products, i.e., RNA, can be measured, for example, by hybridization assays, run-off assays, Northern blots, or other methods known in the art.

Hybridization assays generally involve the use of oligonucleotide probes that hybridize to the single-stranded RNA transcription products. Thus, the oligonucleotide probes are complementary to the transcribed RNA expression product. Typically, a sequence-specific probe can be directed to hybridize to RNA or cDNA. A "nucleic acid probe", as used herein, can be a DNA probe or an RNA probe that hybridizes to a complementary sequence. One of skill in the art would know how to design such a probe such that sequence specific hybridization will occur. One of skill in the art will further know how to quantify the amount of sequence specific hybridization as a measure of the amount of gene expression for the gene was transcribed to produce the specific RNA.

The hybridization sample is maintained under conditions that are sufficient to allow specific hybridization of the nucleic acid probe to a specific gene expression product. "Specific hybridization", as used herein, indicates near exact hybridization (e.g., with few if any mismatches). Specific hybridization can be performed under high stringency conditions or moderate stringency conditions. In one embodiment, the hybridization conditions for specific hybridization are high stringency. For example, certain high stringency conditions can be used to distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in Current Protocols in Molecular Biology (Ausubel et al., 1998 supra), the entire teachings of which are incorporated by reference herein). The exact conditions that determine the stringency of hybridization depend not only on ionic strength (e.g., 0.2.times.SSC, 0.1.times.SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another. By varying hybridization conditions from a level of stringency at which no hybridization occurs to a level at which hybridization is first observed, conditions that will allow a given sequence to hybridize (e.g., selectively) with the most complementary sequences in the sample can be determined.

Exemplary conditions that describe the determination of wash conditions for moderate or low stringency conditions are described in Kraus, M. and Aaronson, S., 1991. *Methods Enzymol.*, 200:546-556; and in, Ausubel et al. 1998, supra)). Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum mismatch percentage among the sequences that hybridize. Generally, doubling the concentration of SSC results in an increase in $T_m$ of about 17° C. Using these guidelines, the wash temperature can be determined empirically for high, moderate or low stringency, depending on the level of mismatch sought. For example, a low stringency wash can comprise washing in a solution containing 0.2.times.SSC/0.1% SDS for 10 minutes at room temperature; a moderate stringency wash can comprise washing in a pre-warmed solution (42° C.) solution containing 0.2.times.SSC/0.1% SDS for 15 minutes at 42° C.; and a high stringency wash can comprise washing in pre-warmed (68° C.) solution containing 0.1.times.SSC/0.1% SDS for 15 minutes at 68° C. Furthermore, washes can be performed repeatedly or sequentially to obtain a desired result as known in the art. Equivalent conditions can be determined by varying one or more of the parameters given as an example, as known in the art, while maintaining a similar degree of complementarity between the target nucleic acid molecule and the primer or probe used (e.g., the sequence to be hybridized).

A related aspect of the present invention provides a molecular array, which array comprises a plurality of:
(i) nucleic acid molecules comprising a nucleotide sequence corresponding to any one or more of the neoplastic marker sequences hereinbefore described or a sequence exhibiting at least 80% identity thereto or a functional derivative, fragment, variant or homologue of said nucleic acid molecule; or
(ii) nucleic acid molecules comprising a nucleotide sequence capable of hybridising to any one or more of the sequences of (i) under medium stringency conditions or a functional derivative, fragment, variant or homologue of said nucleic acid molecule; or
(iii) nucleic acid probes or oligonucleotides comprising a nucleotide sequence capable of hybridising to any one or more of the sequences of (i) under medium stringency conditions or a functional derivative, fragment, variant or homologue of said nucleic acid molecule; or
(iv) probes capable of binding to any one or more of the proteins encoded by the nucleic acid molecules of (i) or a derivative, fragment or, homologue thereof
wherein the level of expression of said marker genes of (i) or proteins of (iv) is indicative of the neoplastic state of a cell or cellular subpopulation derived from the large intestine.

Preferably, said percent identity is at least 85%, 90%, 91%, 92%, 93%, 94%, 95%, 96%, 97%, 98% or 99%.

Low stringency includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. In general, washing is carried out at $T_m = 69.3 + 0.41$ (G+C) % [19] = $-12°$ C. However, the $T_m$ of a duplex DNA decreases by $1°$ C. with every increase of 1% in the number of mismatched based pairs (Bonner et al (1973) *J. Mol. Biol.* 81:123).

Preferably, the subject probes are designed to bind to the nucleic acid or protein to which they are directed with a level of specificity which minimises the incidence of non-specific reactivity. However, it would be appreciated that it may not be possible to eliminate all potential cross-reactivity or non-specific reactivity, this being an inherent limitation of any probe based system.

In terms of the probes which are used to detect the subject proteins, they may take any suitable form including antibodies and aptamers.

A library or array of nucleic acid or protein probes provides rich and highly valuable information. Further, two or more arrays or profiles (information obtained from use of an array) of such sequences are useful tools for comparing a test set of results with a reference, such as another sample or stored calibrator. In using an array, individual probes typically are immobilized at separate locations and allowed to react for binding reactions. Oligonucleotide primers associated with assembled sets of markers are useful for either preparing libraries of sequences or directly detecting markers from other biological samples.

A library (or array, when referring to physically separated nucleic acids corresponding to at least some sequences in a library) of hCG_1815491 markers exhibits highly desirable properties. These properties are associated with specific conditions, and may be characterized as regulatory profiles. A profile, as termed here refers to a set of members that provides diagnostic information of the tissue from which the markers were originally derived. A profile in many instances comprises a series of spots on an array made from deposited sequences.

A molecular array, which array comprises a plurality of:
(i) nucleic acid molecules comprising a nucleotide sequence corresponding to any one or more of the hCG_1815491 markers as hereinbefore defined or a sequence exhibiting at least 80% identity thereto or a functional derivative, fragment, variant or homologue of said nucleic acid molecule; or
(ii) nucleic acid molecules comprising a nucleotide sequence capable of hybridising to any one or more of the sequences of (i) under medium stringency conditions or a functional derivative, fragment, variant or homologue of said nucleic acid molecule; or
(iii) nucleic acid probes or oligonucleotides comprising a nucleotide sequence capable of hybridising to any one or more of the sequences of (i) under medium stringency conditions or a functional derivative, fragment, variant or homologue of said nucleic acid molecule; or
(iv) probes capable of binding to any one or more of the proteins encoded by the nucleic acid molecules of (i) or a derivative, fragment or, homologue thereof
wherein the level of expression of said marker genes of (i) or proteins of (iv) is indicative of the neoplastic state of a cell or cellular subpopulation derived from the large intestine.

A characteristic patient profile is generally prepared by use of an array. An array profile may be compared with one or more other array profiles or other reference profiles. The comparative results can provide rich information pertaining to disease states, developmental state, receptiveness to therapy and other information about the patient.

Another aspect of the present invention provides a diagnostic kit for assaying biological samples comprising an agent for detecting one or more neoplastic marker reagents useful for facilitating the detection by the agent in the first compartment. Further means may also be included, for example, to receive a biological sample. The agent may be any suitable detecting molecule.

The present invention is further described by the following non-limiting examples:

Example 1

Materials and Methods

Extraction of RNA

RNA extractions were performed using Trizol® reagent (Invitrogen, Carlsbad, Calif., USA) as per manufacturer's instructions. Each sample was homogenised in 300 μL of Trizol reagent using a modified dremel drill and sterilised disposable pestles. Additional 200 μL of Trizol reagent was added to the homogenate and samples were incubated at RT for 10 minutes. 100 μL of chloroform was then added, samples were shaken vortexed for 15 seconds, and incubated at RT for 3 further minutes. The aqueous phase containing target RNA was obtained by centrifugation at 12,000 rpm for 15 min, 40° C. RNA was then precipitated by incubating samples at RT for 10 min with 250 µL of isopropanol. Purified RNA precipitate was collected by centrifugation at 12,000 rpm for 10 minutes, 40° C. and supernatants were discarded. Pellets were then washed with 1 mL 75% ethanol, followed by vortexing and centrifugation at 7,500 g for 8 min, 40° C. Finally, pellets were air-dried for 5 min and resuspended in 80 µL of RNase free water. To improve subsequent solubility samples were incubated at 55° C. for 10 min. RNA was quantified by measuring the optical density at A260/280 nm. RNA quality was assessed by electrophoresis on a 1.2% agarose formaldehyde gel.

Gene Chip Processing

Gene Chips were processed using the standard Affymetrix protocol developed for the HU Gene ST 1.0 array described in [Affymetrix, 2007]. Briefly: First cycle dsDNA was synthesized from 100 ng of total RNA extract using random hexamer primers tagged with T7 promoter sequence and SuperScript II (Invitrogen, Carlsbad Calif.) and then DNA Polymerase I. Anti-sense cRNA was then synthesized using T7 polymerase and combined with SuperScript II, dUTP (+dNTP), and random hexamers to synthesize sense strand cDNA incorporating uracil. A combination of uracil DNA glycosylase (UDG) and apurinic/apyrimidinic endonuclease1 (APE 1) were used to fragment the DNA product.

Next, the DNA was biotin labelled by terminal deoxynucleotidyl transferase (TdT) with the Affymetrix proprietary DNA Labeling Reagent covalently linked to biotin. Hybridization to the Custom Chip CG_AGPa520460F was carried out at 45° C. for 16-18 hours. Finally, the chips were washed, stained and scanned as above. All GeneChips analyzed in our lab were stained with streptavidin phycoerytherin and washed with a solution containing biotinylated anti-streptavidin antibodies using the Affymetrix Fluidics Station 450. Finally, the stained and washed microarrays were scanned with the Affymetrix Scanner 3000.

qRT-PCR

Quantitative real time polymerase chain reaction was used to confirm particular gene expression discoveries using Applied Biosystems pre-designed and optimized TaqMan gene expression assays. The resulting expression levels were quantified as a ratio to three genes (HPRT, TBP and GAPDH) with literature reported low variance expression levels. Final results were reported using the A-cycle threshold method. Prior to Real-time PCR analysis 100 ng of total RNA was subject to linear amplification using the QIAGEN QuantiTect Whole Transcriptome amplification kit (QIAGEN, Country) according to the manufacturer's instructions. 2 µl of the amplified, diluted (1:50) cDNA was then analysed in a 25 µl reaction volume by RT-PCR using TaqMan universal master mix (Applied Biosystems, USA) in an ABI prism 7700 sequence detector (Manufacturer. Country) following manufacturer's protocols.

End-Point PCR

Prior to end-point PCR analysis 2 ug of total RNA was subject to linear amplification a high capacity cDNA reverse transcription kit available from Applied Biosystems. 5 µl of the amplified, diluted (1:2) cDNA was then analysied in a 25 µl reaction volume by PCR using a PCR Master Mix (Promega) according to manufacturer's recommendation. 2.5 µl of the amplified products were analysed on 2% agarose E-gel (Invitrogen) along with a 100-base pair DNA Ladder Marker.

Results

We have explored the nucleotide structure and expression levels of transcripts related to hCG_1815491 based on the identification of diagnostic utility of Affymetrix probesets 238021_s_at and 238022_at from our gene chip analysis.

The gene hCG_1815491 is currently represented in NCBI as a single RefSeq sequence, XM_93911. The RefSeq sequence of hCG_1815491 is based on 89 GenBank accessions from 83 cDNA clones. Prior to March 2006, these clones were predicted to represent two overlapping genes, LOC388279 and LOC650242 (the latter also known as hCG_1815491). In March 2006, the human genome database was filtered against clone rearrangements, co-aligned with the genome and clustered in a minimal non-redundant way. As a result, LOC388272 and LOC650242 were merged into one gene named hCG_1815491 (earlier references to hCG_1815491 are: LOC388279, hCG_1815491, LOC650242, XM_944116, AF275804, XM_373688).

We have determined that SEQ ID NO:1, which is defined by the genomic coordinates 8579310 to 8562303 on human chromosome 16 as defined by the NCBI contig reference NT_010498.15|Hs16_10655, NCBI 36 March 2006 genome encompasses hCG_1815491. We have aligned the 10 predicted RNA variants derived from this gene with the genomic nucleotide sequence residing in the map region 8579310 to 8562303. This alignment analysis revealed the existence of at least 6 exons, of which several are alternatively spliced. The identified 6 exons are in contrast to the just 4 exons specified in the NCBI hCG_1815491 RefSeq XM_93911. We have used the identified and expanded exon-intron structure of hCG_1815491 to design specific oligonucleotide primers, which allowed us to measure the expression of RNA variants generated from SEQ ID NO:1 by using PCR-based methodology.

We have conclusively demonstrated the utility of SEQ ID NO:1 to diagnose neoplasia. In particular, we have identified that SEQ ID NO:1 can be used to diagnose adenomas, benign neoplastic lesions that can lead to colorectal adenocarcinoma. We have also demonstrated that SEQ ID NO:1 can be used to diagnose colorectal cancer itself. We hence claim this molecule for broad clinical utility.

In addition, we have conclusively demonstrated neoplastic-specific expression of some of the RNA variants derived from SEQ ID NO:1. Neoplastic-specific splicing of hCG_1815491 has not previously been reported. In particular, RNA variant SEQ ID NO:21 is by far the most pronounced differentially expressed variant of SEQ ID NO:1, and SEQ ID NO:21 appears to be sensitive and specific for colorectal benign pre-cancerous adenomas as well as colorectal carcinoma. Hence we claim diagnostic utility of SEQ ID NO:21 for detection of colorectal neoplasia.

Lastly, we have identified a novel RNA variant, SEQ ID NO:23, derived from alternative splicing of SEQ ID NO:1. This RNA variant is the result of an unprecedented splicing of map regions 8577328-8576605 and 8573324-8573212. We use this example to claim diagnostic utility of any combinations of nucleotide segments derived from SEQ ID NO:1.

Diagnostic Utility of Oligonucleotide Probesets Directed Against hCG_1815491 Using Affymetrix Microarray Genechips The gene expression of human hCG_1815491 was measured by determining the hybridization of RNA extracted from clinical specimens to Affymetrix oligonucleotide probesets, designated 238021_s_at and 238022_at, FIG. 1. The clinical specimens included a total of 454 colorectal tissues derived from 161 adenocarcinoma, 29 adenoma, 42 colitis and 222 non-diseased subjects Conclusion We conclude that transcripts derived from the human gene hCG-1815491 have diagnostic utility for identification of colorectal neoplasia.

Diagnostic Utility of SEQ ID NO:1

Figure 2:
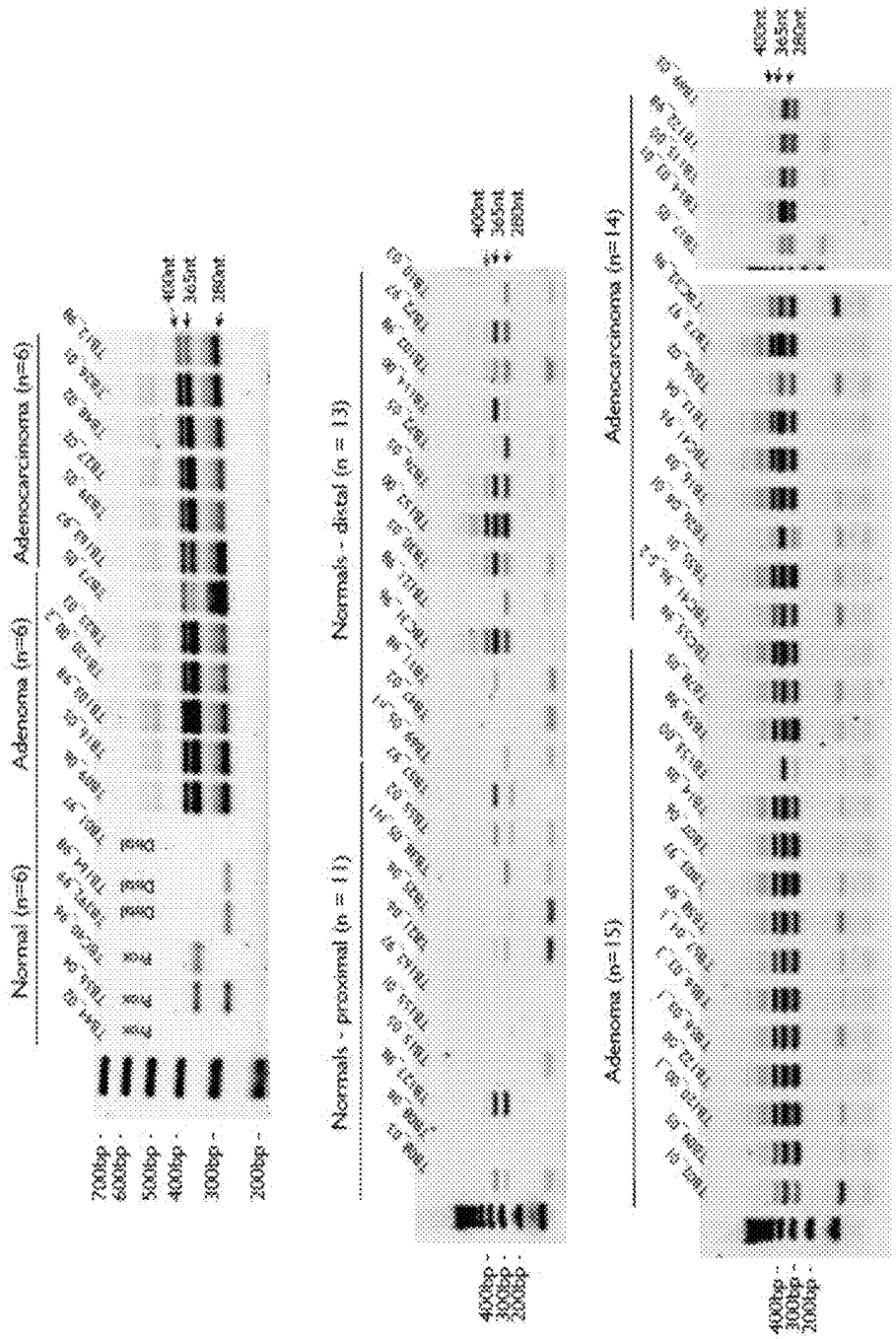
FIG. 2. Detection of SEQ ID NO:1 expression in 71 colorectal tissue specimens. The expression of SEQ ID NO:1 in a total of 71 colorectal specimens from 30 non-diseased controls ("normals"), 21 adenoma and 21 adenocarcinoma subjects was measured by end-point PCR using the forward and reverse oligonucleotide primers 5'-TAACTGGAATTCATGTTGGCTGAAATTCATCCCA (SEQ ID NO:89) and 5'-CACGATAAGCTTTTAT-TATAGTCTATAAACAGGAATACCCAAAACATA TTTAAACC (SEQ ID NO:90). The resulting PCR products were separated by agarose based gel electrophoresis.

End-point PCR, using the oligonucleotide sequence primers, 5'-TAACTGGAATTCATGTTGGCTGAAATTCATCCA (located in SEQ ID NO:6) and 5'-CACGATAAGCTTTTATTATAGTCTATAAACAGGAATACCCAAAACATA TTTAAACC (located in SEQ ID NO:18), was performed to measure the RNA expression level from map region 8573246 to 88567197 within SEQ ID NO:1 in a total of 71 colorectal tissue specimens: 30 non-diseased controls, 21 adenoma tissues and 20 adenocarcinoma tissues, FIG. 2. End-point PCR demonstrated the appearance of four major products that were present in essentially all adenoma and adenocarcinoma colon tissue specimens. Most colon tissue samples from non-disease control specimens produced none or a limited subset of the PCR products. The multiple PCR bands included an approximately 284 base pair product that is the predicted size from the RefSeq NCBI hCG_1815491 entry as well as other bands presumed to arise from alternative splicing.

Conclusion

We conclude that SEQ ID NO:1 that contains map region 8573246 to 88567197 has diagnostic utility as means for detection of colorectal neoplasia.

Diagnostic Utility of SEQ ID NO:1 by Measuring Concentration Levels

Figure 3:
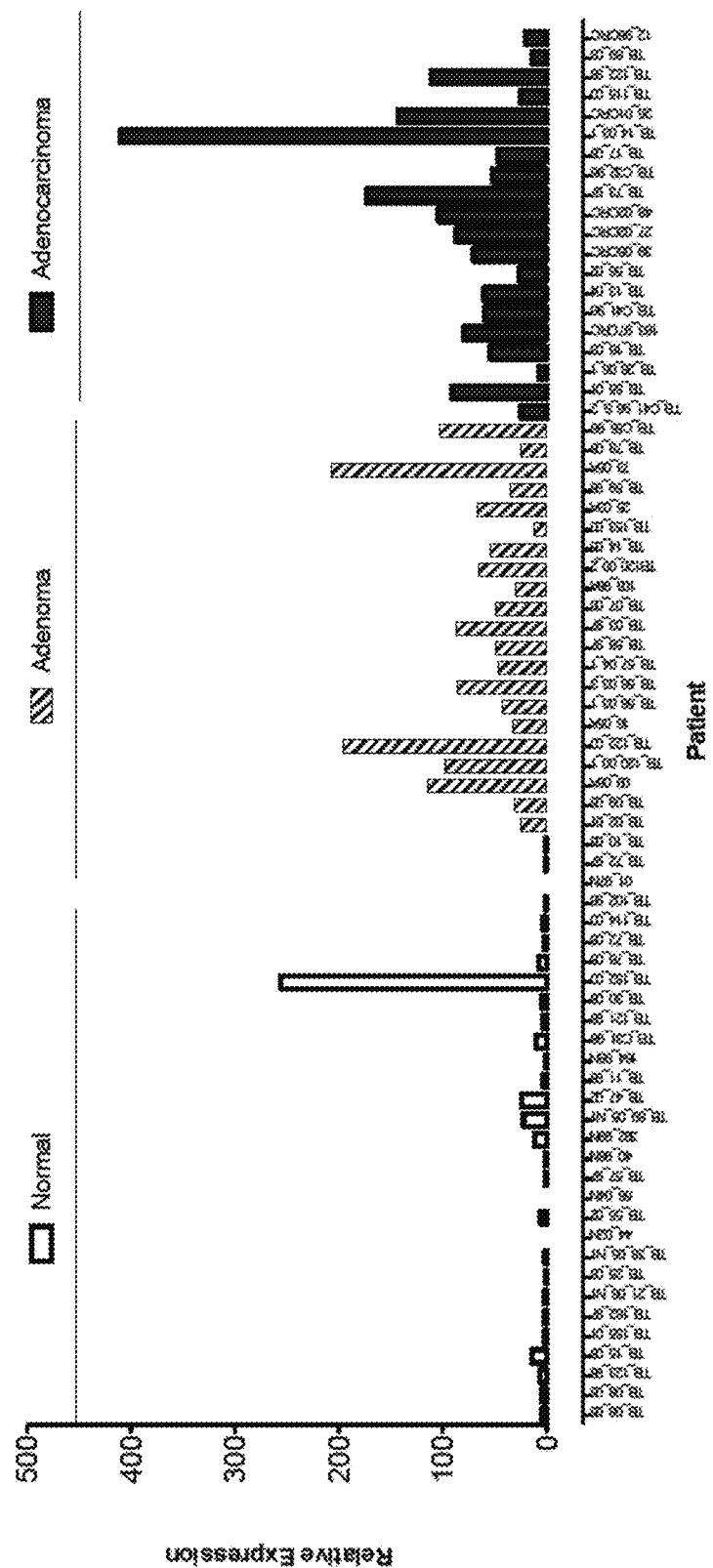
FIG. 3. Measurements of SEQ ID NO:1 RNA concentration levels in colorectal tissue specimens. Quantitative Real-Time PCR, using forward and reverse oligonucleotide primers, 5'-TAACTGGAATTCATGTTGG CTGAAATTCATCCCA (SEQ ID NO:91) and 5'-CACGA-TAAGCTTTTATTATA GTCTATAAACAGGAATAC-CCAAAACATATTT AAACC (SEQ ID NO:92) was performed on RNA extracted from a total of 71 colorectal specimens from 30 non-diseased controls (white), 21 adenoma (striped) and 21 adenocarcinoma (black) subjects. Relative expression levels were calculated as described in Example 1.

Quantitative real-time PCR, using the same oligonucleotide sequence primers as described in Example 2, 5'-TAACTGG AATTCATGTTGGCTGAAATTCATCCCA and 5'-CACGATAAGCTTTTATTATAGTCTATAAACAGGAATACCCAAAACATA TTTAAACC, was performed to measure the RNA concentration level of SEQ ID NO:1 transcripts derived from map region 8573246 to 88567197 in a total of 71 colorectal tissue specimens: 30 non-diseased controls, 21 adenoma tissues and 20 adenocarcinoma tissues, FIG. 3. The figure shows that most normal tissues expressed low or non-detectable levels of transcripts by contrast to adenoma and adenocarcinoma tissues nearly expressed moderate to high levels of transcripts from SEQ ID NO:1.

Conclusion

We conclude that SEQ ID NO:1 that contains map region 8573246 to 88567197 has diagnostic utility as means as detection of colorectal neoplasia.

Diagnostic Utility of RNA Transcript Variants from SEQ ID NO:1 cDNA clones from NCBI/Aceview (Table 4) were used to gather information regarding predicted RNA transcripts derived from hCG_1815491, FIG. 4 & TABLE 1. None of the reported clones were derived from normal or neoplastic colon tissues.

Oligonucleotide sequence primer sets were generated to each of the predicted 10 hCG_1815491 RNA variants (Table 5) and end-point PCR using these primer sets was performed to measure the existence of the ten [10] hCG_1815491 transcript variants in a total of 72 colorectal tissue specimens from 30 non-disease, 21 adenoma and 21 adenocarcinoma subjects.

Figure 5:
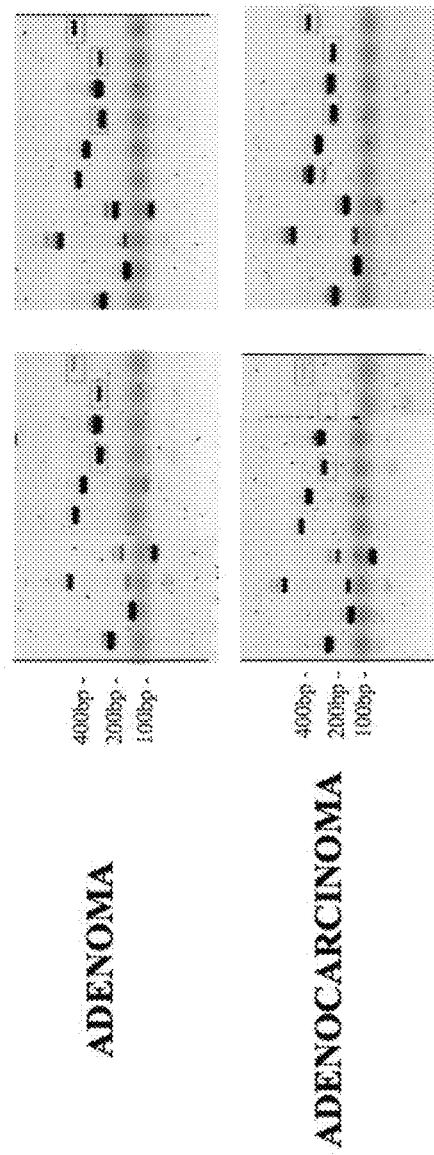
FIG. 5. Example on differential expression of hCG_1815491 RNA variants in colorectal tissue specimens. The expression of the ten predicted RNA transcripts derived from the map region 8579310 to 8562303 on the strand of chromosome 16 was measured by end-point PCR using specific oligonucleotide primer sets (Table 5). DNA sequencing of the resulting PCR amplicons confirmed the products to be derivates of SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:30 and SEQ ID NO:31 (Table 5).

The differential expression of the 10 predicted RNA transcripts, as determined using transcript specific primers, is exemplified in FIG. 5 and Table 2. Differential expression as measured by end-point PCR was observed for several of the 10 RNA variants (TABLE 2) e.g. SEQ ID NO:22, SEQ ID NO:24, SEQ ID NO:27 and in particular SEQ ID NO:21 was the best one.

Conclusion

We conclude that predicted RNA variants derived from SEQ ID NO:1 exist and they are generated through alternative usage of nucleotide segments in SEQ ID NO:1. We conclude that the presence of several of the RNA variants and specific splicing events, such as represented in SEQ ID NO:22, SEQ ID NO:24, SEQ ID NO:27 but in particular SEQ ID NO:21, have diagnostic utility for detection of colorectal neoplasia.

Figure 6:
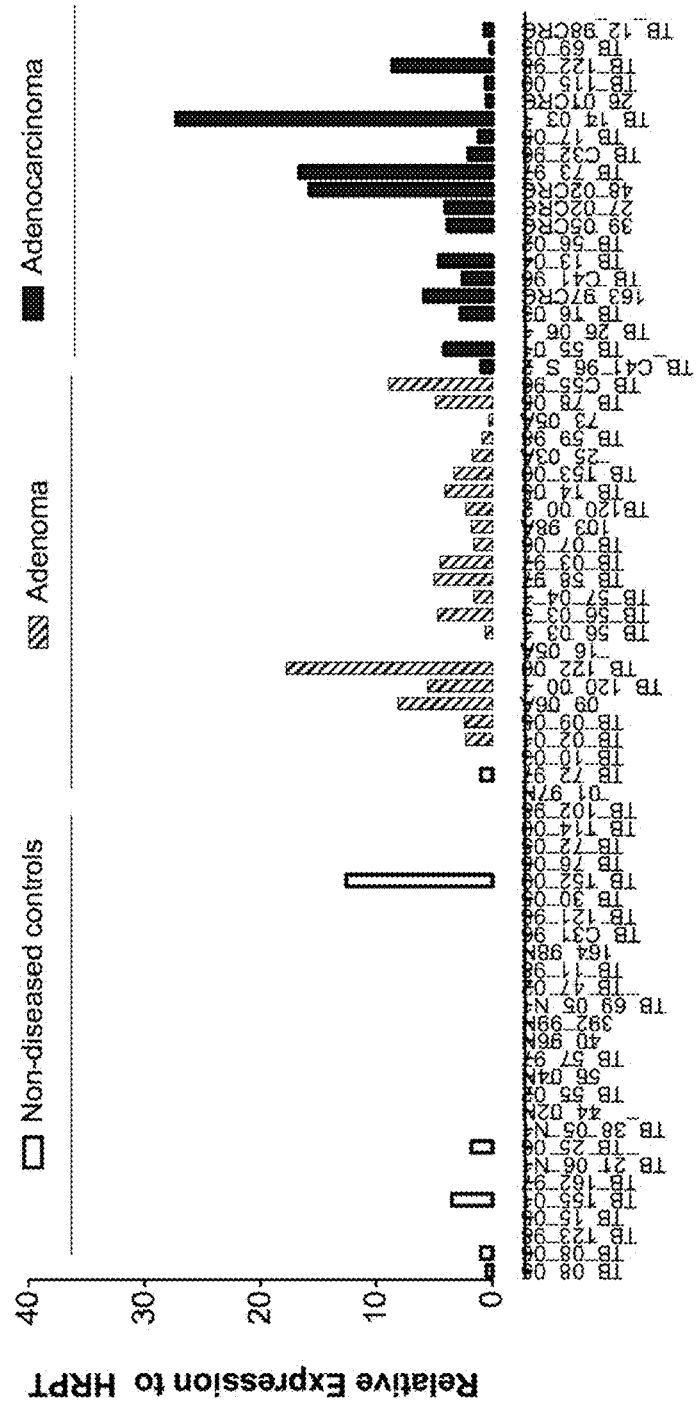
FIG. 6. Measurement of SEQ ID NO:21 RNA concentration levels in colorectal tissue specimens. Quantitative Real-Time PCR, using forward oligonucleotide primer, 5'-ACACGGCTTTCCGGAGTAGA (SEQ ID NO:93), and reverse oligonuclotide primer, 5'-AACAGGTTTTACCTC-CTTATCTTCAGAA (SEQ ID NO:94), was performed on RNA extracted from a total of 71 colorectal tissue specimens from 30 non-diseased controls (white), 21 adenoma (striped) and 20 adenocarcinoma (black) subjects. SEQ ID NO:21 RNA expression levels are depicted relative to HRPT as explained in Example 1.

Diagnostic Utility of RNA Transcript Variants from SEQ ID NO:1, by Measuring Concentration Levels Quantitative Real-Time PCR, was performed to measure the concentration level of RNA variants derived from map region 8579310 to 8562303 on the minus strand of human chromosome 16 in a total of 72 colorectal tissue specimens from 30 non-disease controls, 21 adenoma and 21 adenocarcinoma subjects. Quantitative differences were observed for several of the transcripts, and an example of the quantitative expression profile of SEQ ID NO:21 is given in FIG. 6.

Conclusion

We conclude that measurement of the RNA concentrations of SEQ ID NO:25, SEQ ID NO:30, SEQ ID NO:24 but in particular SEQ ID NO:21 has diagnostic utility for detection of colorectal neoplasia.

Detection of a Novel RNA Variant, SEQ ID NO:23

Figure 7:
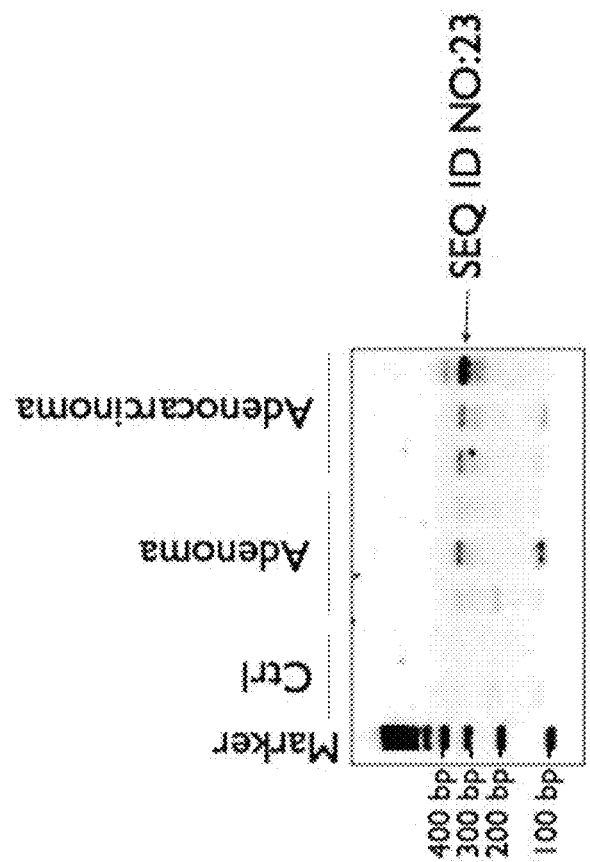
FIG. 7. Identification of a novel RNA variant derived from SEQ ID NO:1. End-point PCR, using a forward oligonucleotide primer, 5'-GGCGGAGGAGAGGTG AGC (SEQ ID NO:95), spanning the junction between SEQ ID NO:4 and SEQ ID NO:5 and a reverse oligonucleotide primer, 5'-GCTGACAGCATCCA AATGTATTATG (SEQ ID NO:96), hybridizing to SEQ ID NO:6, was performed on RNA extracted from colorectal tissue specimens from 2 non-diseased controls (Ctrl), 3 adenoma and 3 adenocarcinoma subjects. The resulting PCR products were separated by agarose-based gel electrophoresis and the products observed in the neoplastic tissue samples were sequenced, which confirmed the novel splicing of SEQ ID NO:4, SEQ ID NO:5 and SEQ ID NO: 6 (Table 5).

We hypothesized that the gene contained within SEQ ID NO:1 contained 6 or more exons that were alternatively spliced in multiple combinations in human colorectal tissue. Alignment of the nucleotide sequences of the predicted mRNA variants derived from hCG_1815491 illustrated that the first 184 nucleotides of RNA SEQ ID NO:25, map region 8577328-8576881 in SEQ ID NO:1, and the first 274 nucleotides of RNA SEQ ID NO:21, map region 8576878-8576605 in SEQ ID NO:1, were in fact flanking each other. End-point PCR, using a forward primer spanning the splice junction of SEQ ID NO:4 and SEQ ID NO:5, 5'-GGCGGAGGAGAGGTGAGC, with a reverse primer 5'-GCTGACAGCATCCA AATGTATTATG hybridizing to SEQ ID NO:6 was performed to demonstrate a novel RNA variant derived from alternative splicing of map region 8576892-8576605 with 8573324-8573280, FIG. 7. The novel RNA variant, named SEQ ID NO:23, appeared up-regulated in colorectal tissue specimens from 3 adenoma and 3 adenocarcinoma subjects but not in 2 non-disease controls, FIG. 7.

Conclusion

Review of all publicly available data indicates that a nucleotide sequence corresponding the SEQ ID NO:23 has never before been identified. We conclude that SEQ ID NO:23 represents a novel RNA variant derived from SEQ ID NO:1. While new sequence data is common with respect to the human genome project, we have identified that this transcript designated SEQ ID NO:23 is a splice variant diagnostic of colorectal neoplasia.

Diagnostic Utility of Individual Exons of hCG_1815491

Figure 8:
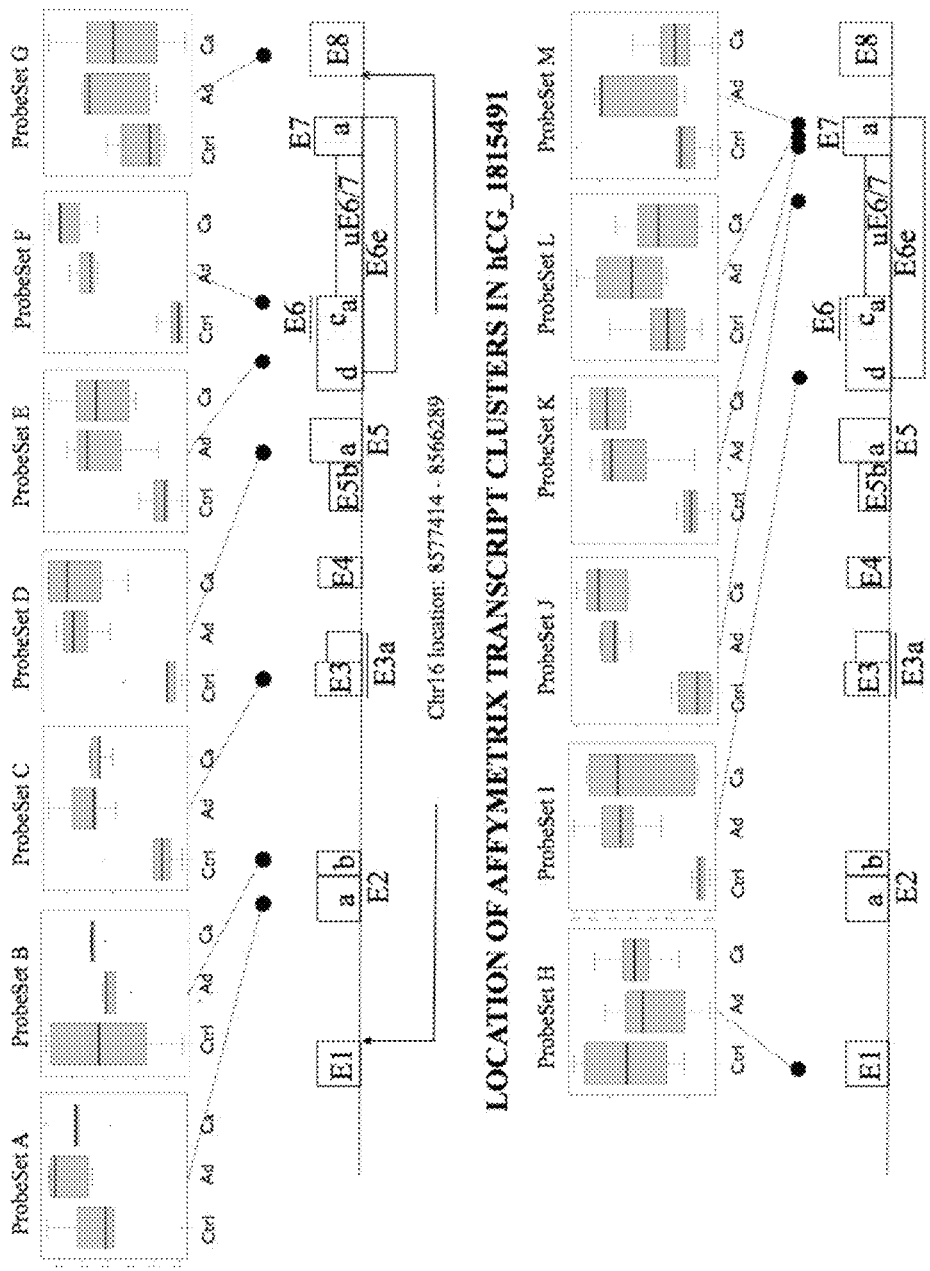
FIG. 8. Measurement of expression of individual target regions in SEQ ID NO:1. The level of RNA hybridization to 13 Affymetrix probesets, Table 3, residing in the map region 8579310 to 8562303 was measured using the Affymetrix GeneChip HuGene Exon 1.0 as recommended by manufacturer. RNA was extracted from colon tissue specimens from 5 non-diseased controls (left bar in boxplots), 5 adenoma (middle bar in boxplots) and 5 adenocarcinoma subjects (right bar in boxplots). The individual boxplots are also given in FIGS. 9-21. The relationship of exon "E" numbering and SEQ ID NO. numbering is further defined in Table 1.
Figure 9:
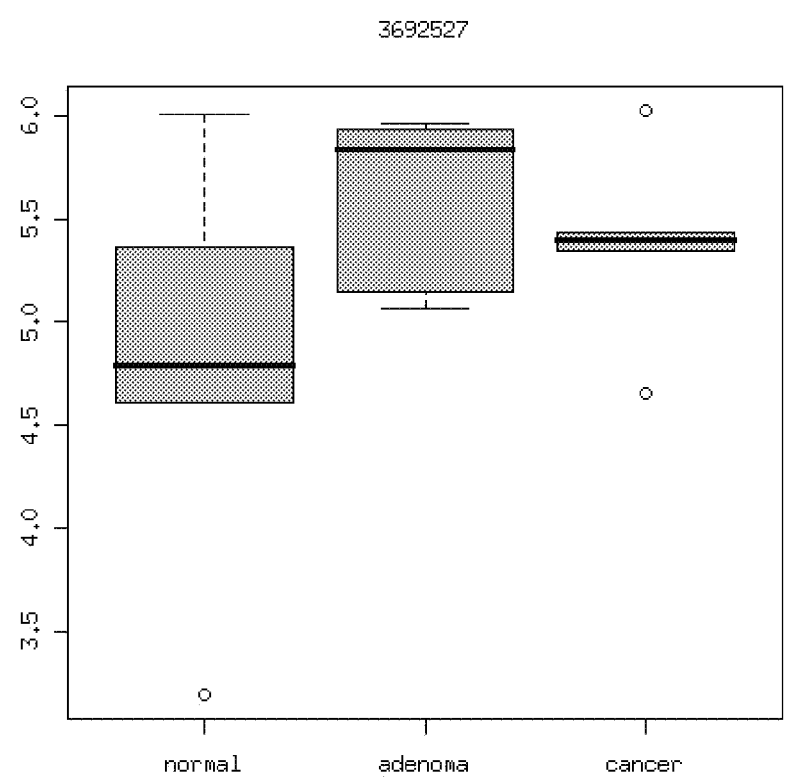
FIG. 9. Measurement of RNA expression on Affymetrix GeneChip HuGene Exon 1.0 probeset ID 3692527 (referred to as Probeset A in FIG. 8) targeting map region 8577230 to 8576913 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1
Figure 10:
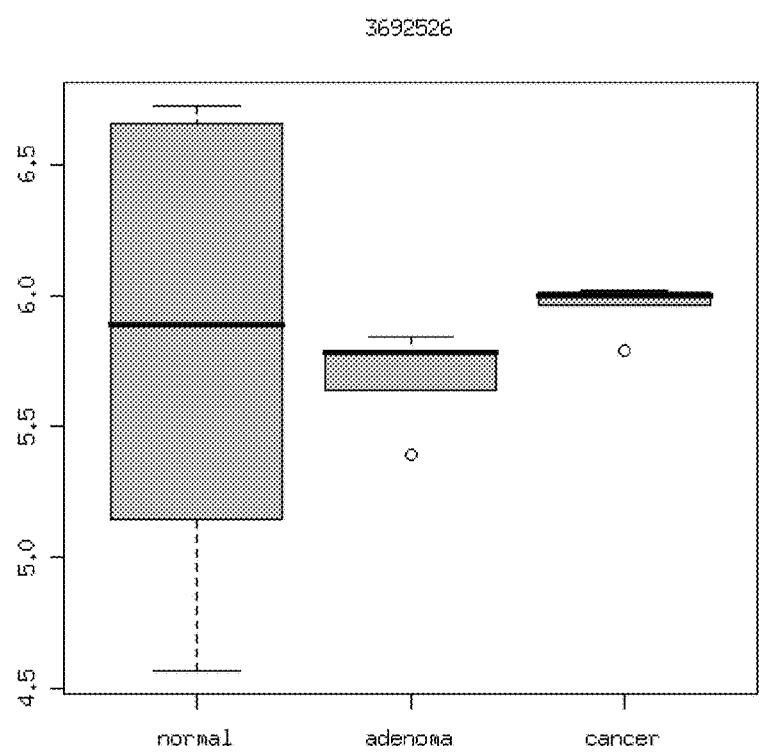
FIG. 10. Measurement of RNA expression on Affymetrix GeneChip HuGene Exon 1.0 probeset ID 3692526 (referred to as Probeset B in FIG. 8) targeting map region 8576785 to 8576609 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1
Figure 11:
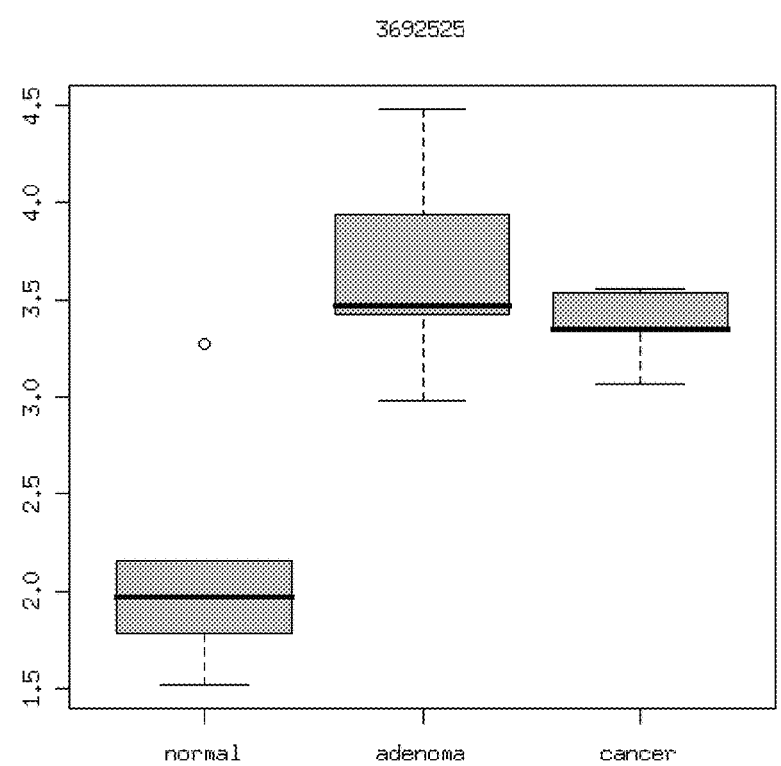
FIG. 11. Measurement of RNA expression on Affymetrix GeneChip HuGene Exon 1.0 probeset ID 3692525 (referred to as Probeset C in FIG. 8) targeting map region 8573317 to 8573214 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 12:
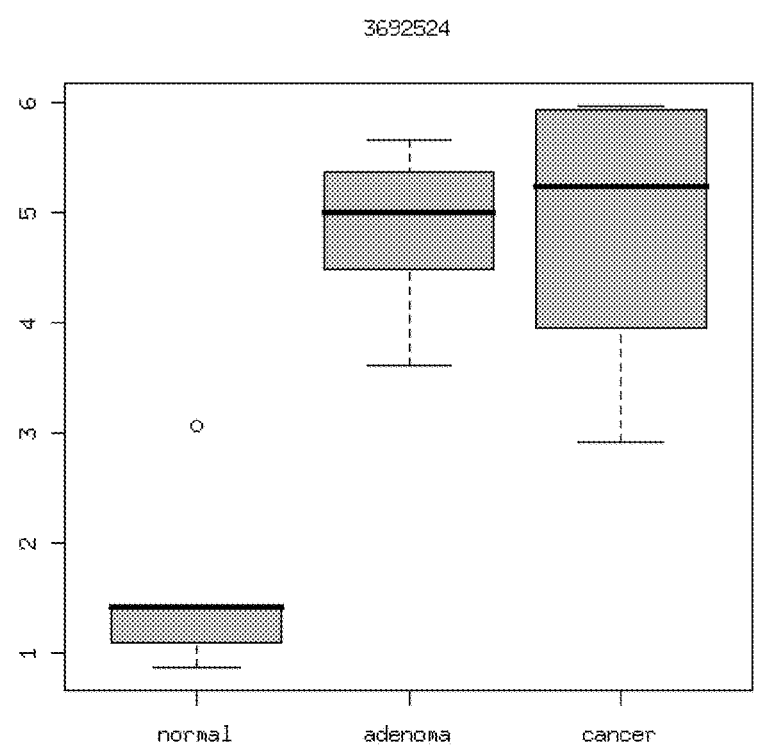
FIG. 12. Measurement of RNA expression on Affymetrix GeneChip HuGene Exon 1.0 probeset ID 3692524 (referred to as Probeset D in FIG. 8) targeting map region 8571756 to 8571721 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 13:
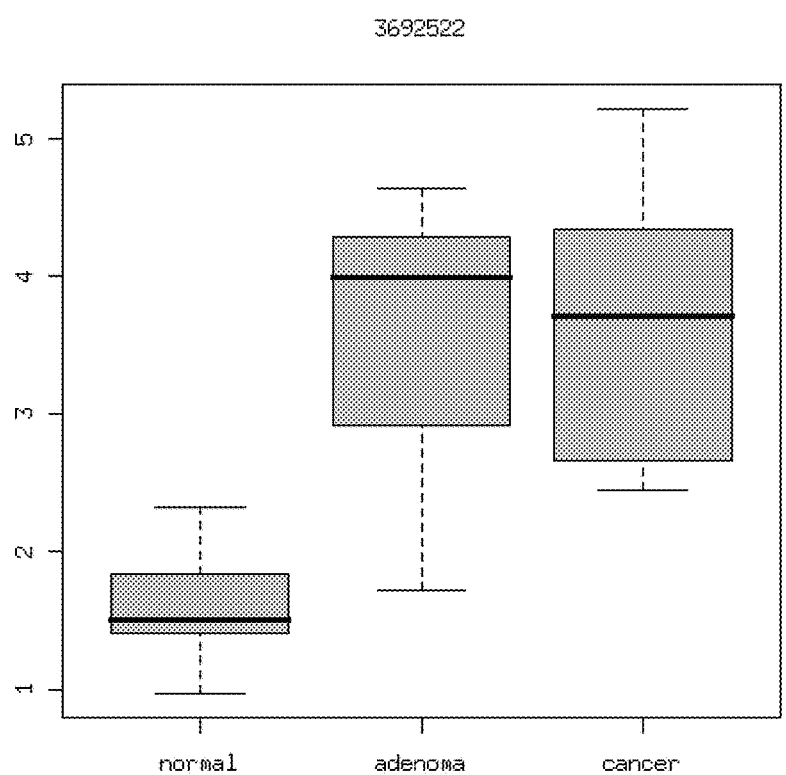
FIG. 13. Measurement of RNA expression on Affymetrix GeneChip HuGene Exon 1.0 probeset ID 3692522 (referred to as Probeset E in FIG. 8) targeting map region 8568480 to 8568447 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 14:
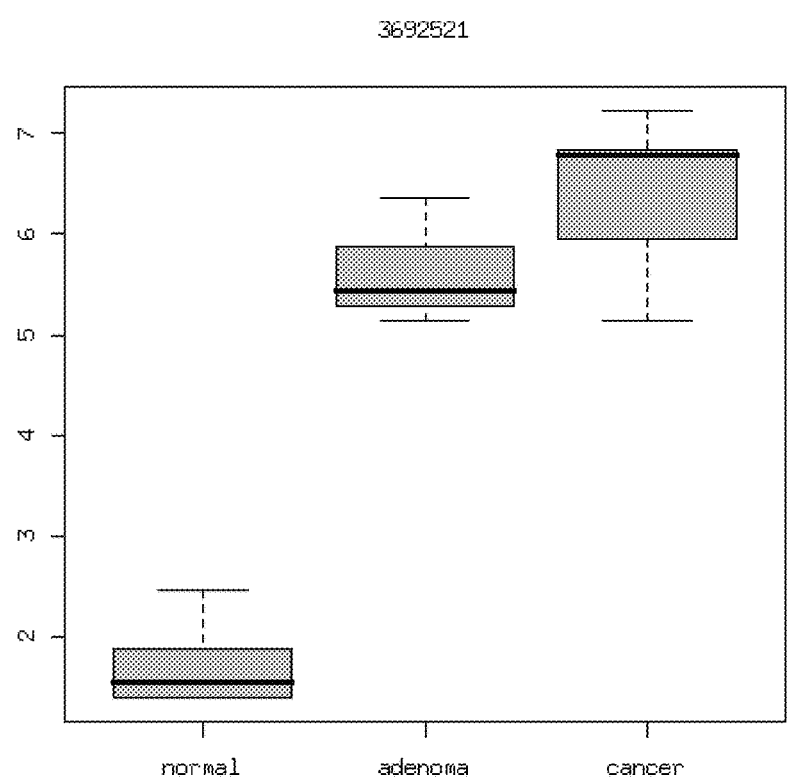
FIG. 14. Measurement of RNA expression on Affymetrix GeneChip HuGene Exon 1.0 probeset ID 3692521 (referred to as Probeset F in FIG. 8) targeting map region 8568438 to 8568409 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 15:
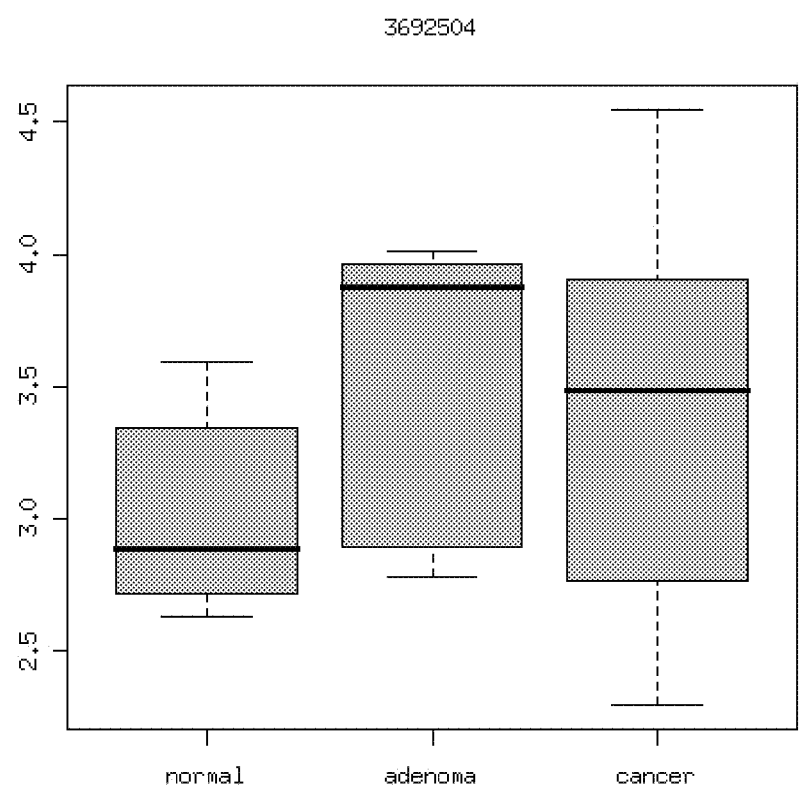
FIG. 15. Measurement of RNA expression on Affymetrix GeneChip HuGene Exon 1.0 probeset ID 3692504 (referred to as Probeset G in FIG. 8) targeting map region 8566289 to 8566014 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 16:
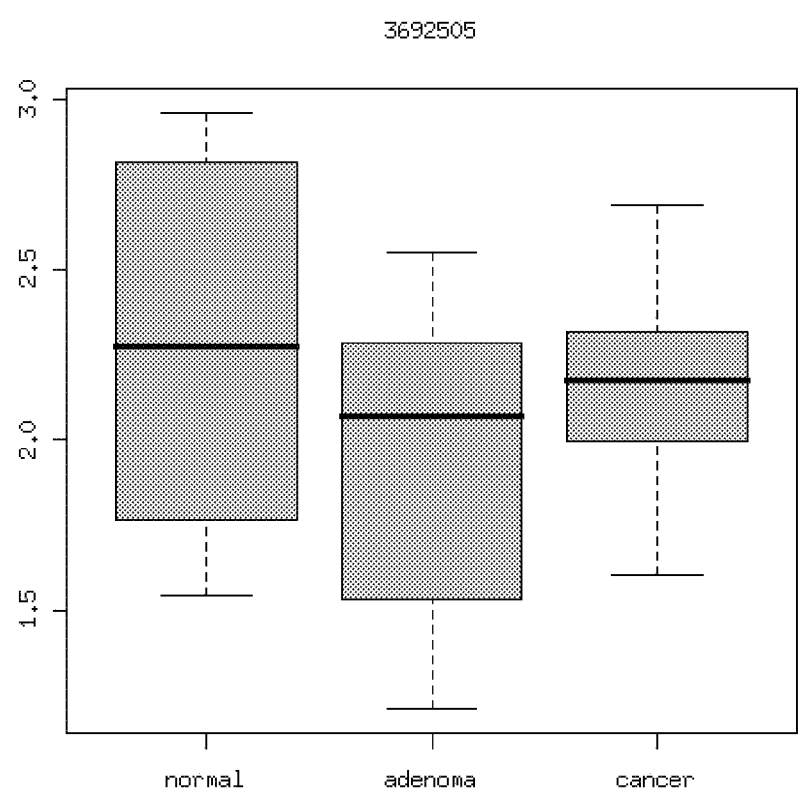
FIG. 16. Measurement of RNA expression on Affymetrix GeneChip HuGene Exon 1.0 probeset ID 3692505 (referred to as Probeset H in FIG. 8) targeting map region 8577467 to 8577374 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 17:
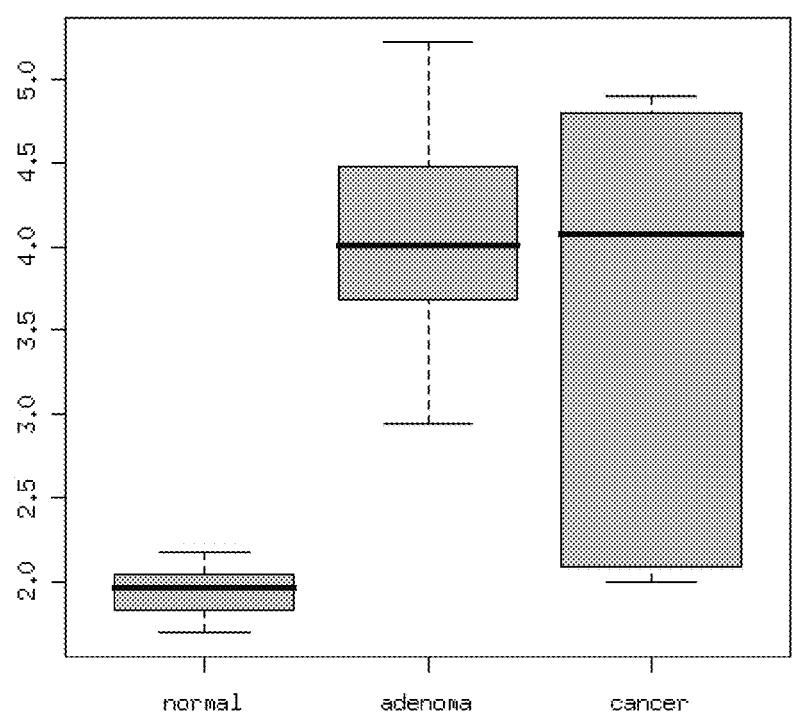
FIG. 17. Measurement of RNA expression on Affymetrix GeneChip HuGene Exon 1.0 probeset ID 3692523 (referred to as Probeset I in FIG. 8) targeting map region 8569323 to 8568689 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 18:
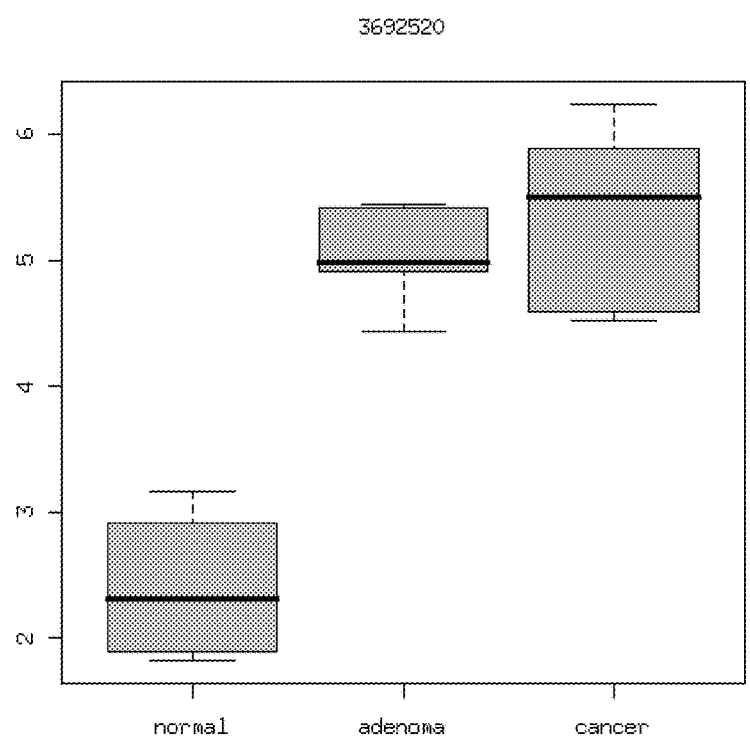
FIG. 18. Measurement of RNA expression on Affymetrix GeneChip HuGene Exon 1.0 probeset ID 3692520 (referred to as Probeset J in FIG. 8) targeting map region 8568331 to 8567516 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 19:
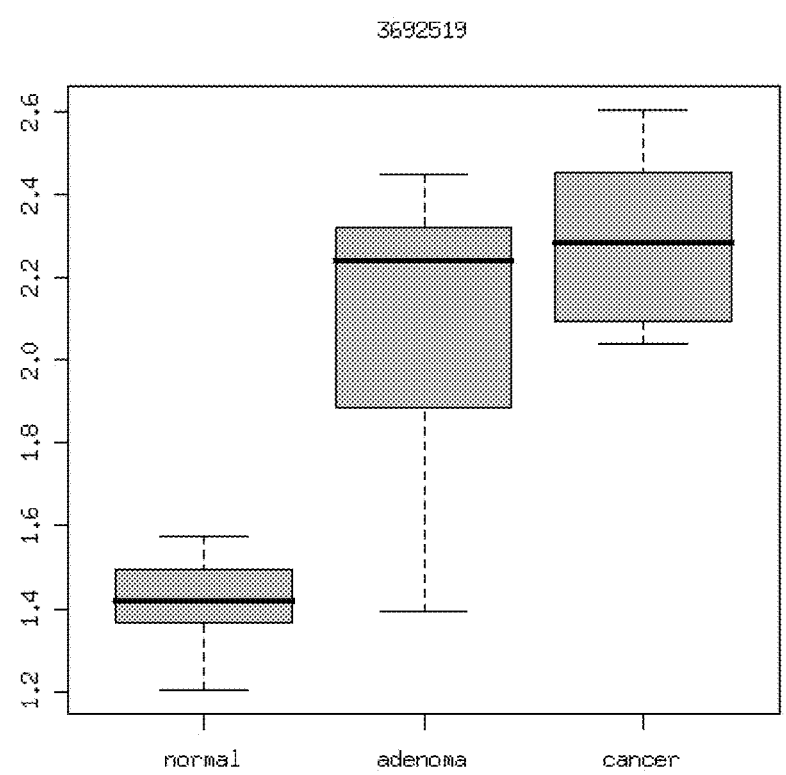
FIG. 19. Measurement of RNA expression on Affymetrix GeneChip HuGene Exon 1.0 probeset ID 3692519 (referred to as Probeset K in FIG. 8) targeting map region 8567301 to 8567162 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 20:
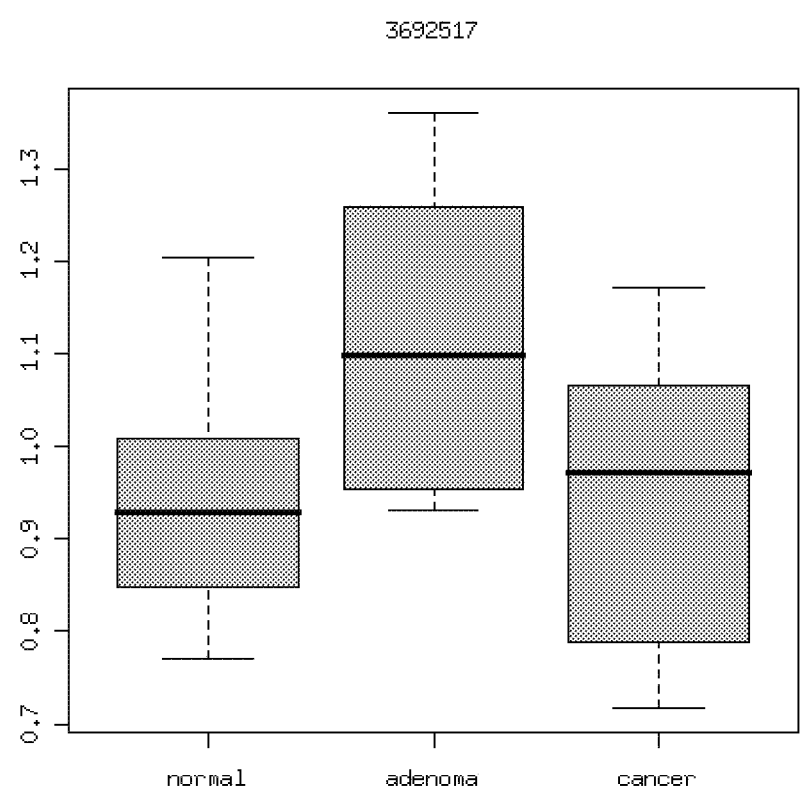
FIG. 20. Measurement of RNA expression on Affymetrix GeneChip HuGene Exon 1.0 probeset ID 3692517 (referred to as Probeset L in FIG. 8) targeting map region 8567033 to 8566994 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.
Figure 21:
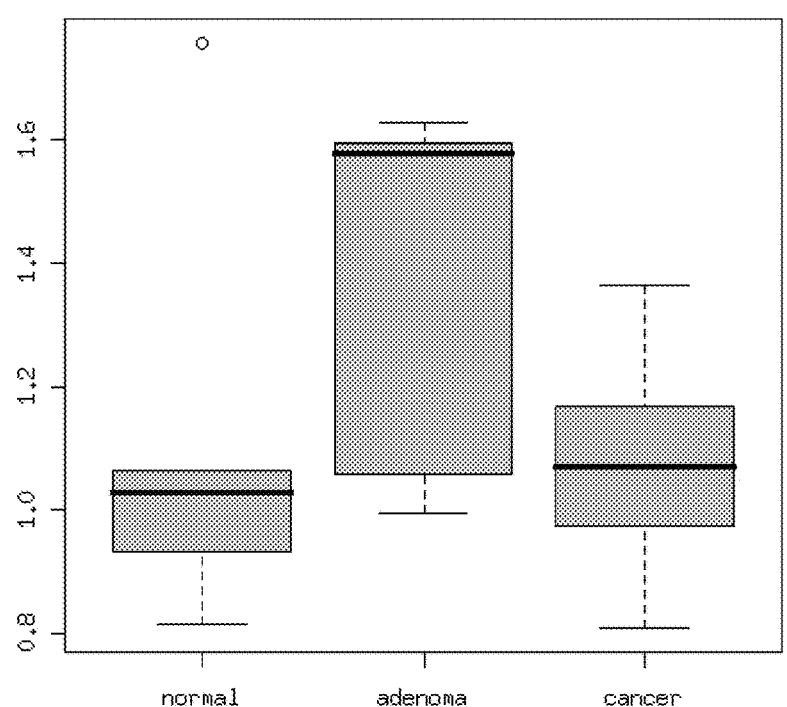
FIG. 21. Measurement of RNA expression on Affymetrix GeneChip HuGene Exon 1.0 probeset ID 3692518 (referred to as Probeset M in FIG. 8) targeting map region 8567158 to 8567091 of SEQ ID NO:1. Expression profiles were obtained from hybridisation analysis of RNA extracted from colon tissue specimens from 5 non-diseased controls, 5 adenoma and 5 adenocarcinoma subjects as further described in Example 1.

Gene expression across the chromosomal map region 8579310 to 8562303 on chromosome 16 was measured by determining the hybridization of RNA extracted from clinical specimens to the Affymetrix oligonucleotide probesets specified in TABLE 3. The observed differential expression of the probesets specified in Table 3 from 5 non-disease subjects, 5 adenoma and 5 adenocarcinoma subjects are summarized in FIG. 8. Details of the differential expression across the 13 probesets are provided in FIG. 9-21. We note that expression was not measured across all predicted exons from SEQ ID NO:1, as the available probesets on the Affymetrix GeneChip HuGene Exon 1.0 only targeted a subset of the predicted exons in SEQ ID NO:1.

Conclusion

We conclude that the map region 8577414 to 8566289 has diagnostic utility for identification of colorectal neoplasia. In particular, Affymetrix probesets 3692525 (SEQ ID NO:6), 3692524 (SEQ ID NO:9), 3692519 (SEQ ID NO:18), 3692520 (SEQ ID NO:17), 3692523 and 3692522 (SEQ ID NO:15), and 3692521 (SEQ ID NO:13) can be used to diagnose adenomas, benign neoplastic lesions that can lead to colorectal adenocarcinoma. We also conclude that these probesets can be used to diagnose colorectal cancer itself.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

LIST OF MOLECULE SEQUENCES

| SEQUENCE ID | FIG. 23 | Nucleotide sequence | Genomic Map Region - Human Chromosome 16 |
|---|---|---|---|
| SEQ ID NO: 1 | | SEE FIG. 2 | 8579310-8562303 |
| SEQ ID NO: 21 | E2b-E3-E5a-E6-E7a | gagccccgcccgggccaggccctctggccgcgccgtccgcccctctagt cgtgtcccctcgtgggccgaacggacgcggcggtgcccgcgcccgacca gacgtcccgtgggctagggcctgggcctcgggccgcgtcggcgccggtcg agcctctccgggtgtcggggttcggggcgggcgcgcgtgggcgtggctcc tctgtccacgcctgttcccttcgtcgccgcggctctcgtccgggacacgg ctttccggagtagagcccttggaggtgttaagtgtgatgcttccataata catttggatgctgtcagctaagttcacttctgaactaaggggttcctcca aatgttggctgaaattcatcccaaggctggtctgcaaagtctgcaattca taatggagctactgtactggctattggaaggaggagattctgaagataag gaggtaaaacctgtttagaaattaaaaatgagttacgatttaaagaaaat tcagatgactcattgtgagtgctagttctcttgtaggatgccactggaaa tgttgaaatgaaaaatattcagccgttggtctttgaaaattcctgtgatg tgtttcaatctagatgcaaagaacatggaaaaatcaaagtgctcgagtgg tttaaatatgttttgggtattcctgtttatagactataatacttttccaa ttaaaatcctcagttgtcacgcagaagaaggttaagctgtatttgattgc cagttttactgaaaatgcttagtattttacagtatcaccaaatatatttt gtttagccaaggtataggaaaaataaaattgtataggttgacttttct caaaatgtctttattggattgaatgaatgtttatacctgaaaaaaaaaggttcaaaaaaa | 8576878-8576605 8573324-8573212 8571761-8571696 8568521-8568409 8567320-8566974 |
| SEQ ID NO: 22 | E2b-E3-E5a-E6c-E7a | Gagccccgcccgggccaggccctctggccgcgccgtccgcccctctagt cgtgtcccctcgtgggccgaacggacgcggcggtgcccgcgcccgacca gacgtcccgtgggctagggcctgggcctcgggccgcgtcggcgccggtcg agcctctccgggtgtcggggttcggggcgggcgcgcgtgggcgtggctcc tctgtccacgcctgttcccttcgtcgccgcggctctcgtccgggacacgg ctttccggagtagagcccttggaggtgttaagtgtgatgcttccataata catttggatgctgtcagctaagttcacttctgaactaaggggttcctcca aatgttggctgaaattcatcccaaggctggtctgcaaagtctgcaattca taatggagctactgtactggctattggaaggaggagattctgaagataag gagttctcttgtaggatgccactggaaatgttgaaatgaaaaatattcag ccgttggtctttgaaattcctgtgatgtgtttcaatctagatgcaaaga acatggaaaaatcaaagtgctcgagtggtttaaatatgttttgggtattc ctgtttatagactataatacttttccaattaaaatcctcagttgtcacgc agaagaaggttaagctgtatttgattgccagttttactgaaaatgcttag tattttacagtatcaccaaatatatttgtttagccaaggtataggaaaa ataaaataaattgtataggttgacttttttctaaaatgtctttattggat tgaatgaatgtttatacctgaaaaaaaaaggttcaaaaaaa | 8576878-8576605 8573324-8573212 8571761-8571696 8568449-8568409 8567320-8566974 |
| SEQ ID NO: 23 | E2a-E2b-E3 | tctcggcgccagaggggcgggaggggcgggtctcgatcgcgctattgt catggagacgggaagctggctgcagcggcggcgggaccgtggggccgag gtggctgccagccggccaatgtctaagcgaggcggagcggcccaggcggc ccgagcctgggggagcgcgcagccggccagtggcggcctcgccggcggcc tcttcccgggctcgcagtaggcccgagtcgtcgccgggagctcctgggag cagcgtccccgccctgctccctcgctcccgcctcttgcggccccacggc ccctcagcgcccgcccccggctccgcccgccgcagccgcagcccctggcg ctaacggtcggtaacggcccgcgcgcgccgcccgccggggggctcgcgcca gccacgagggagcgtccgcgggcccgcgcgcccgcgcggcggaggagaggt gagccccgcccgggccaggccctctggccgcgccgtccgcccctctagt cgtgtcccctcgtgggccgaacggacgcggcggtgcccgcgcccgacca gacgtcccgtgggctagggcctgggcctcgggccgcgtcggcgccggtcg agcctctccgggtgtcggggttcggggcgggcgcgcgtgggcgtggctcc tctgtccacgcctgttcccttcgtcgccgcggctctcgtccgggacacgg ctttccggagtagagcccttggaggtgttaagtgtgatgcttccataata | 8577328-8576605 8573324-8573212 |

TABLE 1-continued

LIST OF MOLECULE SEQUENCES

| SEQUENCE ID | FIG. 23 | Nucleotide sequence | Genomic Map Region - Human Chromosome 16 |
|---|---|---|---|
| | | catttggatgctgtcagctaagttcacttctgaactaaggggttcctcca aatgttggctgaaattcatcccaaggctggtctgcaa | |
| SEQ ID NO: 24 | E5b - E6-E7a | catgcttttttgagaagtgtatcatctaggaagaaaatcaaatggagtatt ggtaattaaattgtaattccatgaaggaaggaagtggtgcaaaagatgaa gctaactattcctgttttttcttttta<u>ag</u>agtctgcaattcataatggagc tactgtactggctattggaaggaggagattctgaagataaggaggtaaaa cctgtttagaaattaaaaatgagttacgatttaaagaaaattcagatgac tcattgtgagtgct<u>ag</u>ttctcttgt<u>ag</u>gatgccactggaaatgttgaaat gaaaaatattcagccgttggtctttgaaatttcctgtgatgtgtttcaat ctagatgcaaagaacatggaaaaatcaaagtgctcgagtggtttaaatat gttttgggtattcctgtttatagactataatacttttccaattaaaatcc tcagttgtcacgcagaagaaggttaagctgtatttgattgccagttttac tgaaaatgcttagtattttacagtatcaccaaatatattttgtttagcca aggtataggaaaaataaaataaattgtataggttgactttttctaaaat gtctttattggattgaatgaatgtttatacctgaaaaaaaaggttcaaa aaaa | 8571889-8571696 8568521-8568409 8567320-8566974 |
| SEQ ID NO: 25 | E2a-E3a | tctcggcgccagaggggcggggaggggcgggtctcgatcgcgctattgt catggagacgggaagctggctgcagcggcggcggggaccgtggggccgag gtggctgccagccggccaatgtctaagcgaggcggagcggcccaggcggc ccgagcctgggggagcgcgcagccggccagtggcggcctcgccggcggcc tcttcccgggctcgcagtaggcccgagtcgtcgccgggagctcctgggag cagcgtcccgccctgctccctcgctcccgcctcttgcgggccccacggc ccctcagcgcccgccccggctccgcccgccgcagccgcagccctggcg ctaacggtcggtaacggcccgcgcgcgccgcccgccggggcctcgcgcca gccacgagggagcgtccgcggcccgcgcgcccgcgcggcggaggagaggt gttaagtgtgatgcttccataatacatttggatgctgtcagctaagttca cttctgaactaaggggttcctccaaatgttggctgaaattcatcccaagg ctggtctgcaa<u>gt</u>gagtgtctgcacacagtttgcttgtatgtggagtcga tccaaaatagcatcaatgttggttttaccaaagtatttattattgataat agaggctaagtacaaaatgtagagaatgtcagctacttgaggcctttgat tattaaaattttattaatgcattaaacaaga | 8577328-8576881 8573324-8573041 |
| SEQ ID NO: 26 | E3-E5a-E6a-E7a | gtgttaagtgtgatgcttccataatacatttggatgctgtcagctaagtt cacttctgaactaaggggttcctccaaatgttggctgaaattcatccca ggctggtctgcaaagtctgcaattcataatggagctactgtactggctat tggaaggaggagattctgaagataaggaggatgccactggaaatgttgaa atgaaaaatattcagccgttggtctttgaaatttcctgtgatgtgtttca atctagatgcaaagaacatggaaaaatcaaagtgctcgagtggtttaaat atgttttgggtattcctgtttatagactataatacttttccaattaaaat cctcagttgtcacgcagaagaaggttaagctgtatttgattgccagtttt actgaaaatgcttagtattttacagtatcaccaaatatattttgtttagc caaggtataggaaaaataaaataaattgtataggttgacttttttctaaa atgtctttattggattgaatgaatgtttatacctgaaaaaaaaaggttca aaaaaa | 8573324-8573212 8571761-8571696 8568438-8568409 8567320-8566974 |
| SEQ ID NO: 27 | E2a-E3-E4-E5a-E6-E7a | tctcggcgccagaggggcggggaggggcgggtctcgatcgcgctattgt catggagacgggaagctggctgcagcggcggcggggaccgtggggccgag gtggctgccagccggccaatgtctaagcgaggcggagcggcccaggcggc ccgagcctgggggagcgcgcagccggccagtggcggcctcgccggcggcc tcttcccgggctcgcagtaggcccgagtcgtcgccgggagctcctgggag cagcgtcccgccctgctccctcgctcccgcctcttgcgggccccacggc ccctcagcgcccgccccggctccgcccgccgcagccgcagccctggcg ctaacggtcggtaacggcccgcgcgcgccgcccgccggggcctcgcgcca gccacgagggagcgtccgcggcccgcgcgcccgcgcggcggaggagaggt gttaagtgtgatgcttccataatacatttggatgctgtcagctaagttca cttctgaactaaggggttcctccaaatgttggctgaaattcatcccaagg ctggtctgcattacctatttctttttaagaataaatttagtgggaatatca gttccagtcatgggtaccaaactttttagtgacagagtacacacagagt ctgcaattcataatggagctactgtactggctattggaaggaggagattc tgaagataaggaggtaaaacctgtttagaaattaaaaatgagttacgatt taaagaaaattcagatgactcattgtgagtgct<u>ag</u>ttctcttgt<u>ag</u>gatg ccactggaaatgttgaaatgaaaaatattcagccgttggtctttgaaatt tcctgtgatgtgtttcaatctagatgcaaagaacatggaaaaatcaaagt gctcgagtggtttaaatatgttttgggtattcctgtttatagactataat acttttccaattaaaatcctcagttgtcacgcagaagaaggttaagctgt atttgattgccagttttactgaaaatgcttagtattttacagtatcacca aatatattttgtttagccaaggtataggaaaaataaaataaattgtatag gttgacttttttctaaaatgtctttattggattgaatgaatgtttatacc tgaaaaaaaaggttcaaaaaaa | 8577328-8576881 8573324-8573212 8572798-8572712 8571761-8571696 8568521-8568409 8567320-8566974 |

TABLE 1-continued

LIST OF MOLECULE SEQUENCES

| SEQUENCE ID | FIG. 23 | Nucleotide sequence | Genomic Map Region - Human Chromosome 16 |
|---|---|---|---|
| SEQ ID NO: 28 unspliced | E6e | tgataagcaacatccaaatattttgaccctgcttttagtggttttttca aatcttattttgagtcttacttttagtcatagaatagctactgatttgat gcggtctttaactgacttaatattttacaatttcaatatattttgcatt ggaatctccagtaatgaatattaaaatatatgtacaatcatttgtagatg atatcaattatattaagacatttcagatgggctattgtagtatttaatgt gccgtattttatggtagaataattctcagtctctggacatcaagattgct ttcagtgggaatgaagattaatttacttcagtcctgattttttaggcatc aatgcatgttttcatttttgtcagacttttacccctcttttaatgtaattc tcaacttcttatggatttacttcccaatacataaaatccttcaaaacaag aatgataataattttatacttttttataaaaataaattattttttagtcc atcaaggtgtctgaagatttatgcctaggtatctccatatctaacttga taaggaaaataggataaacaatgctggtaatagcaggaaagtaagtattt gaataagatgtcaaactgatatttcatgtgaacctaacttaatggt aactaataattatcttatttaaatcaataggtaaaacctgtttagaaatt aaaaatgagttacgatttaaagaaaattcagatgactcattgtgagtgct agttctcttgtaggatgccactggaaatgttgaaatgaaaaatgtaagta tatcttttggtggaaaaaaggatagtctctaggacacaaaattactgttt tatttttttctcaggagtttgcctaagggtgtgacagatgatctctgtca cttgtcttagttgtgtcctgcaataaaactggatgctttataaaatactag acctgtgatttcgtatgctgtaatatttcatttctccatcaccccctccaa attatttcttagtttggagtaaaataataaatgtattatagtcaacatct cttgaccccctcttttagtttcagctaaactaagcatgtgtgtttgtgtgtt cattttatagttcatgtgtagaactatgtgaattaaatttaagaaacatg taaagtagaggaaatagttttctggagaaattttttccttttggatatta tgcccttttccattgcttttctctgcttgaaagcaaaaaaaagtacccta cccctgttctccttagggaaaaactattcctataaagtattttttaaatc gtgcaagtcattgcctagggttagctaaaacatttcttttttaaaaaggag aaaatgcccggctttaacattttcttgtatttgtatctattaagataaa cagttacttttgatacagtacataccaatctacttaatttttttttccagg attccttttactatgtttggtctgaccttttatgataacttaatatggga acaaattagcatataattctattttccatgtgacctcaaccagttgcaga attgtaccactactttagggggggcaatttgacagtttatgtagactata gcattaattgttcccaaatgttcagtgcatcctggctaatgtgttattga aggtgttttcacgtaagcagttagaggaagcacttcaccccctattactaa gttattaaaatgcctcctaaaggtagcatttaaattagtatacataatt gattagtaatttgtcttctcccaagcataaaacagcatagcagagtaag tgtgaccagtgaagtataagatattagggattgatggtgacaatgatcat agcaactaaatggatttttttttttcttttagattcagccgttggtctttg aaatttcctgtgatgtgtttcaatctagatgcaaagaacatggaaaaatc aaagtgctcgagtggtttaaatatgtttgggtattcctgtttatagact ataatacttttccaattaaaatcctcagttgtcacgcagaagaaggttaa gctgtatttgattgccagttttactgaaaatgcttagtatttttacagtat caccaaatatattttgtttagccaaggtataggaaaaataaaataaattg tataggttgacttttttctaaaatgtctttattggattgaatgaatgttt atacctgaaaaaaaaggttcaaaaaaat | 8599201- 8566974 |
| SEQ ID NO: 29 | E6d - E7a | tttaatagaaggaaaatataaatttaatatctgggcaattgagacctttca aacttactttaaaagtatgatcttgatgtatatgatactgttttgtcttt gctatattaacagaattagaggggtgttctgcaattcaaatacctttat attccaaatttttattctctataatggacttttaaaataaaagtatatgt gcttcaagagggcaaaatttgaatcatgagctaatttgctaagcatcaga ttatagaaaagcatccttgattaatttggaactgtgaagggggcgggta aaactgttttctgcagaaatttactagtgcagcaaccattttaaattaaat gtttgttaacataatagtgatggcattttctcctcccccctccttgtggtt ttgtccaactagatgttacagtggcagttgcactgactgttaagtgttta aatgatgacaccattatgtgaagtgattttgaaatgagagattccagcca agaattacatctgctcccatctccttcaaatcatactctctggcagtaca gattatgattgatttgtttgtgacagattgcaggaaacagtcattgattt ttcaatattttaccttaaaattatttacagttgtaaccatggggaggtat tttcatgggctgtcagcccctgaaagactaggataatattccctgctctc tgacaagacaaattacctgtaatgagtgcagtagctgaagggtatacttt tattttaaaatatgtcaataaccccagtgactaaacgaatatgatttag cataatgaagcctgagtaacgtgaaaatgagcttttcaagggggcatggt aaagtctttcttttagctggttgtaagaagcttttgattctttttcagcc agctggtaggaatatagaattttataagcaaaccatcaggaatgatagtg ttgtttctgataagcaacatccaaatattttgaccctgcttttagtggtt tttttcaaatcttattttgagtcttacttttagtcatagaatagctactg atttgatgcggtctttaactgacttaatattttacaatttcaatatatt ttgcattggaatctccagtaatgaatattaaaatatatgtacaatcattt gtagatgatatcaattatattaagacatttcagatgggctattgtagtat ttaatgtgccgtattttatggtagaataattctcagtctctggacatcaa gattgctttcagtgggaatgaagattaatttacttcagtcctgattttt | 8570158 - 8568409 8567320- 8566974 |

TABLE 1-continued

LIST OF MOLECULE SEQUENCES

| SEQUENCE ID | FIG. 23 | Nucleotide sequence | Genomic Map Region - Human Chromosome 16 |
|---|---|---|---|
| | | aggcatcaatgcatgttttcattttgtcagacttttaccctcttttaat<br>gtaattctcaacttcttatggatttacttcccaatacataaaatccttca<br>aaacaagaatgataataattttatacttttataaaaataaatttattt<br>ttagtccatcaaggtgtctgaagattttatgcctaggtatctccatatct<br>aacttgataaggaaaataggataaacaatgctggtaatagcaggaaagta<br>agtatttgaataagatgtcaaactgatatttcatgtgaacctaactcatt<br>ttatggtaactaataattatcttatttaaatcaat<u>agg</u>taaaacctgttt<br>agaaattaaaaatgagttacgatttaaagaaaattcagatgactcattgt<br>gagtgct<u>agt</u>tctcttgt<u>agg</u>atgccactggaaatgttgaaatgaaaaat<br>attcagccgttggtctttgaaatttcctgtgatgtgtttcaatctagatg<br>caaagaacatggaaaaatcaaagtgctcgagtggtttaaatatgttttgg<br>gtattcctgtttatagactataatacttttccaattaaaatcctcagttg<br>tcacgcagaagaaggttaagctgtatttgattgccagttttactgaaaat<br>gcttagtattttacagtatcaccaaatatattttgtttagccaaggtata<br>ggaaaaataaaataaattgtataggttgacttttttctaaaatgtcttta<br>ttggattgaatgaatgtttatacctgaaaaaaaaggttcaaaaaaa | |
| SEQ ID NO: 30 | E2a - E3-<br>E5 - E7 | tctcggcgccagaggggcggggaggggcgggtctcgatcgcgctattgt<br>catggagacgggaagctggctgcagcggcggcggggaccgtggggccgag<br>gtggctgccagccggccaatgtctaagcgaggcggagcggcccaggcggc<br>ccgagcctgggggagcgcgcagccggccagtggcggcctcgccggcggcc<br>tcttcccgggctcgcagtaggcccgagtcgtcgccgggagctcctgggag<br>cagcgtccccgccctgctccctcgctcccgcctcttgcggcccacggc<br>ccctcagcgcccgcccccggctccgcccgccgcagccgcagcccctggcg<br>ctaacggtcggtaacggcccgcgcgcgccgcccgccggggctcgcgcca<br>gccacgagggagcgtccgcggcccgcgcgcccgcgcggcggaggagaggt<br>gttaagtgtgatgcttccataatacatttggatgctgtcagctaagttca<br>cttctgaactaagggggttcctccaaatgttggctgaaattcatcccaagg<br>ctggtctgcaaagtctgcaattcataatggagctactgtactggctattg<br>gaaggaggagattctgaagataaggagg<u>gt</u>aatattatctctcttttaaaaga<br>atactttcctctc<u>gt</u>aatcctgaatctttattacatgtaagaactttgtgc<br>agtagacagcaattctctttgaatttggtatatggaaacaattttatttc<br>ctctgctaagttttgagcctgcctcttctagtgccatggactgcattgg<br>tagagctgagaaatatcatttagccataactcagcaccccttaaaatagctt<br>cttctctgagaattagatctgtgaaggtgtcctgcacagttcttgtagatg<br>tcatttagtttgtggttgacgtgcatgcattgcatcctggctaatgtgt<br>tattgaaggtgttttcacgtaagcagttagaggaagcacttcaccccctat<br>tactaagttattaaaatgcctcctaaaggtagcattttaaattagtatac<br>ataattgattagtaatttgtcttctcccaagcataaaacagcatagcaga<br>gttaagtgtgaccagtgaagtataagatatagggattgatggtgacaat<br>gatcatagcaactaaatggatttttttttttctttt<u>ag</u>attcagccgttgg<br>tctttgaaatttcctgtgatgtgtttcaatctagatgcaaagaacatgga<br>aaaatcaaagtgctcgagtggtttaaatatgttttgggtattcctgttta<br>tagactataatacttttccaattaaaatcctcagttgtcacgcagaagaa<br>ggttaagctgtatttgattgccagttttactgaaaatgcttagtatttta<br>cagtatcaccaaatatattttgtttagccaaggtataggaaaaataaaat<br>aaattgtataggttgacttttttctaaaatgtctttattggattgaatga<br>atgtttatacctgaaaaaaaaggttcaaaaaaa | 8577328-<br>8576881<br>8573324-<br>8573212<br>8571761-<br>8571392<br>8567576-<br>8566974 |
| SEQ ID NO: 31 | E2a - E3-<br>E5a -<br>E6 - E7a | tctcggcgccagaggggcggggaggggcgggtctcgatcgcgctattgt<br>catggagacgggaagctggctgcagcggcggcggggaccgtggggccgag<br>gtggctgccagccggccaatgtctaagcgaggcggagcggcccaggcggc<br>ccgagcctgggggagcgcgcagccggccagtggcggcctcgccggcggcc<br>tcttcccgggctcgcagtaggcccgagtcgtcgccgggagctcctgggag<br>cagcgtccccgccctgctccctcgctcccgcctcttgcggcccacggc<br>ccctcagcgcccgcccccggctccgcccgccgcagccgcagcccctggcg<br>ctaacggtcggtaacggcccgcgcgcgccgcccgccggggctcgcgcca<br>gccacgagggagcgtccgcggcccgcgcgcccgcgcggcggaggagaggt<br>gttaagtgtgatgcttccataatacatttggatgctgtcagctaagttca<br>cttctgaactaagggggttcctccaaatgttggctgaaattcatcccaagg<br>ctggtctgcaaagtctgcaattcataatggagctactgtactggctattg<br>gaaggaggagattctgaagataaggaggtaaaacctgtttagaaattaaa<br>aatgagttacgatttaaagaaaattcagatgactcattgtgagtgct<u>agt</u><br>tctcttgt<u>agg</u>atgccactggaaatgttgaaatgaaaaatattcagccgt<br>tggtctttgaaatttcctgtgatgtgtttcaatctagatgcaaagaacat<br>ggaaaaatcaaagtgctcgagtggtttaaatatgttttgggtattcctgt<br>ttatagactataatacttttccaattaaaatcctcagttgtcacgcagaa<br>gaaggttaagctgtatttgattgccagttttactgaaaatgcttagtatt<br>ttacagtatcaccaaatatattttgtttagccaaggtataggaaaaataa<br>aataaattgtataggttgacttttttctaaaatgtctttattggattgaa<br>tgaatgtttatacctgaaaaaaaaggttcaaaaaaa | 8577328-<br>8576881<br>8573324-<br>8573212<br>8571761-<br>8571696<br>8568521-<br>8568409<br>8567320-<br>8566974 |

TABLE 2

SUMMARY OF END-POINT PCR BASED MEASUREMENT OF PREDICTED RNA VARIANTS DERIVED FROM SEQ ID NO: 1

|  | Non-diseased Controls | Adenoma | Adenocarcinoma |
|---|---|---|---|
| SEQ ID NO: 21 | 3 positive out of 30 | 19 positive out of 21 | 20 positive out of 21 |
| SEQ ID NO: 23 | 0 positive out of 2 | 3 positive out of 3 | 3 positive out of 3 |
| SEQ ID NO: 24 | 1 positive out of 30 | 15 positive out of 21 | 5 positive out of 21 |
| SEQ ID NO: 27 | 1 positive out of 30 | 11 positive out of 21 | 11 positive out of 21 |
| SEQ ID NO: 22 | 1 positive out of 30 | 6 positive out of 21 | 8 positive out of 21 |
| SEQ ID NO: 29 | 8 positive out of 30 | 18 positive out of 21 | 20 positive out of 21 |
| SEQ ID NO: 28 | 12 positive out of 30 | 18 positive out of 21 | 18 positive out of 21 |
| SEQ ID NO: 30 | 16 positive out of 30 | 20 positive out of 21 | 21 positive out of 21 |
| SEQ ID NO: 31 | 16 positive out of 30 | 21 positive out of 21 | 21 positive out of 21 |
| SEQ ID NO: 25 | 19 positive out of 30 | 20 positive out of 21 | 21 positive out of 21 |
| SEQ ID NO: 26 | 19 positive out of 30 | 20 positive out of 21 | 21 positive out of 21 |

TABLE 3

AFFYMETRIX HuGene Exon 1.0 PROBESETS TARGETING NUCLEOTIDE SEQUENCES IN SEQ ID NO: 1

| SEQ ID NO: 79 | PROBESET ID | TARGET SEQUENCE |
|---|---|---|
| SEQ ID NO: 76 | 3692517 | taaaatgtctttattggattgaatgaatgtttatacctga |
| SEQ ID NO: 77 | 3692518 | aggttaagctgtatttgattgccagttttactgaaaatgcttagtattttacagtatcaccaaatata |
| SEQ ID NO: 78 | 3692519 | aaatttcctgtgatgtgtttcaatctagatgcaaagaacatggaaaaatcaaagtgctcgagtggtttaaatatgtttt gggtattcctgtttatagactataatacttttccaattaaaatcctcagttgtcacgcaga |
| SEQ ID NO: 79 | 3692520 | gcctaagggtgtgacagatgatctctgtcacttgtcttagttgtgtcctgcaataaactggatgctttataaaatactagacctgtgatttcgtatgctgtaatatttcatttctccatcaccccctccaaattatttcttagtttggagtaaaataataaatgtattatagtcaacatctcttgaccccctctttagtttcagctaaactaagcatgtgtgtttgtgtgttcattttatagttcatgtgtagaactatgtgaattaaatttaagaaacatgtaaagtagaggaaatagttttctggagaaatttttccttttt ggatattatgcccttttccattgcttttctctgcttgaaagcaaaaaaaagtaccctaccccctgttctcctttagggaaaaactattcctataaagtatttttaaatcgtgcaagtcattgcctagggttagctaaaacatttctttttaaaaggagaaaatgccctggetttaacattttcttgtatttgtatctattaagataaacagtttactttgatacagtacataccaatctacttaattttttttccaggattccttttactatgtttggtctgacctttatgataacttaatatgggaacaaattagcatataattctattttccatgtgacctcaaccagttgcagaattgtaccactacttt agggggggcaatttgacagtttatgtagactatagcattaattgttcccaaatgttcagtgcatcctggctaatgtgttattgaaggtgttttcacgtaagcagttagaggaagcacttc |
| SEQ ID NO: 80 | 3692521 | gatgccactggaaatgttgaaatgaaaaat |
| SEQ ID NO: 81 | 3692522 | gaaaattcagatgactcattgtgagtgctagttc |
| SEQ ID NO: 82 | 3692523 | ttcaaggggcatggtaaagtctttcttttttagctggttgtaagaagcttttgattcttttcagccagctggtaggaatatagaattttataagcaaaccatcaggaatgatagtgttgtttctgataagcaacatccaaatattttgaccctgcttttagtggttttttcaaatcttattttgagtcttacttttagtcatagaatagctactgatttgatgcggtctttaactgacttaatattttta caatttcaatatattttgcattggaatctccagtaatgaatattaaaatatatgtacaatcatttgtagatgatatcaattatattaagacatttcag atgggctattgtagtatttaatgtgccgtattttatggtagaataattctcagtctctggacatcaagattgctttcagtgggaatgaagattaatttacttcagtcctgattttttaggcatcaatgcatgttttcatttttgtcagactttaccctctcttta atgtaattctcaacttcttatggatttacttcccaatacataaaatccttcaaaacaagaatgataataatttttatacttttata aaaataaattta ttttta gtccatcaaggtgtctg |
| SEQ ID NO: 83 | 3692524 | gcaattcataatggagctactgtactggctattgga |
| SEQ ID NO: 84 | 3692525 | gtgtgatgcttccataatacatttggatgctgtcagctaagttcacttctgaactaagg ggttcctccaaatgttggctgaaattcatcccaaggctggtctgc |
| SEQ ID NO: 85 | 3692526 | ccgaccagacgtcccgtgggctagggcctgggcctcgggccgcgtcggcgccggtcgagcctctccgggtgtcggggttcgggcgggcgcgtgggcgtggctcctctgtccacgcctgttccttcgtcgccgcggctctcgtccgggacacggctttccggagtagagccctt |

TABLE 3-continued

AFFYMETRIX HuGene Exon 1.0 PROBESETS TARGETING NUCLEOTIDE
SEQUENCES IN SEQ ID NO: 1

| SEQ ID NO: 79 | PROBESET ID | TARGET SEQUENCE |
|---|---|---|
| SEQ ID NO: 86 | 3692527 | aggtggctgccagccggccaatgtctaagcgaggcggagcggcccaggcggcccgagc<br>ctgggggagcgcgcagccggccagtggcggctcgccggcggcctcttcccgggctcg<br>cagtaggcccgagtcgtcgcccgggagctcctgggagcagcgtccccgccctgctcccc<br>tcgctcccgcctcttgcggccccacgcccctcagcgcccgccccggctccgccc<br>cgcagccgcagccctggcgctaacggtcggtaacgcccgcgcgcgccgcccgccgg<br>gggctcgcgccagccacgagggagcgtc |
| SEQ ID NO: 87 | 3692505 | ggcctgagcggttcagactacattctccgagagcccctgggtccgcccagcccagtgc<br>ctgacacctccttcacctatgattgggcgctggcct |
| SEQ ID NO: 88 | 3692504 | gtatagcacagcatcacaacctggatactgacattgatgcagtcaagacagagaacat<br>ttatatcatgaggaggatccctcattaccgcccctttgatatccacccctacttccaga<br>ccatctcactcctcccttaaccctggcaaccactagcatgttctccatttctataaat<br>ttgcctttataggaatgttatataattgcaattaaagtgtgtaaccttttggggtttg<br>actcaccggcatcattttctggagattcagcttatatgtgtca |

TABLE 4

| hCG_1815491 cDNA clones | | | |
|---|---|---|---|
| DB455235 | DB347418 | BU590179 | AI827680 |
| BQ638202 | AA581577 | AI004404 | BX096724 |
| BM920423 | AW173121 | DB222387 | W38547 |
| CN278390 | BF436749 | BM151589 | CN278219 |
| LOC388279 | BU737152 | DB349477 | AA928654 |
| XM_373688 | CA313804 | BF692451 | AI985612 |
| AI245732 | H89247 | BI561324 | BQ011371 |
| AW023444 | BE246152 | DB452125 | AI804090 |
| BM696001 | BI497216 | BU165627 | AI342725 |
| BU729242 | DB145524 | BU165662 | AW975944 |
| LOC650242 | DB143311 | BU569024 | AA746740 |
| XM_644116 | DA828150 | BF672570 | BU689926 |
| DB446128 | CN289138 | BU160166 | BG193316 |
| DB175550 | CN292893 | AW117234 | AA625672 |
| BM698708 | CV372409 | DB517664 | AI214681 |
| BI768666 | BF912258 | CB854553 | DW420944 |
| CD356299 | BE000458 | AI923595 | N90090 |
| CN288533 | CD000458 | AA825162 | CV575277 |
| CN275915 | AI903846 | BU180741 | BU625145 |
| CA436924 | BM150430 | BG720116 | DB520645 |
| BF679396 | DB372595 | BE504515 | AV725613 |
| CB217500 | AA829347 | AF275804 | |
| BQ002970 | AI242819 | AI204177 | |
| AA844729 | AA954994 | BM974647 | |

TABLE 5

OLIGONUCLEOTIDE PRIMERS

| Primer nucleotide sequence | Genomic map regions (start of primer) | Amplicon sequence confirmation |
|---|---|---|
| 5'-TAACTGGAATTCATGTTGGC TGAAATTCATCCCA (SEQ ID NO: 91) | 8573248=> | MULTIPLE AMPLICONS GENERATED. |
| 5'-CACGATAAGCTTTTATTATA GTCTATAAACAGGA ATACCCAAAACATATTTAA ACC (SEQ ID NO: 92) | <=88567198 | |
| 5'-ACACGGCTTTCCGGAGTAGA (SEQ ID NO: 93) | 8576635=> | SEQ21_ GACACGGCTTTCCGGAGTAGAGCCCTTGGAGGTGTTAAGTGTGATGCTTCCATAATACAT<br>::::::::::::::::::::::::::::::::::::::::::::::::::::::::::<br>PCR   GACACGGCTTTCCGGAGTAGAGCCCTTGGAGGTGTTAAGTGTGATGCTTCCATAATACAT |
| 5'-AACAGGTTTTACCTCCTTAT CTTCAGAA (SEQ ID NO: 94) | <=8571695 //8568521-8568509 | SEQ21_ TTGGATGCTGTCAGCTAAGTTCACTTCTGAACTAAGGGGTTCCTCCAAATGTTGGCTGAA<br>::::::::::::::::::::::::::::::::::::::::::::::::::::::::::<br>PCR   TTGGATGCTGTCAGCTAAGTTCACTTCTGAACTAAGGGGTTCCTCCAAATGTTGGCTGAA |
| | | SEQ21_ ATTCATCCCAAGGCTGGTCTGCAAAGTCTGCAATTCATAATGGAGCTACTGTACTGGCTA<br>::::::::::::::::::::::::::::::::::::::::::::::::::::::::::<br>PCR   ATTCATCCCAAGGCTGGTCTGCAAAGTCTGCAATTCATAATGGAGCTACTGTACTGGCTA |
| | | SEQ21_ TTGGAAGGAGGAGATTCTGAAGATAAGGAGGTAAAACCTGTT<br>::::::::::::::::::::::::::::::::::::::::<br>PCR   TTGGAAGGAGGAGATTCTGAAGATAAGGAGGTAAAACCTGTT |

TABLE 5-continued

OLIGONUCLEOTIDE PRIMERS

| Primer nucleotide sequence | Genomic map regions (start of primer) | Amplicon sequence confirmation |
|---|---|---|
| 5'-ACACGGCTTTCCGGAGTAGA (SEQ ID NO: 95) | 8576635=> | SEQ22_ ACACGGCTTTCCGGAGTAGAGCCCTTGGAGGTGTTAAGTGTGATGCTTCCATAATACATT<br>       :::::::::::::::::::::::::::::::::::::::::::::::::::::::::::<br>PCR    ACACGGCTTTCCGGAGTAGAGCCCTTGGAGGTGTTAAGTGTGATGCTTCCATAATACATT |
| 5'-GGCATCCTACAAGAGAACT CCTTATC (SEQ ID NO: 41) | <=8571695// 8568449- 8568433 | SEQ22_ TTGGATGCTGTCAGCTAAGTTCACTTCTGAACTAAGGGGTTCCTCCAAATGTTGGCTGAA<br>       :::::::::::::::::::::::::::::::::::::::::::::::::::::::::::<br>PCR    TTGGATGCTGTCAGCTAAGTTCACTTCTGAACTAAGGGGTTCCTCCAAATGTTGGCTGAA<br><br>SEQ22_ TTCATCCCAAGGCTGGTCTGCAAAGTCTGCAATTCATAATGGAGCTACTGTACTGGCTAT<br>       :::::::::::::::::::::::::::::::::::::::::::::::::::::::::::<br>PCR    TTCATCCCAAGGCTGGTCTGCAAAGTCTGCAATTCATAATGGAGCTACTGTACTGGCTAT<br><br>SEQ22_ TGGAAGGAGGAGATTCTGAAGATAAGGAGTTCTCTTGTAGGATGCC<br>       :::::::::::::::::::::::::::::::::::::::::::::<br>PCR    TGGAAGGAGGAGATTCTGAAGATAAGGAGTTCTCTTGTAGGATGCC |
| 5'-GGCGGAGGAGAGGTGAGC (SEQ ID NO: 97) | 8576892=> | Splice junction: SEQUENCE E2 & SEQUENCE E2b↓ |
| 5'-GCTGACAGCATCCA AATGTATTATG (SEQ ID NO: 96) | <=8573280 | SEQ23_ CAGCCACGAGGGAGCGTCCGCGGCCCGCGCGCCCGCGCGGCGGAGGAGAGGTG<br>                                              :::::::::::::::<br>PCR    -------------------------------------GGCGGAGGAGAGGTG<br><br>SEQ23_ AGCCCCGCCCGGGCCAGGCCCTCTGGCCGCGCCGTCCGCCCCTCTAGTCGTGTCCCCTC<br>       :::::::::::::::::::::::::::::::::::::::::::::::::::::::::::<br>PCR    AGCCCCGCCCGGGCCAGGCCCTCTGGCCGCGCCGTCCGCCCCTCTAGTCGTGTCCCCTC<br><br>SEQ23_ GTGGGCCGAACGGACGCGGCGGTGCCCCGCGCCCGACCAGACGTCCCGTGGGCTAGGGCC<br>       :::::::::::::::::::::::::::::::::::::::::::::::::::::::::::<br>PCR    GTGGGCCGAACGGACGCGGCGGTGCCCCGCGCCCGACCAGACGTCCCGTGGGCTAGGGCC<br><br>SEQ23_ TGGGCCTCGGGCCGCGTCGGCGCCGGTCGAGCCTCTCCGGGTGTCGGGGTTCGGGCGGG<br>       :::::::::::::::::::::::::::::::::::::::::::::::::::::::::::<br>PCR    TGGGCCTCGGGCCGCGTCGGCGCCGGTCGAGCCTCTCCGGGTGTCGGGGTTCGGGCGGG<br><br>SEQ23_ CGCGCGTGGGCGTGGCTCCTCTGTCCACGCCTGTTCCCTTCGTCGCCGCGGCTCTCGTCC<br>       :::::::::::::::::::::::::::::::::::::::::::::::::::::::::::<br>PCR    CGCGCGTGGGCGTGGCTCCTCTGTCCACGCCTGTTCCCTTCGTCGCCGCGGCTCTCGTCC<br><br>Splice juction: SEQUENCE E2b & SEQUENCE E3↓<br><br>SEQ23_ GGGACACGGCTTTCCGGAGTAGAGCCCTTGGAGGTGTTAAGTGTGATGCTTCCATAATAC<br>       :::::::::::::::::::::::::::::::::::::::::::::::::::::::::::<br>PCR    GGGACACGGCTTTCCGGAGTAGAGCCCTTGGAGGTGTTAAGTGTGATGCTTCCATAATAC<br><br>SEQ23_ ATTTGGATGCTGTCAGCTAAGTTCACTTCTGAACT<br>       :::::::::::::::::::<br>PCR    ATTTGGATGCTGTCAGC------------------ |
| 5'-TTTTTGAGAAGTGTATCATC TAGGAAGAA (SEQ ID NO: 45) | 8571884- 8571856 | SEQ24_ CTTTTTGAGAAGTGTATCATCTAGGAAGAAAATCAAATGGAGTATTGGTAATTAAATTGT<br>       :::::::::::::::::::::::::::::::::::::::::::::::::::::::::::<br>PCR    CTTTTTGAGAAGTGTATCATCTAGGAAGAAAATCAAATGGAGTATTGGTAATTAAATTGT |
| 5'-ACATATTTAAACCACTCGA GCACTTTG (SEQ ID NO: 46) | <=8567253- 8567226 | SEQ24_ AATTCCATGAAGGAAGGAAGTGGTGCAAAAGATGAAGCTAACTATTCCTGTTTTTCTTTT<br>       :::::::::::::::::::::::::::::::::::::::::::::::::::::::::::<br>PCR    AATTCCATGAAGGAAGGAAGTGGTGCAAAAGATGAAGCTAACTATTCCTGTTTTTCTTTT<br><br>SEQ24_ TAAGAGTCTGCAATTCATAATGGAGCTACTGTACTGGCTATTGGAAGGAGGAGATTCTGA<br>       :::::::::::::::::::::::::::::::::::::::::::::::::::::::::::<br>PCR    TAAGAGTCTGCAATTCATAATGGAGCTACTGTACTGGCTATTGGAAGGAGGAGATTCTGA<br><br>SEQ24_ AGATAAGGAGGTAAAACCTGTTTAGAAATTAAAAATGAGTTACGATTTAAAGAAAATTCA<br>       :::::::::::::::::::::::::::::::::::::::::::::::::::::::::::<br>PCR    AGATAAGGAGGTAAAACCTGTTTAGAAATTAAAAATGAGTTACGATTTAAAGAAAATTCA<br><br>SEQ24_ GATGACTCATTGTGAGTGCTAGTTCTCTTGTAGGATGCCACTGGAAATGTTGAAATGAAA<br>       :::::::::::::::::::::::::::::::::::::::::::::::::::::::::::<br>PCR    GATGACTCATTGTGAGTGCTAGTTCTCTTGTAGGATGCCACTGGAAATGTTGAAATGAAA |

TABLE 5-continued

OLIGONUCLEOTIDE PRIMERS

| Primer nucleotide sequence | Genomic map regions (start of primer) | Amplicon sequence confirmation | |
|---|---|---|---|
| | | SEQ24_ | AATATTCAGCCGTTGGTCTTTGAAATTTCCTGTGATGTGTTTCAATCTAGATGCAAAGAA |
| | | | :::::::::::::::::::::::::::::::::::::::::::::::::::::::::::: |
| | | PCR | AATATTCAGCCGTTGGTCTTTGAAATTTCCTGTGATGTGTTTCAATCTAGATGCAAAGAA |
| | | SEQ24_ | CATGGAAAAATCAAAGTGCTCGAGTCCTTTAAATATGT |
| | | | :::::::::::::::::::::::::::::::::::::: |
| | | PCR | CATGGAAAAATCAAAGTGCTCGAGTGGTTTAAATATGT |
| 5'-CAGCCACGAGGGAGCGT (SEQ ID NO: 98) | 8576931=> | SEQ25_ | CAGCCACGAGGGAGCGTCCGCGGCCCGCGCGCCCGCGCGGCGGAGGAGAGGTGTTAAGTG |
| | | | ::::::::::::::::::::::::::::::::::::::::::::::::::::::::::: |
| | | PCR | CAGCCACGAGGGAGCGTCCGCGGCCCGCGCGCCCGCGCGGCGGAGGAGAGGTGTTAAGTG |
| 5'-GGATCGACTCCACATACAAGCA (SEQ ID NO: 49) | <=8573192-8573170 | SEQ25_ | TGATGCTTCCATAATACATTTGGATGCTGTCAGCTAAGTTCACTTCTGAACTAAGGGGTT |
| | | | :::::::::::::::::::::::::::::::::::::::::::::::::::::::::::: |
| | | PCR | TGATGCTTCCATAATACATTTGGATGCTGTCAGCTAAGTTCACTTCTGAACTAAGGGGTT |
| | | SEQ25_ | CCTCCAAATGTTGGCTGAAATTCATCCCAAGGCTGGTCTGCAAGTGAGTGTCTGCACACA |
| | | | :::::::::::::::::::::::::::::::::::::::::::::::::::::::::::: |
| | | PCR | CCTCCAAATGTTGGCTGAAATTCATCCCAAGGCTGGTCTGCAAGTGAGTGTCTGCACACA |
| | | SEQ25_ | GTTTGCTTGTATGTGGAGTCGATCC |
| | | | ::::::::::::::::::::::::: |
| | | PCR | GTTTGCTTGTATGTGGAGTCGATCC |
| 5'-ATGTTGGCTGAAATTCATCCCA (SEQ ID NO: 52) | 8573247=> | SEQ26_ | ATGTTGGCTGAAATTCATCCCAAGGCTGGTCTGCAAAGTCTGCAATTCATAATGGAGCTA |
| | | | :::::::::::::::::::::::::::::::::::::::::::::::::::::::::::: |
| | | PCR | ATGTTGGCTGAAATTCATCCCAAGGCTGGTCTGCAAAGTCTGCAATTCATAATGGAGCTA |
| 5'-TTCCAGTGGCATCCTCCTTATC (SEQ ID NO: 53) | <=8571696 // 8568437-8568425 | SEQ26_ | CTGTACTGGCTATTGGAAGGAGGAGATTCTGAAGATAAGGAGGATGCCACTGGAA |
| | | | :::::::::::::::::::::::::::::::::::::::::::::::::::::: |
| | | PCR | CTGTACTGGCTATTGGAAGGAGGAGATTCTGAAGATAAGGAGGATGCCACTGGAA |
| 5'-ATGTTGGCTGAAATTCATCCCA (SEQ ID NO: 56) | 8573247=> | SEQ27_ | ATGTTGGCTGAAATTCATCCCAAGGCTGGTCTGCAATTACCTATTTCTTTTAAGAATAAA |
| | | | :::::::::::::::::::::::::::::::::::::::::::::::::::::::::::: |
| | | PCR | ATGTTGGCTGAAATTCATCCCAAGGCTGGTCTGCAATTACCTATTTCTTTTAAGAATAAA |
| 5'-TCTGTGTGTACTCTGTCACTAAAAAAGTTTT (SEQ ID NO: 57) | <=5872712 | SEQ27_ | TTTAGTGGGAATATCAGTTCCAGTCATGGGTACCAAACTTTTTTAGTGACAGAGTACACA |
| | | | :::::::::::::::::::::::::::::::::::::::::::::::::::::::::::: |
| | | PCR | TTTAGTGGGAATATCAGTTCCAGTCATGGGTACCAAACTTTTTTAGTGACAGAGTACACA |
| | | SEQ27_ | CAGA |
| | | | :::: |
| | | PCR | CAGA |
| 5'-TAAGATATTAGGGATTGATGGTGACAA (SEQ ID NO: 60) | 8567385=> | SEQ28_ | TAAGATATTAGGGATTGATGGTGACAATGATCATAGCAACTAAATGGATTTTTTTTTCT |
| | | | ::::::::::::::::::::::::::::::::::::::::::::::::::::::::: : |
| | | PCR | TAAGATATTAGGGATTGATGGTGACAATGATCATAGCAACTAAATGGATTTTTTTT-CT |
| 5'-ACATATTTAAACCACTCGAGCACTTTG (SEQ ID NO: 61) | <=8567226 | SEQ28_ | TTTAGATTCAGCCGTTGGTCTTTGAAATTTCCTGTGATGTGTTTCAATCTAGATGCAAAG |
| | | | :::::::::::::::::::::::::::::::::::::::::::::::::::::::::::: |
| | | PCR | TTTAGATTCAGCCGTTGGTCTTTGAAATTTCCTGTGATGTGTTTCAATCTAGATGCAAAG |
| | | SEQ28_ | AACATGGAAAAATCAAAGTGCTCGAGTGGTTTAAATATGT |
| | | | :::::::::::::::::::::::::::::::::::::::: |
| | | PCR | AACATGGAAAAATCAAAGTGCTCGAGTGGTTTAAATATGT |
| 5'-TGCCTAGGTATCTCCATATCTAACTTGA (SEQ ID NO: 64) | 8568679=> | SEQ29_ | TGCCTAGGTATCTCCATATCTAACTTGATAAGGAAAATAGGATAAACAATGCTGGTAATA |
| | | | :::::::::::::::::::::::::::::::::::::::::::::::::::::::::::: |
| | | PCR | TGCCTAGGTATCTCCATATCTAACTTGATAAGGAAAATAGGATAAACAATGCTGGTAATA |
| 5'-ACATATTTAAACCACTCGAGCACTTTG (SEQ ID NO: 65) | <=8567226 | SEQ29_ | GCAGGAAAGTAAGTATTTGAATAAGATGTCAAACTGATATTTCATGTGAACCTAACTCAT |
| | | | :::::::::::::::::::::::::::::::::::::::::::::::::::::::::::: |
| | | PCR | GCAGGAAAGTAAGTATTTGAATAAGATGTCAAACTGATATTTCATGTGAACCTAACTCAT |
| | | SEQ29_ | TTTATGGTAACTAATAATTATCTTATTTAAATCAATAGGTAAAACCTGTTTAGAAATTAA |
| | | | :::::::::::::::::::::::::::::::::::::::::::::::::::::::::::: |
| | | PCR | TTTATGGTAACTAATAATTATCTTATTTAAATCAATAGGTAAAACCTGTTTAGAAATTAA |
| | | SEQ29_ | AAATGAGTTACGATTTAAAGAAAATTCAGATGACTCATTGTGAGTGCTAGTTCTCTTGTA |
| | | | :::::::::::::::::::::::::::::::::::::::::::::::::::::::::::: |
| | | PCR | AAATGAGTTACGATTTAAAGAAAATTCAGATGACTCATTGTGAGTGCTAGTTCTCTTGTA |

TABLE 5-continued

OLIGONUCLEOTIDE PRIMERS

| Primer nucleotide sequence | Genomic map regions (start of primer) | Amplicon sequence confirmation | |
|---|---|---|---|
| | | SEQ29_ | GGATGCCACTGGAAATGTTGAAATGAAAAATATTCAGCCGTTGGTCTTTGAAATTTCCTG |
| | | | :::::::::::::::::::::::::::::::::::::::::::::::::::::::::::: |
| | | PCR | GGATGCCACTGGAAATGTTGAAATGAAAAATATTCAGCCGTTGGTCTTTGAAATTTCCTG |
| | | SEQ29_ | TGATGTGTTTCAATCTAGATGCAAAGAACATGGAAAAATCAAAGTGCTCGAGTGGTTTAA |
| | | | :::::::::::::::::::::::::::::::::::::::::::::::::::::::::::: |
| | | PCR | TGATGTGTTTCAATCTAGATGCAAAGAACATGGAAAAATCAAAGTGCTCGAGTGGTTTAA |
| | | SEQ29_ | ATATGT |
| | | | :::::: |
| | | PCR | ATATGT |
| 5'-ATGTTGGCTGAAATTCATCC CA (SEQ ID NO: 68) | 8573247=> | SEQ30_ | ATGTTGGCTGAAATTCATCCCAAGGCTGGTCTGCAAAGTCTGCAATTCATAATGGAGCTA |
| | | | :::::::::::::::::::::::::::::::::::::::::::::::::::::::::::: |
| | | PCR | ATGTTGGCTGAAATTCATCCCAAGGCTGGTCTGCAAAGTCTGCAATTCATAATGGAGCTA |
| 5'-TGCTGAGTATGGCTAAATG ATATTTCTC (SEQ ID NO: 69) | <=8571488 | SEQ30_ | CTGTACTGGCTATTGGAAGGAGGAGATTCTGAAGATAAGGAGGTAATATTATCTCTTTTA |
| | | | :::::::::::::::::::::::::::::::::::::::::::::::::::::::::::: |
| | | PCR | CTGTACTGGCTATTGGAAGGAGGAGATTCTGAAGATAAGGAGGTAATATTATCTCTTTTA |
| | | SEQ30_ | AAAGAATACTTTCCTCTGTAATCCTGAATCTTTATTACATGTAAGAACTTTGTGCAGTAG |
| | | | :::::::::::::::::::::::::::::::::::::::::::::::::::::::::::: |
| | | PCR | AAAGAATACTTTCCTCTGTAATCCTGAATCTTTATTACATGTAAGAACTTTGTGCAGTAG |
| | | SEQ30_ | ACAGCAATTTCTTTGAATTTGGTATATGGAAACAATTTTATTTTCCTCTGCTAAGTTTTT |
| | | | :::::::::::::::::::::::::::::::::::::::::::::::::::::::::::: |
| | | PCR | ACAGCAATTTCTTTGAATTTGGTATATGGAAACAATTTTATTTTCCTCTGCTAAGTTTTT |
| | | SEQ30_ | GAGCCTGCCTCTTCTAGTGCCATGGACTGCATTGGTAGAGCTGAGAAATATCATTTAGCC |
| | | | :::::::::::::::::::::::::::::::::::::::::::::::::::::::::::: |
| | | PCR | GAGCCTGCCTCTTCTAGTGCCATGGACTGCATTGGTAGAGCTGAGAAATATCATTTAGCC |
| | | SEQ30_ | ATACTCAGCA |
| | | | :::::::::: |
| | | PCR | ATACTCAGCA |
| 5'-CAGCCACGAGGGAGCGT (SEQ ID NO: 72) | 8568679=> | SEQ31_ | AGCCACGAGGGAGCGTCCGCGGCCCGCGCGCCCGCGCGGCGGAGGAGAGGTGTTAAGTGT |
| | | | :::::::::::::::::::::::::::::::::::::::::::::::::::::::::::: |
| | | PCR | AGCCACGAGGGAGCGTCCGCGGCCCGCGCGCCCGCGCGGCGGAGGAGAGGTGTTAAGTGT |
| 5'-AACAGGTTTTACCTCCTTAT CTTCAGAA (SEQ ID NO: 73) | <=8571695 // 8568521- 8568510 | SEQ31_ | GATGCTTCCATAATACATTTGGATGCTGTCAGCTAAGTTCACTTCTGAACTAAGGGGTTC |
| | | | :::::::::::::::::::::::::::::::::::::::::::::::::::::::::::: |
| | | PCR | GATGCTTCCATAATACATTTGGATGCTGTCAGCTAAGTTCACTTCTGAACTAAGGGGTTC |
| | | SEQ31_ | CTCCAAATGTTGGCTGAAATTCATCCCAAGGCTGGTCTGCAAAGTCTGCAATTCATAATG |
| | | | :::::::::::::::::::::::::::::::::::::::::::::::::::::::::::: |
| | | PCR | CTCCAAATGTTGGCTGAAATTCATCCCAAGGCTGGTCTGCAAAGTCTGCAATTCATAATG |
| | | SEQ31_ | GAGCTACTGTACTGGCTATTGGAAGGAGGAGATTCTGAAGATAAGGAGGTAAAACCTGTT |
| | | | :::::::::::::::::::::::::::::::::::::::::::::::::::::::::::: |
| | | PCR | GAGCTACTGTACTGGCTATTGGAAGGAGGAGATTCTGAAGATAAGGAGGTAAAACCTGTT |

BIBLIOGRAPHY

Alon et al., *Proc. Natl. Acad. Sci. USA:* 96, 6745-6750, June 1999

Ausubel, F. et al., "Current Protocols in Molecular Biology", John Wiley & Sons, (1998)

Bonner et al (1973) *J Mol. Biol.* 81:123

DeRisi, et al., *Nature Genetics* 14:457-460 (1996)

Germer et al., *Genome Res.* 10:258-266 (2000)

Guo et al., *Nucleic Acids Res.* 22:5456-5465 (1994)

Heid et al., *Genome Res.* 6:986-994 (1996)

Kraus, M. and Aaronson, S., 1991. *Methods Enzymol.,* 200:546-556

Maskos and Southern, *Nuc. Acids Res.* 20:1679-84, 1992

Moore et al., *BBA,* 1402:239-249, 1988

Nielsen (1999) *Curr. Opin. Biotechnol.* 10:71-75

Nielsen et al. (1991) *Science* 254: 1497-1500

Pease et al., *Proc. Natl. Acad Sci. USA* 91(11):5022-5026 (1994)

Pevzner et al., *J. Biomol. Struc. & Dyn.* 9:399-410, 1991

Schena, et al. *Science* 270:467-470 (1995)

Smith et al., *Science* 258:1122-1126 (1992)

T. Sano and C. R. Cantor, *Bio/Technology* 9:1378-81 (1991)

Urdea et al., *Nucleic Acids Symp. Ser.,* 24:197-200 (1991)

Wedemeyer et al., *Clinical Chemistry* 48:9 1398-1405, 2002)

Weissleder et al., *Nature Medicine* 6:351-355, 2000

The invention claimed is:

1. A method, comprising measuring the level of expression of one or more mRNA transcripts in a biological sample from a subject, which transcripts comprise an RNA sequence characterised by a sequence selected from the group consisting of:
  (i) SEQ ID NO:21, or a sequence having at least 98% similarity across the length of SEQ ID NO:21;
  (ii) SEQ ID NO:22, or a sequence having at least 98% similarity across the length of SEQ ID NO:22;
  (iii) SEQ ID NO:24, or a sequence having at least 98% similarity across the length of SEQ ID NO:24;
  (iv) SEQ ID NO:25, or a sequence having at least 98% similarity across the length of SEQ ID NO:25;
  (v) SEQ ID NO:27, or a sequence having at least 98% similarity across the length of SEQ ID NO:27;
  (vi) SEQ ID NO:28, or a sequence having at least 98% similarity across the length of SEQ ID NO:28;
  (vii) SEQ ID NO:29, or a sequence having at least 98% similarity across the length of SEQ ID NO:29;
  (viii) SEQ ID NO:30, or a sequence having at least 98% similarity across the length of SEQ ID NO:30; and
  (ix) SEQ ID NO:31, or a sequence having at least 98% similarity across the length of SEQ ID NO:31.

2. The method according to claim 1 wherein said level of expression is the level of mRNA.

3. The method according to claim 1 wherein said at least 98% similarity is 98% or 99%.

4. The method according to claim 1 wherein said level of expression is assessed by analysing RNA expression.

5. A method comprising measuring the level of expression of an RNA transcript in a biological sample from a subject, which transcript comprises one or more exon segments selected from the group consisting of:
  (i) an exon segment defined by SEQ ID NO:5, or a sequence having at least 98% similarity across the length of SEQ ID NO:5;
  (ii) an exon segment defined by SEQ ID NO:6, or a sequence having at least 98% similarity across the length of SEQ ID NO:6;
  (iii) an exon segment defined by SEQ ID NO:7, or a sequence having at least 98% similarity across the length of SEQ ID NO:7;
  (iv) an exon segment defined by SEQ ID NO:8, or a sequence having at least 98% similarity across the length of SEQ ID NO:8;
  (v) an exon segment defined by SEQ ID NO:9, or a sequence having at least 98% similarity across the length of SEQ ID NO:9;
  (vi) an exon segment defined by SEQ ID NO: 10, or a sequence having at least 98% similarity across the length of SEQ ID NO: 10;
  (vii) an exon segment defined by SEQ ID NO: 11, or a sequence having at least 98% similarity across the length of SEQ ID NO:11;
  (viii) an exon segment defined by SEQ ID NO: 12, or a sequence having at least 98% similarity across the length of SEQ ID NO:12;
  (ix) an exon segment defined by SEQ ID NO: 14, or a sequence having at least 98% similarity across the length of SEQ ID NO: 14;
  (x) an exon segment defined by SEQ ID NO: 15, or a sequence having at least 98% similarity across the length of SEQ ID NO: 15;
  (xi) an exon segment defined by SEQ ID NO: 16, or a sequence having at least 98% similarity across the length of SEQ ID NO: 16;
  (xii) an exon segment defined by SEQ ID NO: 17, or a sequence having at least 98% similarity across the length of SEQ ID NO: 17; and
  (xiii) an exon segment defined by SEQ ID NO: 18, or a sequence having at least 98% similarity across the length of SEQ ID NO: 18; and
  (xiv) an exon segment defined by SEQ ID NO:4, or a sequence having at least 98% similarity across the length of SEQ ID NO:4.

6. The method according to claim 5 wherein said level of expression is the level of mRNA.

7. A method comprising measuring the level of expression of an RNA transcript in a biological sample from a subject wherein said transcript is selected from the group consisting of:
  (i) an RNA transcript which comprises each of the exon segments defined by SEQ ID NO:5, SEQ ID NO:6, SEQ ID NO:10 and SEQ ID NO:12, or a sequence having at least 98% similarity across the length of SEQ ID NO:6, SEQ ID NO:10 or SEQ ID NO:12;
  (ii) an RNA transcript which comprises each of the exon segments defined by SEQ ID NO:5, SEQ ID NO:6, SEQ ID NO: 10 and SEQ ID NO: 14, or a sequence having at least 98% similarity across the length of SEQ ID NO:5, SEQ ID NO:6, SEQ ID NO:10 or SEQ ID NO:14;
  (iii) an RNA transcript which comprises each of the exon segments defined by SEQ ID NO: 11, SEQ ID NO: 12 and SEQ ID NO: 18, or a sequence having at least 98% similarity across the length of SEQ ID NO:11, SEQ ID NO:12 or SEQ ID NO: 18;
  (iv) an RNA transcript which comprises each of the exon segments defined by SEQ ID NO:4 and SEQ ID NO:7, or a sequence having at least 98% similarity across the length of SEQ ID NO:4 or SEQ ID NO:7;
  (v) an RNA transcript which comprises each of the exon segments defined by SEQ ID NO:6 and SEQ ID NO:8, or a sequence having at least 98% similarity across the length of SEQ ID NO:6 or SEQ ID NO:8;
  (vi) an RNA transcript which comprises each of the exon segments defined by SEQ ID NO: 4, SEQ ID NO: 6, SEQ ID NO: 8, SEQ ID NO: 10 and SEQ ID NO: 12, or a sequence having at least 98% similarity across the length of SEQ ID NO: 4, SEQ ID NO: 6, SEQ ID NO: 8, SEQ ID NO: 10 or SEQ ID NO: 12;
  (vii) an RNA transcript which comprises each of the exon segments defined by SEQ ID NO: 15 and SEQ ID NO: 18, or a sequence having at least 98% similarity across the length of SEQ ID NO: 15 or SEQ ID NO: 18;

(viii) an RNA transcript which comprises each of the exon segments defined by SEQ ID NO:6 and SEQ ID NO:9, or a sequence having at least 98% similarity across the length of SEQ ID NO:6 or SEQ ID NO:9; and (ix) an RNA transcript which comprises each of the exon segments defined by SEQ ID NO:4, SEQ ID NO:6, SEQ ID NO: 10 and SEQ ID NO: 12, or a sequence having at least 98% similarity across the length of SEQ ID NO:4, SEQ ID NO:6, SEQ ID NO: 10 or SEQ ID NO:12.

8. The method according to claim 7 wherein said level of expression is the level of mRNA.

9. A method comprising measuring the level of expression of an RNA transcript in a biological sample from a subject, wherein the transcript comprises an exon segment defined by SEQ ID NO: 6 and an exon segment defined by SEQ ID NO: 18.

10. The method according to claim 9 wherein said level of expression is the level of mRNA.

11. A method of measuring the level of expression of one or more mRNA transcripts in a biological sample from a subject, which transcripts comprise an RNA sequence characterized by a sequence selected from the group consisting of:

(i) SEQ ID NO:21;
(ii) SEQ ID NO:22;
(iii) SEQ ID NO:24;
(iv) SEQ ID NO:25;
(v) SEQ ID NO:27;
(vi) SEQ ID NO:28;
(vii) SEQ ID NO:29;
(viii) SEQ ID NO:30; and
(ix) SEQ ID NO:31, said method comprising contacting the sample with one or more nucleic acid probes or primers, wherein the one or more nucleic acid probes or primers hybridize to said RNA sequence in said one or more mRNA transcripts; and detecting hybridization of the one or more nucleic acid probes or primers to the one or more mRNA transcripts in the sample to determine the level of expression of the one or more mRNA transcripts.

12. The method of claim 11, wherein the one or more nucleic acid probes or primers include a nucleic acid probe or primer that hybridizes to an RNA sequence comprising a nucleotide sequence selected from the group consisting of SEQ ID NO: 4, SEQ ID NO: 6, SEQ ID NO: 10, SEQ ID NO: 12 and SEQ ID NO: 18.

13. A method of measuring the level of expression of one or more mRNA transcripts in a biological sample from a subject, which transcripts comprise an RNA sequence characterized by a sequence selected from the group consisting of:

(i) SEQ ID NO:21;
(ii) SEQ ID NO:22;
(iii) SEQ ID NO:24;
(iv) SEQ ID NO:25;
(v) SEQ ID NO:27;
(vi) SEQ ID NO:28;
(vii) SEQ ID NO:29;
(viii) SEQ ID NO:30; and
(ix) SEQ ID NO:31, said method comprising contacting the sample with one or more nucleic acid probes or primers, wherein the one or more nucleic acid probes or primers hybridize to said RNA sequence in said one or more mRNA transcripts under stringency conditions that comprise washing in a solution for 15 minutes at 68° C., and wherein the solution is pre-warmed to 68° C., and wherein the solution contains 0.1×SSC/0.1% SDS; and detecting hybridization of the one or more nucleic acid probes or primers to the one or more mRNA transcripts in the sample to determine the level of expression of the one or more mRNA transcripts.

* * * * *

SEQUENCE LISTING

<160> NUMBER OF SEQ ID NOS: 98

<210> SEQ ID NO 1
<211> LENGTH: 17009
<212> TYPE: DNA
<213> ORGANISM: Homo Sapiens

<400> SEQUENCE: 1

| | | | | | |
|---|---|---|---|---|---|
| tggccacaca | cgggcatggg | gcgcgccgcg | ccgcggccgc | caacgagccg | ggcggcgccc | 60 |
| tgcgagggcg | agcgggcggg | cacctggcct | ctggctgccc | tgggccgccg | ctcctctggc | 120 |
| cccggctccg | gggctccggc | ccgcggcgcc | tcctcgctgg | cttcccgcgc | gcctccggct | 180 |
| gcgaccgccg | cgcccgctcc | tctgcgcgcc | tcgctcgccc | cagctgggct | tttttttccc | 240 |
| tcccctcccc | tcccttgctg | ctttctcttt | ttcccctcg | ctctttgcac | cgggggggctc | 300 |
| tgcttttgcc | tttgcaaagg | tcctgccaag | atgctaagtt | ggaaattgag | gattctgacg | 360 |
| ccttgtgcgc | gcccgaagct | cctccttccc | ggggtgtagt | cggtgggagg | actggcagga | 420 |
| gcttctgggc | ggccgcagcc | aacccggccg | ccaggcgcgc | ctcgccctct | ccctcttcct | 480 |
| cctcggctct | ctctcccgct | cgctggcgct | cctctcgccc | ctccctagcg | cccgcctccc | 540 |
| ctccgcggcc | cccctctca | ccctcctct | ttgcctcccc | ttttcccctc | cccggtctct | 600 |
| ccctctctct | cgctttctct | cagactctcg | agcgccggcc | ccaggatgac | aatcacatcc | 660 |
| caggagcgcc | gatctcttcc | aactttcctc | ttctgctaac | tcggggcgga | gtggcagtcc | 720 |
| cgccgccccg | aagcacaaag | ggaacgaggc | gcgggctgt | gcgccggcga | acgctctgcg | 780 |
| ctctcctagc | cacagtagat | cgcggactta | gcggatttct | tgttctccgg | caggctgggc | 840 |
| tccgaggcca | ttcgttgccc | accccctct | ggcgtcttcc | ccaagccagg | gggcccggag | 900 |
| agccagctgg | agatccggaa | tgaaagtctc | tgggagagcc | gatggatggc | ccgcgcccag | 960 |
| ggcgcaggaa | gtccgggatg | actgcccctc | tgcgccggca | gcagcaggtg | ggcgagagac | 1020 |
| aggcctcaga | cgtctgcacg | tctccgcctc | gccttccttc | taccgacccc | ccgccggacg | 1080 |
| gcgagggaga | agacactggt | tcctggaact | accggggtag | ccttttttcta | gagtaggggt | 1140 |
| ggtgggcaag | aactgccaga | cagagaatca | gctacacccg | aggagatctc | gggaccgtcc | 1200 |
| ccagctccac | tcccacgcct | cgcagcctct | ttctcccggt | tttcccaccg | cacgcagctc | 1260 |
| gcaccgccaa | gtcggtggtg | gtggagggtg | cgggtcccct | tcccttttgt | ttaactaagt | 1320 |
| cgccttcccc | ttcgcacgca | ctctcgcatc | cgcccacgct | ccactgcaaa | cactgggcag | 1380 |
| agcagtgccc | aacccaacca | ctgtttgttc | agcgaggcgc | tggcgaagca | aacacacaca | 1440 |
| actgagtcag | aggcagagcc | cttgcccacg | acggccacac | agttagaata | caaaacagac | 1500 |
| cctctcctct | tctctccacc | tcccgccacc | acaagccacg | gacgcactcg | aactctggga | 1560 |
| cagacagggg | cgctggtgaa | ccaggacaga | agatggcaca | ggtttgggca | cgccgcggaa | 1620 |
| gctcgggata | tcgggaactt | cgcataatgg | ggccacacgc | aagccgaagc | ataactatat | 1680 |
| acaaagtttc | tcgcattgac | tttgacgggc | gagatgtact | ttatttcgcg | atctcacact | 1740 |
| aacccagcgc | cgcaccggca | cccgctcggt | gctgcgctct | cgtgcacgcg | cgttggctcc | 1800 |
| tccctccgt | ctgctcccct | ccccagaca | ccgcccacca | agaggcctga | gcggttcaga | 1860 |
| ctacattctc | cgagagcccc | tgggtccgcc | cagcccagtg | cctgacacct | ccttcaccta | 1920 |
| tgattgggcg | ctggcctccc | tgggctccgc | ccctggtga | cgtaacccg | ctttcctccg | 1980 |
| agtctcggcg | ccagagggc | ggggaggggc | gggtctcga | tcgcgctatt | gtcatggaga | 2040 |
| cgggaagctg | gctgcagcgg | cggcgggac | cgtgggccg | aggtggctgc | cagccggcca | 2100 |

```
atgtctaagc gaggcggagc ggcccaggcg gcccgagcct gggggagcgc gcagccggcc    2160
agtggcggcc tcgccggcgg cctcttcccg ggctcgcagt aggcccgagt cgtcgccggg    2220
agctcctggg agcagcgtcc ccgccctgct cccctcgctc ccgcctcttg cggcccacg     2280 gcccctcagc gcccgccccc ggctccgccc gccgcagccg cagcccctgg cgctaacggt    2340
cggtaacggc ccgcgcgcgc cgccgccgg gggctcgcgc cagccacgag ggagcgtccg     2400
cggcccgcgc gcccgcgcgg cggaggagag gtgagccccc gcccgggcca ggccctctgg    2460
ccgcgccgtc cgcccctcta gtcgtgtccc ctcgtgggcc gaacggacgc ggcggtgccc    2520
cgcgcccgac cagacgtccc gtgggctagg gcctgggcct cgggccgcgt cggcgccggt    2580
cgagcctctc cgggtgtcgg ggttcggggc gggcgcgcgt gggcgtggct cctctgtcca    2640
cgcctgttcc cttcgtcgcc gcggctctcg tccgggacac ggcttccgg agtagagccc     2700 ttggaggttt gtgccaccga aacccgagt ctgtcacaca gacatcctca ttacatcatc     2760
ctgccactcc ggcagtcccg cgcttttctcc ccccaccccc gccccgccc cgccccgc      2820 cccgtggctt gtttgttggt tgtttttttta atttttttaa cccctttttct tgtactgtct  2880 tcttttggt gtcaggggct ggagagactc ctgcaagata ttgaggcatt tagaatgtat     2940
ggttctgttg ccgtggttgt cacctccgct ctacgccaaa tttaagactc atttcttaag    3000
gatgtctcta ttttctgctt tatttgcaca ttgatggctc tgctgctcag ctggccacgg    3060
ccgcccggcg tctgagatag aattgtgtta atatgagaaa gggaacggcc gatcatgatt    3120
agcaggcaga cggcatgcag atagcatctg gcgggttttc tccgttttta tatgaaagcg    3180
ttcacttgtt tgctggtaaa cacgaggttt taacttttta tctgggtagt ggtgaccgtt    3240
tgtttcactc tcccctcctt tttacttcct attcattagc ttttccgttt ggaaagctgc    3300
atacttgtta gcggtagttt ggtgtcttga ctctgaagct ttctcttcca gcagaggtgg    3360
gatctgtatc cctcccatcc taggttacca agaagacttt ttctcccctt actttctatt    3420
gaatttgtgt ctttcccaac atttaaactt acactaggga taagtttgct cgggttgttt    3480
ttgacgtagg actattaaat attctcattt tgaaacttcc taaaggttta ttggtttgtc    3540
atgtctgcac cgatccagtt tcgcataact cttaaaattt aaagctttaa agtacggttc    3600
gcaattgtat tgtcaagaca tggccctaga gcttgttctt caagttttgg ctgtacagtt    3660
gtcattgttt cagtcaagtg caaaagaggt tattcctgtt tatttagtgt taatagctat    3720
ttacagttaa aactttaaag actcatagaa gtaggtctgc tgtatttaa agatctcatc     3780 attcttgtgg gagagacaca acaccaacac caggaaaggc aacagattgc ttctgtcata    3840
tcgctttgct gttttggagt gtacttaaag gattatgatt gataaggctg tcttgccaga    3900
gaatgttgac acaggtgtgc atcgttatct taattaagat cctgagaaaa tgttgtctat    3960
aaatggtgac ataagaaggg cggcatattt ttgtacagtt ttgcttttgg agaatttaat    4020
tgcacttgaa acctgtcttt gagcttccag attttgtgag cacttagca acagaagttt     4080 tagagagaaa tgatagttta atgttaagtg ttctggcatg tactaatact acttgtggct    4140
ttttggcaat gcctgtgtcg gctttctttg tgctctacct ttgtggaata atggtttcta    4200
attttgaaag aaaagcataa aatagagcag tattttatta agcaaacact tgttagtgtt    4260
cagaataagt ctgtagagga gggcatgctt aatgtgcaga aacaggaata taataagagg    4320
taaatatatg agaaatttat gctatttcgt ttttttggaa aagaaacagt ctccgtggggt   4380 gccttaatga tctaaaacaa tttctttttc atatcattaa atacctagat acaatgttta    4440
```

```
cggaatgcct tgttttatt tctaaaaata gaagaaaact gttttatttc ttccaaaata    4500
ctgttctgtg tgtttgaatt gatgagtaag tgaagatagt gcatttagtc tcttactagt    4560
ttaaggatct gagtcataac ctgggtgacc actaaaataa tattgctgtt ctttactaca    4620
aatctcggaa tgcaaaaaca ctggcaagat ggatgctgtt gatgatatta cccttggctt    4680
acccagcacc taatacctttt taacataagt attgcattaa gattttctct tctctttgta    4740
gcttaggatt tcctggaagc tggctgtcta tcagtgtgta tgtaagaagt gtgtatgttt    4800
ttctttaata ttaaaagtca ctgtaaaaag aggaaatgaa agtggaggag accataggca    4860
tatgatcgga aaagccaggt gtagagtcac agctcattct tgactccaag gataattacc    4920
tggttagaat tacatggtaa actaaaagaa agacttacgt agatttgttt gctaaaacta    4980
aaacaagacc attaattttg agataattgc tttatttatc tcccatacca cccctaatca    5040 aaatttttt cccctctggc agctatgatg agcattctta tgctgttatc catgtgttat    5100
tttcaaattt gatatattgc attaaaagag atgaaatagg aatatgaact aattatccat    5160
tttaacgaat aactcaataa ttattattat gtgtatacat tctagaaatc ttaggaaaaa    5220
atgttcttta gttgataaca ggaaagtaaa ttaaatcatg taatcctgag tgaattaaat    5280
atgctcttca aaatagatga tgaacatagc atcatacttt ggaataatgt tttaactctg    5340
ggatagtaca gcctgttttg agtggtagta tttcattatc tttatatgtt tctcttcaat    5400 atctctttt tgttgactcc tatattttaa catcttttg gtatatttgt tagctgttta    5460
tagggaataa tttttcttaa tagaatagca gctggtgcaa ctctaagaac atgtcaaatc    5520
taggaattct tttttccttt ttcaataatg agtggtttgc tttcatagca ctgctctgaa    5580
gtgtgatgct gaaggcttat ttctgcataa atctgcagtg ttttatagc tgtagtgtac    5640 ctaagcacca atttagctta gcaaattaac ttagatgctt caaaattgaa aaccagtata    5700
ttctaatgta gtttgagttt aagtctttat tagtaaggat gcacttaaca tttgttcagg    5760
agaagagaat ataattttct cctgcagttg tcatttacgt aatccatttt tctagtcttt    5820
tctcaggcta atgatattcc ataccttgat acagcttta tttgtttatt tgccataata    5880
tggagtgata ccttcgagaa aattagatat ttgaatctaa tatcccaaaa gtattactta    5940
gttttctgtg tttccttaaa cagaatcatt tccatttcg gtgcaggtgt taagtgtgat    6000
gcttccataa tacatttgga tgctgtcagc taagttcact tctgaactaa ggggttcctc    6060
caaatgttgg ctgaaattca tcccaaggct ggtctgcaag tgagtgtctg cacacagttt    6120
gcttgtatgt ggagtcgatc caaaatagca tcaatgttgg ttttaccaaa gtatttatta    6180
ttgataatag aggctaagta caaaatgtag agaatgtcag ctacttgagg cctttgatta    6240
ttaaaaattt tattaatgca ttaaacaaga gtacagtaaa tagataaatt ttaggttcat    6300
gaaataaaac tgaataattt atttttactt actatttatc atggaattac tttgaataat    6360 ttattttaa tggtataatt ggacagtaaa atttataaac tcagtgcttt tcataaaaat    6420
caaagtgaag tttgtaatat tttatacaaa tagaattatt atttaagaga aataacctgt    6480
ttatgcctaa ttacagtttt taatcatttc agttacctat ttctttaag aataaattta    6540 gtgggaatat cagttccagt catgggtacc aaacttttt agtgacagag tacacacagg    6600
tatgtaaaac ttgtcatttc tcatcaaata gaggctgctg aatataggca ggtaagaaaa    6660
gctatgagaa agaattgttt tgcagaatat ttgtctagtt gtcagagcaa ggaactgaat    6720
ttattgacac agaacatttt attaagtaaa aaaaatggtc cttataacaa aaaaaaaagc    6780
taattttaca gaaggcagta gttaatatag ccgccaataa aataaatgtt tctctgaata    6840
```

```
ctttccgagg cattacagtg attttaact aatatgaagt gatatataat aatttaaag    6900
taacatcctt gagttttcct attattaatt gcttatggaa attgggtttc acgtatgact   6960
gagagctaaa gcattacagt gagttagaaa acacaacaca aatgtaaaga aaatgttagg   7020
tggtgagtaa tctgattcct ttttgtttgc ctttaagctt agttttttgt tttgtttac    7080
tttgttttaa accatgtata aaattgttga atttaaaaga taagaggatt aagtaatttc   7140
tttttcctc ctaaggataa atgtaggaaa atctaaaca cataggcaga ttggttgagt     7200
tttatatctg ttatcggcca catttattaa gattcatatt tcatgtatat tagaggtatt   7260
cacatgtatt aaaattctta tattccttct atataaaata gatgtagggg gttcccactc   7320
ttgaaaatat gaagaaaaga tgtcctttca gcaataatgg gttatggttg attaactgag   7380
aaggttgtat taaacgttct ctagtagaaa tggctaaaga gcatgctttt tgagaagtgt   7440
atcatctagg aagaaaatca aatggagtat tggtaattaa attgtaattc catgaaggaa   7500
ggaagtggtg caaagatga agctaactat tcctgttttt cttttaaga gtctgcaatt     7560
cataatggag ctactgtact ggctattgga aggaggagat tctgaagata aggaggtaat   7620
attatctctt ttaaaagaat actttcctct gtaatcctga atctttatta catgtaagaa   7680
ctttgtgcag tagacagcaa tttctttgaa tttggtatat ggaaacaatt ttattttcct   7740
ctgctaagtt tttgagcctg cctcttctag tgccatggac tgcattggta gagctgagaa   7800
atatcattta gccatactca gcacccttaa aatagcttct ttctgagaat tagatctgtg   7860
aaggtgtcct gcacagttct tgtagatgtc attttagttt gtggttgacg tgcatgcatt   7920
tagcatgttg cttaaccgtc ctcattcgcc tcccagttct ttgttgcctt catttggggg   7980
gatgtgtttt ctgctggatg atttactgct agacatgacc aaactctgag tataagactt   8040
ggtgtttggc agctggttcc agtgctctgc tgagaagtag ttgggcccag cctggggcat   8100
tgtagtgtcc tggaggccgg gagctcctgc acagggttc ttttcctggt tcagagcctt    8160
aggtgccttt ccacttttca cgtaatcttt tcctaggttg gcttgctgct tactttgcag   8220
ctgttgcagg gattcacatg gaatggaggg ctcccttta ttgtggatta tttctttgat    8280
aatttaccca tgtgcttttt cattttcaaa aacccagtgg tgtttaagaa tgaaagattc   8340
ttgaagaaca aaaattgggt taaatttgta tctatcagaa aagattctat cctctgatgc   8400
tatgtaggca cattgaatat gcaggctaaa ttaaaaacag agtaaaacct ttttataata   8460
tgccaattac tatatctaag aatgtttata caggctgaaa ttttgtaatg gtatttatat   8520
ctgttttcct ttttaaggaa aataatatac ttttctaggc atcaaaaata tctgcccctt   8580
tcactaatgc tgatgtacca ccttccccca acccccaacg ctaaatttga ctggcttaaa   8640
aacatctgcc ccctgaacta tatctgggga ggaatattaa taaaacaatg aaggacttca   8700
tggtgtctag ttatataatt aggaaattgg ttagaaacgt ggctaaaacc agtttctttc   8760
attaaaagaa ctagtgtaca tttaaaaaca aaaaccttca ggaaaaagac tctttgatct   8820
ttaagtcaaa tagtattttt ggttaacaca gcaggaaggg gaaatatacc aatttcagat   8880
tctttattt atgcctaagt agaggttgta agcagctaag gaagtgatta aaatgtagtc    8940
tagtaaaaaa tggtgctgat tacttggaaa gcagtttaca tttgcaaaaa aattcagtat   9000
tatgaccttc accaactttt acacatcata tacttgggtt attacttatg gtatagcttg   9060
tgtatggaat gcaagggtat tttcaaattg actaggtctt gctggtcatc ttaaaatatg   9120
ttacaatatt acaaaattga aatgtaatat tttttaatag aaggaaaata taaatttaat   9180
```

```
atctgggcaa ttgagacctt taaacttact ttaaaagtat gatcttgatg tatatgatac    9240
tgttttgtct ttgctatatt aacagaatta gagggtgtt ctgcaattca aataccttat     9300
atattccaaa ttttattctc tataatggac ttttaaaata aaaggtatat gtgcttcaag    9360
agggcaaaat ttgaatcatg agctaatttg ctaagcatca gattatagaa aagcatcctt    9420
gattaatttg gaactgtgaa agggggcggg taaaactgtt ttctgcagaa atttactagt    9480
gcagcaacca tttaaattaa atgtttgtta acataatagt gatggcattt tctcctcccc    9540
ctccttgtgg ttttgtccaa ctagatgtta cagtggcagt tgcactgact gttaagtgtt    9600
taaatgatga caccattatg tgaagtgatt ttgaaatgag agattccagc caagaattac    9660
atctgctccc atctccttca aatcatactc tctggcagta cagattatga ttgatttgtt    9720
tgtgacagat tgcaggaaac agtcattgat ttttcaatat tttaccttaa aattatttac    9780
agttgtaacc atggggaggt attttcatgg gctgtcagcc cctgaaagac taggataata    9840
ttccctgctc tctgacaaga caaattacct gtaatgagtg cagtagctga agggtatact    9900
tttattttaa aatatgtcaa taaccccagt gactaaacga atattgattt agcataatga    9960
agcctgagta acgtgaaaat gagctttttc aaggggcatg gtaaagtctt tcttttagc    10020 tggttgtaag aagcttttga ttcttttcag ccagctggta ggaatataga attttataag   10080
caaaccatca ggaatgatag tgttgtttct gataagcaac atccaaatat tttgaccctg   10140
cttttagtgg ttttttttcaa atcttatttt gagtcttact tttagtcata gaatagctac   10200
tgatttgatg cggtctttaa ctgacttaat attttacaa tttcaatata ttttgcattg    10260
gaatctccag taatgaatat taaaatatat gtacaatcat ttgtagatga tatcaattat   10320
attaagacat ttcagatggg ctattgtagt atttaatgtg ccgtatttta tggtagaata   10380
attctcagtc tctggacatc aagattgctt tcagtgggaa tgaagattaa tttacttcag   10440
tcctgatttt ttaggcatca atgcatgttt tcattttgt cagacttta ccctctttta     10500 atgtaattct caacttctta tggatttact tcccaataca taaaatcctt caaaacaaga   10560
atgataataa ttttttatact ttttataaaa ataaatttat ttttagtcca tcaaggtgtc   10620
tgaagatttt atgcctaggt atctccatat ctaacttgat aaggaaaata ggataaacaa   10680
tgctggtaat agcaggaaag taagtatttg aataagatgt caaactgata tttcatgtga   10740
acctaactca ttttatggta actaataatt atcttattta aatcaatagg taaaacctgt   10800
ttagaaatta aaaatgagtt acgatttaaa gaaaattcag atgactcatt gtgagtgcta   10860
gttctcttgt aggatgccac tggaaatgtt gaaatgaaaa atgtaagtat atcttttggt   10920
ggaaaaaagg atagtctcta ggacacaaaa ttactgtttt atttttttct caggagtttg   10980
cctaagggtg tgacagatga tctctgtcac ttgtcttagt tgtgtcctgc aataaactgg   11040
atgctttata aaatactaga cctgtgattt cgtatgctgt aatatttcat ttctccatca   11100
cccctccaaa ttatttctta gtttggagta aaataataaa tgtattatag tcaacatctc   11160 ttgaccccte tttagtttca gctaaactaa gcatgtgtgt ttgtgtgttc attttatagt   11220
tcatgtgtag aactatgtga attaaattta agaaacatgt aaagtagagg aaatagtttt   11280
ctggagaaat ttttccttttt tggatattat gcccttttcc attgctttc tctgcttgaa    11340 agcaaaaaaa agtaccctac ccctgttctc ctttagggaa aaactattcc tataaagtat   11400
ttttaaatcg tgcaagtcat tgcctagggt tagctaaaac atttcttttt aaaaaggaga   11460
aaatgccctg gctttaacat tttcttgtat ttgtatctat taagataaac agtttacttt   11520
gatacagtac ataccaatct acttaattttt ttttccagga ttccttttac tatgtttggt   11580
```

```
ctgaccttttt atgataactt aatatgggaa caaattagca tataattcta ttttccatgt   11640
gacctcaacc agttgcagaa ttgtaccact actttagggg gggcaatttg acagtttatg   11700
tagactatag cattaattgt tcccaaatgt tcagtgcatc ctggctaatg tgttattgaa   11760
ggtgttttca cgtaagcagt tagaggaagc acttcacccc tattactaag ttattaaaat   11820
gcctcctaaa ggtagcattt taaattagta tacataattg attagtaatt tgtcttctcc   11880
caagcataaa acagcatagc agagttaagt gtgaccagtg aagtataaga tattagggat   11940
tgatggtgac aatgatcata gcaactaaat ggatttttt tttcttttag attcagccgt    12000
tggtctttga aatttcctgt gatgtgtttc aatctagatg caaagaacat ggaaaaatca   12060
aagtgctcga gtggtttaaa tatgttttgg gtattcctgt ttatagacta taatactttt   12120
ccaattaaaa tcctcagttg tcacgcagaa gaaggttaag ctgtatttga ttgccagttt   12180
tactgaaaat gcttagtatt ttacagtatc accaaatata ttttgtttag ccaaggtata   12240
ggaaaaataa aataaattgt ataggttgac tttttctaa aatgtcttta ttggattgaa    12300
tgaatgttta tacctgaaaa aaaaaggttc aaaaaaattc cttttctat cagagtcatt    12360 cttttgacaa tcagatatta gactaggttt aaaataactt tctaatatga ctcatattta   12420
tgggaggaaa aagacttgaa agatattcct atgtgtactt taattttctg taatagtccc   12480
tctggaatag aatatctctt cctcaaacaa atcattggc tcatttcata tacaagaaaa    12540
agttgcccta aatggcagag tttcatctct gtaaagaagg ctgacatcca cttccttcac   12600
agaatccctg catttgggta attgagtaat gatagattac cttgccattg ggaaatacct   12660
tgttgtggcc tttgtagcag ctataggaag atggaagaat tcttttgtat agacaggtct   12720
ctagcctctt tggtgtggac actgtgaagg ggtacatctg gtgagaagga gtgcttaggg   12780
aaggaactgg gaaggtccac aaaggctgat gatgacaaag aatccaaggg ctatgatgaa   12840
ttcttaagct tagatctcag agtcataaag taaatttatt aggctagaga gatttccttt   12900 tttattttg atcaaacttt attttttcag attgttaagt tcacatgcag ttgtacaaaa    12960
taatacagag atctttgaac actacccagt ttctcctaat agtaacttct tgcaatatac   13020
tgtatagcac agcatcacaa cctggatact gacattgatg cagtcaagac agagaacatt   13080
tatatcatga ggaggatccc tcattaccgc cctttgatat ccaccccta ttccagacca    13140 tctcactcct cccttaaccc tggcaaccac tagcatgttc tccatttcta taaatttgcc   13200
tttataggaa tgttatataa ttgcaattaa agtgtgtaac cttttggggt ttgactcacc   13260
cggcatcatt ttctggagat tcagcttata tgtgtcaata gtttgttccc ttttttttag   13320
ttcagtagta ttctgtggta cgtgtgtacc acatcactca tcaattcgga cttctgggtt   13380
gtatctggta tttgattatt acaaatagaa gtactatata tatattcgtg tagaggtttc   13440
tgtgtgaaca taaactttca ttttcctggg acagatgccc acgagtgaaa attgtgagtc   13500
atatggtaat tatgtagagt atttttttt tgagacgatt tgtttatgat tttaaaacat    13560
aaaaatataa gttgtagcca aatataagga aggattttc cacaatctag actttattct    13620
tattttagag aaatactttt gaaaaaattg ctttattggc aaacaattcc tatgtaaagg   13680
aataaaagac gcatatactc taggaaagat gttgcaaagc tgacaggcaa ctttgagaaa   13740
gatgagggca gttttccagt gttactggag acttgacatt caaggatgta ttatgatagt   13800
ttctgaattg atagattctt tagcgttgt cactaccctc aggcctgcag tttttatttg    13860
tagaattaac tcatctttac aatgctttgt tgagtgctgt tgcagaaaat gctcatgtaa   13920
```

```
ttcaattata tgcagttagg aaaaagaagt atcttttttct agtacatggc ccctaaaatg   13980
atgactttcc acaatgctga atggaggaaa cagctctgtt tccatcaaac tctggtggaa   14040
attatacaaa gttatattat gctttatgag acatagtgag gtagtacaca accatatatg   14100
ctatattatt ggggagaccc actgaaagaa ttttcaagga taattttgc tctgattttc    14160 tatcatgtat attgacttta ttgattgatt gattgagatg gagtctcacc ccgtcaccca   14220
ggctgaagtg cagtggtgca atctctgctc actgcaacct ccgcctctca ggttcaagtg   14280
atcctcgtgc ctcagcctcc cgagtagctg agactatagg tgtgtgctac gatgcccagc   14340
taatttttgt attttttagta gagacaggat ttggtagcct ggtctcgaac tcctgacctc   14400
aggtgatcta cccaccttgg cctcccaaaa tactgggatt acaggtgtga gccaccgtgc   14460
tggccaagta tattgacttt aaaacgttac cggctgggcg tggtggttca cgcctgttat   14520
cccagcactt tgggagcccg aggcggatgg attacctgaa gtcaggagtt cgagaccagc   14580
ccaacctggt gaaaccccgt ctctactaaa aatacacaaa ttagccgggc gtggtggcag   14640
gcgcctataa tcccaactac tgggaaggct gaggcaggag aattgcttga acctggcagg   14700
cggaggctgc agtgagccaa gactgcgcca ctgcactcca gcctgggcaa caagagcaaa   14760
actcagtctc aaaaaaaaca gaaaaaaaaa gttaccacgg gtgaaacatt gggctggtca   14820
cagtgatcct tctaacagca gtcaatatta taaatctagc ttttttttt gagtgagata    14880 ctaggcccag ggaacccgag tcttcaatc ctcatgaata tagtttaatc tttagctcat    14940
tatggtcatg accatagtta aataaatgac acgagataat aaaatagtct ttgcccttaa   15000
aactgacctg ggtaaaagga tgtacacttg aatctttgaa taccagaata gtcattcatt   15060
cattgagccg tgttgtagca tcccatcttc tggcacttcc agcactggga acccatcata   15120
aagaaggcac tacaggccag gcgctgtggc tcacgcctgt aatcccagca ctttgggagg   15180
ccaaggcagg cggatcacct gaggtcagga gttcgagacc agcctggcca acatggtgaa   15240
accccatctc tactaaaaat acaaaaagta actgggcatg gtggcaggcg cctgtaatcc   15300
cagctacttg ggagggtaag gccagagcat cgcttgaacc cggaaggcag aggttgcagt   15360
gagccaagat cctgccattg cactccagcc tggggataa gagcgagact tcgtctaaaa    15420
aaaataaaaa taaaaaggca ctacagcacc tgttctctta gtgtagctct attagctctt   15480
agactagggg gtagggatgg gaaaaagtaa aagaaactg agaaaccaat ctaattacgc    15540
ataatcagaa atccaaagct tccagaattc atgaggaaaa agaactgcag ctgatggagt   15600
aggcattaca gagaatgaga ggcttgcttt ttttttaagt ttcattttat ttgtaattga   15660
cacaatagca catatttacg ggatacagtg tgacatttta atacatttac atattgtgta   15720
atgatcaaat taggataatt agcttatgta tcacttcaaa aacataattt ctttgtgatg   15780
agaacattca aaatcttcta gtattttgaa atacataatg caatattgtt aaccacaatc   15840 acctactgt gcaatagaac accagagttt actcctcttt tccatctgta gcttcagacc    15900
cattgaccaa tctctcccct tcgcccccca ccacccccc cccgccgtc accactctcc      15960 tccctccc agcaagaggc ttgaatcttg aaggagcaca tcagatagaa agagggaaat     16020
caactgggac atggtttgtt ggaagtgggg tggaatctgg tttgtttaca gtttcagagt   16080
ttgaggcatc aaaagtgtat gtcattgccc aaaagtattt aacagctttc tatgtttttag   16140 gaattcacta gaaataaggc atgctttta aaaagaaaa aaaatagtaa tctttgaatt      16200
taaatatgtg ggtttccatg aaaaacaaat gagtacccctt ccttgaaaaa ctactacttt   16260
gaagagtctc gtaggttctg aggctcgtgt gtgtgtgtgg gtgtgtgtgt ataaaacatt    16320
```

```
ttcttttata tttggtaaga aggaataagg tattttatac ttttctggtc tgttaaatgc   16380
ataatctata agactataat actttaaaaa attttagttt atctgaggct taaaataaca   16440
aaagaactta aagctcctgt ggaagagctc caaaattaaa actgtaagat cacatataga   16500
taaaacgtta tataaagcag ctttgggac cccaggcatg atggctcatt cctgtaatcc    16560
cagcactttg ggaggccaag gtgggtggat cacctgaacc caaaagttcg agaccagcct   16620
gagcaacatg gtgaaaccct gtctctacaa aatacagaaa aaaaaaatat taaccaattt   16680
ttttaacctc ccagctactt gggaggctga gatgggagga tggcttgagc ctggggaggt   16740
cgcggctgca atgagtcatg atcgcgccac tgcactccag cctgggtaat agattgaaac   16800
tctgtctcca cacacacaca cacaaatgac ttttggtaag actgtacata gagtttatgg   16860
ccttattaag aaactctttt gagcaaccta agaaaacaca agtatttctg tacattactt   16920
tgttaaagtg tacaggataa taagagagag ctaagagcct tttctaaatg tgcatccaat   16980
tttaagaggc taaaatagga agctttcaa                                    17009

<210> SEQ ID NO 2
<211> LENGTH: 184
<212> TYPE: DNA
<213> ORGANISM: Homo Sapiens

<400> SEQUENCE: 2
atgtacttta tttcgcgatc tcacactaac ccagcgccgc accggcaccc gctcggtgct     60
gcgctctcgt gcacgcgcgt tggctcctcc cctccgtctg ctcccctccc ccagacaccg    120
cccaccaaga ggcctgagcg gttcagacta cattctccga gagcccctgg gtccgcccag    180
ccca                                                                184

<210> SEQ ID NO 3
<211> LENGTH: 724
<212> TYPE: DNA
<213> ORGANISM: Homo Sapiens

<400> SEQUENCE: 3
tctcggcgcc agaggggcgg ggaggggcgg ggtctcgatc gcgctattgt catggagacg     60
ggaagctggc tgcagcggcg gcggggaccg tggggccgag gtggctgcca gccggccaat    120
gtctaagcga ggcggagcgg cccaggcggc ccgagcctgg gggagcgcgc agccggccag    180
tggcggcctc gccggcggcc tcttcccggg ctcgcagtag gcccgagtcg tcgccgggag    240
ctcctgggag cagcgtcccc gccctgctcc cctcgctccc gctcttgcg gccccacggc     300 ccctcagcgc ccgcccccgg ctccgcccgc cgcagccgca gccctggcg ctaacggtcg     360 gtaacggccc gcgcgcgccg cccgccgggg gctcgcgcca gccacgaggg agcgtccgcg    420
gcccgcgcgc ccgcgcggcg gaggagaggt gagcccccgc ccgggccagg ccctctggcc    480
gcgccgtccg cccctctagt cgtgtcccct cgtgggccga acggacgcgg cggtgccccg    540
cgcccgacca gacgtcccgt gggctagggc ctgggcctcg ggccgcgtcg gcgccggtcg    600
agcctctccg ggtgtcgggg ttcggggcgg gcgcgcgtgg gcgtggctcc tctgtccacg    660
cctgttccct tcgtcgccgc ggctctcgtc cgggacacgg ctttccggag tagagccctt    720
ggag                                                                724

<210> SEQ ID NO 4
<211> LENGTH: 448
<212> TYPE: DNA
```

<213> ORGANISM: Homo Sapiens

<400> SEQUENCE: 4

| | | | | | | |
|---|---|---|---|---|---|---|
| tctcggcgcc | agaggggcgg | ggaggggcgg | ggtctcgatc | gcgctattgt | catggagacg | 60 |
| ggaagctggc | tgcagcggcg | gcggggaccg | tggggccgag | gtggctgcca | gccggccaat | 120 |
| gtctaagcga | ggcggagcgg | cccaggcggc | ccgagcctgg | gggagcgcgc | agccggccag | 180 |
| tggcggcctc | gccggcggcc | tcttcccggg | ctcgcagtag | gcccgagtcg | tcgccgggag | 240 |
| ctcctgggag | cagcgtcccc | gccctgctcc | cctcgctccc | gcctcttgcg | gccccacggc | 300 |
| ccctcagcgc | ccgcccccgg | ctccgcccgc | cgcagccgca | gccctggcg | ctaacggtcg | 360 |
| gtaacggccc | gcgcgcgccg | cccgccgggg | gctcgcgcca | gccacgaggg | agcgtccgcg | 420 |
| gcccgcgcgc | ccgcgcggcg | gaggagag | | | | 448 |

<210> SEQ ID NO 5
<211> LENGTH: 274
<212> TYPE: DNA
<213> ORGANISM: Homo Sapiens

<400> SEQUENCE: 5

| | | | | | | |
|---|---|---|---|---|---|---|
| gagcccccgc | ccgggccagg | ccctctggcc | gcgccgtccg | cccctctagt | cgtgtcccct | 60 |
| cgtgggccga | acggacgcgg | cggtgccccg | cgcccgacca | gacgtcccgt | gggctagggc | 120 |
| ctgggcctcg | ggccgcgtcg | gcgccggtcg | agcctctccg | ggtgtcgggg | ttcggggcgg | 180 |
| gcgcgcgtgg | gcgtggctcc | tctgtccacg | cctgttccct | tcgtcgccgc | ggctctcgtc | 240 |
| cgggacacgg | ctttccggag | tagagcccctt | ggag | | | 274 |

<210> SEQ ID NO 6
<211> LENGTH: 113
<212> TYPE: DNA
<213> ORGANISM: Homo Sapiens

<400> SEQUENCE: 6

| | | | | | | |
|---|---|---|---|---|---|---|
| gtgttaagtg | tgatgcttcc | ataatacatt | tggatgctgt | cagctaagtt | cacttctgaa | 60 |
| ctaaggggtt | cctccaaatg | ttggctgaaa | ttcatcccaa | ggctggtctg | caa | 113 |

<210> SEQ ID NO 7
<211> LENGTH: 284
<212> TYPE: DNA
<213> ORGANISM: Homo Sapiens

<400> SEQUENCE: 7

| | | | | | | |
|---|---|---|---|---|---|---|
| gtgttaagtg | tgatgcttcc | ataatacatt | tggatgctgt | cagctaagtt | cacttctgaa | 60 |
| ctaaggggtt | cctccaaatg | ttggctgaaa | ttcatcccaa | ggctggtctg | caagtgagtg | 120 |
| tctgcacaca | gtttgcttgt | atgtggagtc | gatccaaaat | agcatcaatg | ttggttttac | 180 |
| caaagtattt | attattgata | atagaggcta | agtacaaaat | gtagagaatg | tcagctactt | 240 |
| gaggcctttg | attattaaaa | attttattaa | tgcattaaac | aaga | | 284 |

<210> SEQ ID NO 8
<211> LENGTH: 87
<212> TYPE: DNA
<213> ORGANISM: Homo Sapiens

<400> SEQUENCE: 8

| | | | | | | |
|---|---|---|---|---|---|---|
| ttacctattt | cttttaagaa | taaatttagt | gggaatatca | gttccagtca | tgggtaccaa | 60 |
| acttttttag | tgacagagta | cacacag | | | | 87 |

<210> SEQ ID NO 9
<211> LENGTH: 370
<212> TYPE: DNA
<213> ORGANISM: Homo Sapiens

<400> SEQUENCE: 9

```
agtctgcaat tcataatgga gctactgtac tggctattgg aaggaggaga ttctgaagat      60
aaggaggtaa tattatctct tttaaaagaa tactttcctc tgtaatcctg aatctttatt     120
acatgtaaga actttgtgca gtagacagca atttctttga atttggtata tggaaacaat     180
tttattttcc tctgctaagt ttttgagcct gcctcttcta gtgccatgga ctgcattggt     240
agagctgaga aatatcattt agccatactc agcaccctta aaatagcttc tttctgagaa     300
ttagatctgt gaaggtgtcc tgcacagttc ttgtagatgt catttttagtt tgtggttgac    360
gtgcatgcat                                                           370
```

<210> SEQ ID NO 10
<211> LENGTH: 66
<212> TYPE: DNA
<213> ORGANISM: Homo Sapiens

<400> SEQUENCE: 10

```
agtctgcaat tcataatgga gctactgtac tggctattgg aaggaggaga ttctgaagat      60
aaggag                                                                66
```

<210> SEQ ID NO 11
<211> LENGTH: 194
<212> TYPE: DNA
<213> ORGANISM: Homo Sapiens

<400> SEQUENCE: 11

```
catgcttttt gagaagtgta tcatctagga agaaaatcaa atggagtatt ggtaattaaa      60
ttgtaattcc atgaaggaag gaagtggtgc aaaagatgaa gctaactatt cctgttttc     120
tttttaagag tctgcaattc ataatggagc tactgtactg gctattggaa ggaggagatt     180
ctgaagataa ggag                                                      194
```

<210> SEQ ID NO 12
<211> LENGTH: 113
<212> TYPE: DNA
<213> ORGANISM: Homo Sapiens

<400> SEQUENCE: 12

```
gtaaaacctg tttagaaatt aaaaatgagt tacgatttaa agaaaattca gatgactcat      60
tgtgagtgct agttctcttg taggatgcca ctggaaatgt tgaaatgaaa aat           113
```

<210> SEQ ID NO 13
<211> LENGTH: 30
<212> TYPE: DNA
<213> ORGANISM: Homo Sapiens

<400> SEQUENCE: 13

```
gatgccactg gaaatgttga aatgaaaaat                                      30
```

<210> SEQ ID NO 14
<211> LENGTH: 41
<212> TYPE: DNA
<213> ORGANISM: Homo Sapiens

<400> SEQUENCE: 14
ttctcttgta ggatgccact ggaaatgttg aaatgaaaaa t                 41

<210> SEQ ID NO 15
<211> LENGTH: 1750
<212> TYPE: DNA
<213> ORGANISM: Homo Sapiens

<400> SEQUENCE: 15
tttaatagaa ggaaaatata aatttaatat ctgggcaatt gagacccttta aacttacttt    60
aaaagtatga tcttgatgta tatgatactg ttttgtcttt gctatattaa cagaattaga   120
ggggtgttct gcaattcaaa taccttatat attccaaatt ttattctcta aatggactt    180
ttaaaataaa aggtatatgt gcttcaagag ggcaaaattt gaatcatgag ctaatttgct   240
aagcatcaga ttatagaaaa gcatccttga ttaatttgga actgtgaaag ggggcgggta   300
aaactgtttt ctgcagaaat ttactagtgc agcaaccatt taaattaaat gtttgttaac   360
ataatagtga tggcattttc tcctccccct ccttgtggtt ttgtccaact agatgttaca   420
gtggcagttg cactgactgt taagtgttta aatgatgaca ccattatgtg aagtgatttt   480
gaaatgagag attccagcca agaattacat ctgctcccat ctccttcaaa tcatactctc   540
tggcagtaca gattatgatt gatttgtttg tgacagattg caggaaacag tcattgattt   600
ttcaatattt taccttaaaa ttatttacag ttgtaaccat ggggaggtat tttcatgggc   660
tgtcagcccc tgaaagacta ggataatatt ccctgctctc tgacaagaca aattacctgt   720
aatgagtgca gtagctgaag ggtatacttt tatttttaaaa tatgtcaata accccagtga   780
ctaaacgaat attgatttag cataatgaag cctgagtaac gtgaaaatga gcttttttcaa   840
ggggcatggt aaagtctttc ttttttagctg gttgtaagaa gcttttgatt cttttcagcc   900
agctggtagg aatatagaat tttataagca aaccatcagg aatgatagtg ttgtttctga   960
taagcaacat ccaaatattt tgaccctgct tttagtggtt ttttttcaaat cttattttga  1020
gtcttacttt tagtcataga atagctactg atttgatgcg gtctttaact gacttaatat  1080
ttttacaatt tcaatatatt ttgcattgga atctccagta atgaatatta aaatatatgt  1140
acaatcattt gtagatgata tcaattatat taagacattt cagatgggct attgtagtat  1200
ttaatgtgcc gtattttatg gtagaataat tctcagtctc tggacatcaa gattgctttc  1260
agtgggaatg aagattaatt tacttcagtc ctgatttttt aggcatcaat gcatgttttc  1320
attttttgtca gactttttacc ctcttttaat gtaattctca acttcttatg gatttacttc  1380
ccaatacata aaatccttca aaacaagaat gataataatt tttatacttt ttataaaaat  1440
aaatttattt ttagtccatc aaggtgtctg aagattttat gcctaggtat ctccatatct  1500
aacttgataa ggaaaatagg ataaacaatg ctggtaatag caggaaagta agtatttgaa  1560
taagatgtca aactgatatt tcatgtgaac ctaactcatt ttatggtaac taataattat  1620
cttatttaaa tcaataggta aaacctgttt agaaattaaa aatgagttac gatttaaaga  1680
aaattcagat gactcattgt gagtgctagt tctcttgtag gatgccactg gaaatgttga  1740
aatgaaaaat                                                          1750

<210> SEQ ID NO 16
<211> LENGTH: 2228
<212> TYPE: DNA
<213> ORGANISM: Homo Sapiens

<400> SEQUENCE: 16

```
tgataagcaa catccaaata ttttgaccct gcttttagtg gttttttttca aatcttattt      60
tgagtcttac ttttagtcat agaatagcta ctgatttgat gcggtcttta actgacttaa     120
tatttttaca atttcaatat attttgcatt ggaatctcca gtaatgaata ttaaaatata     180
tgtacaatca tttgtagatg atatcaatta tattaagaca tttcagatgg gctattgtag     240
tatttaatgt gccgtatttt atggtagaat aattctcagt ctctggacat caagattgct     300
ttcagtggga atgaagatta atttacttca gtcctgattt tttaggcatc aatgcatgtt     360
ttcattttg tcagactttt accctctttt aatgtaattc tcaacttctt atggatttac      420
ttcccaatac ataaaatcct tcaaaacaag aatgataata atttttatac tttttataaa     480
aataaattta ttttagtcc atcaaggtgt ctgaagattt tatgcctagg tatctccata      540
tctaacttga taaggaaat aggataaaca atgctggtaa tagcaggaaa gtaagtattt      600
gaataagatg tcaaactgat atttcatgtg aacctaactc attttatggt aactaataat     660
tatcttattt aaatcaatag gtaaaacctg tttagaaatt aaaaatgagt tacgatttaa     720
agaaaattca gatgactcat tgtgagtgct agttctcttg taggatgcca ctggaaatgt     780
tgaaatgaaa aatgtaagta tatcttttgg tggaaaaaag gatagtctct aggacacaaa     840
attactgttt tattttttc tcaggagttt gcctaagggt gtgacagatg atctctgtca      900
cttgtcttag ttgtgtcctg caataaactg gatgctttat aaaatactag acctgtgatt     960
tcgtatgctg taatatttca tttctccatc accctccaa attatttctt agtttggagt     1020
aaaataataa atgtattata gtcaacatct cttgacccct ctttagtttc agctaaacta    1080
agcatgtgtg tttgtgtgtt cattttatag ttcatgtgta gaactatgtg aattaaattt    1140
aagaaacatg taaagtagag gaaatagttt tctggagaaa tttttccttt ttggatatta    1200
tgccctttc cattgctttt ctctgcttga aagcaaaaaa aagtacccta cccctgttct     1260
cctttaggga aaactattc ctataaagta ttttttaaatc gtgcaagtca ttgcctaggg    1320
ttagctaaaa catttctttt taaaaggag aaaatgccct ggctttaaca ttttcttgta     1380
tttgtatcta ttaagataaa cagtttactt tgatacagta cataccaatc tacttaattt    1440
ttttccagg attccttta ctatgtttgg tctgaccttt tatgataact taatatggga      1500
acaaattagc atataattct attttccatg tgacctcaac cagttgcaga attgtaccac    1560
tactttaggg ggggcaattt gacagtttat gtagactata gcattaattg ttcccaaatg    1620
ttcagtgcat cctggctaat gtgttattga aggtgttttc acgtaagcag ttagaggaag    1680
cacttcaccc ctattactaa gttattaaaa tgcctcctaa aggtagcatt ttaaattagt    1740
atacataatt gattagtaat ttgtcttctc ccaagcataa aacagcatag cagagttaag    1800
tgtgaccagt gaagtataag atattaggga ttgatggtga caatgatcat agcaactaaa    1860
tggattttt ttttcttta gattcagccg ttggtctttg aaatttcctg tgatgtgttt      1920
caatctagat gcaaagaaca tggaaaaatc aaagtgctcg agtggtttaa atatgttttg    1980
ggtattcctg tttatagact ataatacttt tccaattaaa atcctcagtt gtcacgcaga    2040
agaaggttaa gctgtatttg attgccagtt ttactgaaaa tgcttagtat tttacagtat    2100
caccaaatat attttgttta gccaaggtat aggaaaaata aaataaattg tataggttga    2160
ctttttcta aaatgtcttt attggattga atgaatgttt atacctgaaa aaaaaaggtt    2220
caaaaaaa                                                             2228
```

<210> SEQ ID NO 17

<211> LENGTH: 603
<212> TYPE: DNA
<213> ORGANISM: Homo Sapiens

<400> SEQUENCE: 17

```
tgcatcctgg ctaatgtgtt attgaaggtg ttttcacgta agcagttaga ggaagcactt      60
caccccatt actaagttat taaaatgcct cctaaaggta gcattttaaa ttagtataca     120
taattgatta gtaatttgtc ttctcccaag cataaaacag catagcagag ttaagtgtga     180
ccagtgaagt ataagatatt agggattgat ggtgacaatg atcatagcaa ctaaatggat     240
tttttttttc ttttagattc agccgttggt ctttgaaatt tcctgtgatg tgtttcaatc     300
tagatgcaaa gaacatggaa aaatcaaagt gctcgagtgg tttaaatatg ttttgggtat     360
tcctgtttat agactataat acttttccaa ttaaaatcct cagttgtcac gcagaagaag     420
gttaagctgt atttgattgc cagttttact gaaaatgctt agtattttac agtatcacca     480
aatatatttt gtttagccaa ggtataggaa aaataaaata aattgtatag gttgactttt     540
ttctaaaatg tctttattgg attgaatgaa tgtttatacc tgaaaaaaaa aggttcaaaa     600
aaa                                                                  603
```

<210> SEQ ID NO 18
<211> LENGTH: 347
<212> TYPE: DNA
<213> ORGANISM: Homo Sapiens

<400> SEQUENCE: 18

```
attcagccgt tggtctttga aatttcctgt gatgtgtttc aatctagatg caaagaacat      60
ggaaaaatca aagtgctcga gtggtttaaa tatgttttgg gtattcctgt ttatagacta     120
taatactttt ccaattaaaa tcctcagttg tcacgcagaa gaaggttaag ctgtatttga     180
ttgccagttt tactgaaaat gcttagtatt ttacagtatc accaaatata ttttgtttag     240
ccaaggtata ggaaaaataa aataaattgt ataggttgac ttttttctaa aatgtcttta     300
ttggattgaa tgaatgttta tacctgaaaa aaaaggttc aaaaaaa                   347
```

<210> SEQ ID NO 19
<211> LENGTH: 832
<212> TYPE: DNA
<213> ORGANISM: Homo Sapiens

<400> SEQUENCE: 19

```
gtaagtatat cttttggtgg aaaaaaggat agtctctagg acacaaaatt actgttttat      60
tttttttctca ggagtttgcc taagggtgtg acagatgatc tctgtcactt gtcttagttg    120
tgtcctgcaa taaactggat gctttataaa atactagacc tgtgatttcg tatgctgtaa    180
tatttcattt ctccatcacc cctccaaatt atttcttagt ttggagtaaa ataataaatg    240
tattatagtc aacatctctt gaccctctct tagtttcagc taaactaagc atgtgtgttt    300
gtgtgttcat tttatagttc atgtgtagaa ctatgtgaat taaatttaag aaacatgtaa    360
agtagaggaa atagttttct ggagaaattt ttccttttg gatattatgc cttttccat     420
tgcttttctc tgcttgaaag caaaaaaaag taccctaccc ctgttctcct ttagggaaaa    480
actattccta taaagtatt ttaaatcgtg caagtcattg cctagggtta gctaaaacat      540
ttctttttaa aaaggagaaa atgccctggc tttaacattt tcttgtattt gtatctatta    600
agataaacag tttactttga tacagtacat accaatctac ttaattttt ttccaggatt    660
ccttttacta tgtttggtct gacctttat gataacttaa tatgggaaca aattagcata    720
```

| | | |
|---|---|---|
| taattctatt ttccatgtga cctcaaccag ttgcagaatt gtaccactac tttagggggg | 780 |
| gcaatttgac agtttatgta gactatagca ttaattgttc ccaaatgttc ag | 832 |

<210> SEQ ID NO 20
<211> LENGTH: 276
<212> TYPE: DNA
<213> ORGANISM: Homo Sapiens

<400> SEQUENCE: 20

| | |
|---|---|
| gtatagcaca gcatcacaac ctggatactg acattgatgc agtcaagaca gagaacattt | 60 |
| atatcatgag gaggatccct cattaccgcc ctttgatatc cacccctact tccagaccat | 120 |
| ctcactcctc ccttaaccct ggcaaccact agcatgttct ccatttctat aaatttgcct | 180 |
| ttataggaat gttatataat tgcaattaaa gtgtgtaacc ttttgggggtt tgactcaccc | 240 |
| ggcatcattt tctggagatt cagcttatat gtgtca | 276 |

<210> SEQ ID NO 21
<211> LENGTH: 913
<212> TYPE: DNA
<213> ORGANISM: Homo Sapiens

<400> SEQUENCE: 21

| | |
|---|---|
| gagcccccgc ccgggccagg ccctctggcc gcgccgtccg ccctctagt cgtgtccct | 60 |
| cgtgggccga acggacgcgg cggtgccccg cgcccgacca gacgtcccgt gggctagggc | 120 |
| ctgggcctcg ggccgcgtcg gcgccggtcg agcctctccg ggtgtcgggg ttcggggcgg | 180 |
| gcgcgcgtgg gcgtggctcc tctgtccacg cctgttccct tcgtcgccgc ggctctcgtc | 240 |
| cgggacacgg ctttccggag tagagcccctt ggaggtgtta agtgtgatgc ttccataata | 300 |
| catttggatg ctgtcagcta agttcacttc tgaactaagg ggttcctcca aatgttggct | 360 |
| gaaattcatc ccaaggctgg tctgcaaagt ctgcaattca taatggagct actgtactgg | 420 |
| ctattggaag gaggagattc tgaagataag gaggtaaaac ctgtttagaa attaaaaatg | 480 |
| agttacgatt taaagaaaat tcagatgact cattgtgagt gctagttctc ttgtaggatg | 540 |
| ccactggaaa tgttgaaatg aaaaatattc agccgttggt ctttgaaatt tcctgtgatg | 600 |
| tgtttcaatc tagatgcaaa gaacatggaa aaatcaaagt gctcgagtgg tttaaatatg | 660 |
| ttttgggtat tcctgtttat agactataat acttttccaa ttaaaatcct cagttgtcac | 720 |
| gcagaagaag gttaagctgt atttgattgc cagttttact gaaaatgctt agtattttac | 780 |
| agtatcacca aatatatttt gtttagccaa ggtataggaa aaataaaata aattgtatag | 840 |
| gttgactttt ttctaaaatg tctttattgg attgaatgaa tgtttatacc tgaaaaaaaa | 900 |
| aggttcaaaa aaa | 913 |

<210> SEQ ID NO 22
<211> LENGTH: 841
<212> TYPE: DNA
<213> ORGANISM: Homo Sapiens

<400> SEQUENCE: 22

| | |
|---|---|
| gagcccccgc ccgggccagg ccctctggcc gcgccgtccg ccctctagt cgtgtccct | 60 |
| cgtgggccga acggacgcgg cggtgccccg cgcccgacca gacgtcccgt gggctagggc | 120 |
| ctgggcctcg ggccgcgtcg gcgccggtcg agcctctccg ggtgtcgggg ttcggggcgg | 180 |
| gcgcgcgtgg gcgtggctcc tctgtccacg cctgttccct tcgtcgccgc ggctctcgtc | 240 |

| | |
|---|---|
| cgggacacgg ctttccggag tagagcccett ggaggtgtta agtgtgatgc ttccataata | 300 |
| catttggatg ctgtcagcta agttcacttc tgaactaagg ggttcctcca aatgttggct | 360 |
| gaaattcatc ccaaggctgg tctgcaaagt ctgcaattca taatggagct actgtactgg | 420 |
| ctattggaag gaggagattc tgaagataag gagttctctt gtaggatgcc actggaaatg | 480 |
| ttgaaatgaa aaatattcag ccgttggtct ttgaaatttc ctgtgatgtg tttcaatcta | 540 |
| gatgcaaaga acatggaaaa atcaaagtgc tcgagtggtt taaatatgtt ttgggtattc | 600 |
| ctgtttatag actataatac ttttccaatt aaaatcctca gttgtcacgc agaagaaggt | 660 |
| taagctgtat ttgattgcca gttttactga aaatgcttag tattttacag tatcaccaaa | 720 |
| tatattttgt ttagccaagg tataggaaaa ataaaataaa ttgtataggt tgactttttt | 780 |
| ctaaaatgtc tttattggat tgaatgaatg tttatacctg aaaaaaaaag gttcaaaaaa | 840 |
| a | 841 |

<210> SEQ ID NO 23
<211> LENGTH: 837
<212> TYPE: DNA
<213> ORGANISM: Homo Sapiens

<400> SEQUENCE: 23

| | |
|---|---|
| tctcggcgcc agaggggcgg ggaggggcgg ggtctcgatc gcgctattgt catggagacg | 60 |
| ggaagctggc tgcagcggcg gcggggaccg tggggccgag gtggctgcca gccgccaat | 120 |
| gtctaagcga ggcggagcgg cccaggcggc ccgagcctgg gggagcgcgc agccggccag | 180 |
| tggcggcctc gccggcggcc tcttcccggg ctcgcagtag gcccgagtcg tcgccgggag | 240 |
| ctcctgggag cagcgtcccc gccctgctcc cctcgctccc gcctcttgcg gccccacggc | 300 |
| ccctcagcgc ccgcccccgg ctccgcccgc cgcagccgca gcccctggcg ctaacggtcg | 360 |
| gtaacggccc gcgcgcgccg cccgccgggg gctcgcgcca gccacgaggg agcgtccgcg | 420 |
| gcccgcgcgc ccgcgcggcg gaggagaggt gagccccgc ccgggccagg ccctctggcc | 480 |
| gcgccgtccg cccctctagt cgtgtcccct cgtgggccga acggacgcgg cggtgccccg | 540 |
| cgcccgacca gacgtcccgt gggctagggc ctgggcctcg ggccgcgtcg gcgccggtcg | 600 |
| agcctctccg ggtgtcgggg ttcggggcgg gcgcgcgtgg gcgtggctcc tctgtccacg | 660 |
| cctgttccct tcgtcgccgc ggctctcgtc cgggacacgg ctttccggag tagagcccett | 720 |
| ggaggtgtta agtgtgatgc ttccataata catttggatg ctgtcagcta agttcacttc | 780 |
| tgaactaagg ggttcctcca aatgttggct gaaattcatc ccaaggctgg tctgcaa | 837 |

<210> SEQ ID NO 24
<211> LENGTH: 654
<212> TYPE: DNA
<213> ORGANISM: Homo Sapiens

<400> SEQUENCE: 24

| | |
|---|---|
| catgcttttt gagaagtgta tcatctagga agaaaatcaa atggagtatt ggtaattaaa | 60 |
| ttgtaattcc atgaaggaag gaagtggtgc aaaagatgaa gctaactatt cctgttttc | 120 |
| tttttaagag tctgcaattc ataatggagc tactgtactg gctattggaa ggaggagatt | 180 |
| ctgaagataa ggaggtaaaa cctgtttaga aattaaaaat gagttacgat ttaaagaaaa | 240 |
| ttcagatgac tcattgtgag tgctagttct cttgtaggat gccactggaa atgttgaaat | 300 |
| gaaaatatt cagccgttgg tctttgaaat ttcctgtgat gtgttcaat ctagatgcaa | 360 |
| agaacatgga aaatcaaag tgctcgagtg gtttaaatat gttttgggta ttcctgttta | 420 |

```
tagactataa tactttttcca attaaaatcc tcagttgtca cgcagaagaa ggttaagctg      480
tatttgattg ccagttttac tgaaaatgct tagtatttta cagtatcacc aaatatattt      540
tgtttagcca aggtatagga aaaataaaat aaattgtata ggttgacttt tttctaaaat      600
gtctttattg gattgaatga atgtttatac ctgaaaaaaa aaggttcaaa aaaa            654
```

<210> SEQ ID NO 25
<211> LENGTH: 732
<212> TYPE: DNA
<213> ORGANISM: Homo Sapiens

<400> SEQUENCE: 25

```
tctcggcgcc agaggggcgg ggaggggcgg ggtctcgatc gcgctattgt catggagacg       60
ggaagctggc tgcagcggcg gcggggaccg tggggccgag gtggctgcca gccggccaat      120
gtctaagcga ggcggagcgg cccaggcggc ccgagcctgg gggagcgcgc agccggccag      180
tggcggcctc gccggcggcc tcttcccggg ctcgcagtag gcccgagtcg tcgccgggag      240
ctcctgggag cagcgtcccc gccctgctcc cctcgctccc gcctcttgcg gccccacggc      300
ccctcagcgc ccgcccccgg ctccgcccgc cgcagccgca gcccctggcg ctaacggtcg      360
gtaacggccc gcgcgcgccg cccgccgggg gctcgcgcca gccacgaggg agcgtccgcg      420
gcccgcgcgc ccgcgcggcg gaggagaggt gttaagtgtg atgcttccat aatacatttg      480
gatgctgtca gctaagttca cttctgaact aagggggttcc tccaaatgtt ggctgaaatt      540
catcccaagg ctggtctgca agtgagtgtc tgcacacagt ttgcttgtat gtggagtcga      600
tccaaaatag catcaatgtt ggttttacca aagtatttat tattgataat agaggctaag      660
tacaaaatgt agagaatgtc agctacttga ggcctttgat tattaaaaat tttattaatg      720
cattaaacaa ga                                                         732
```

<210> SEQ ID NO 26
<211> LENGTH: 556
<212> TYPE: DNA
<213> ORGANISM: Homo Sapiens

<400> SEQUENCE: 26

```
gtgttaagtg tgatgcttcc ataatacatt tggatgctgt cagctaagtt cacttctgaa       60 ctaagggggtt cctccaaatg ttggctgaaa ttcatcccaa ggctggtctg caaagtctgc     120
aattcataat ggagctactg tactggctat tggaaggagg agattctgaa gataaggagg     180
atgccactgg aaatgttgaa atgaaaaata ttcagccgtt ggtctttgaa atttcctgtg     240
atgtgtttca atctagatgc aaagaacatg gaaaaatcaa agtgctcgag tggtttaaat     300
atgtttgggg tattcctgtt tatagactat aatacttttc caattaaaat cctcagttgt     360
cacgcagaag aaggttaagc tgtatttgat tgccagtttt actgaaaatg cttagtattt     420
tacagtatca ccaaatatat tttgtttagc caaggtatag gaaaaataaa ataaattgta     480
taggttgact tttttctaaa atgtctttat tggattgaat gaatgtttat acctgaaaaa     540
aaaaggttca aaaaaa                                                     556
```

<210> SEQ ID NO 27
<211> LENGTH: 1173
<212> TYPE: DNA
<213> ORGANISM: Homo Sapiens

<400> SEQUENCE: 27

| | |
|---|---:|
| tctcggcgcc agaggggcgg ggaggggcgg ggtctcgatc gcgctattgt catggagacg | 60 |
| ggaagctggc tgcagcggcg gcggggaccg tggggccgag gtggctgcca gccggccaat | 120 |
| gtctaagcga ggcggagcgg cccaggcggc ccgagcctgg gggagcgcgc agccggccag | 180 |
| tggcggcctc gccggcggcc tcttcccggg ctcgcagtag gcccgagtcg tcgccgggag | 240 |
| ctcctgggag cagcgtcccc gccctgctcc cctcgctccc gcctcttgcg gccccacggc | 300 |
| ccctcagcgc ccgcccccgg ctccgcccgc cgcagccgca gcccctggcg ctaacggtcg | 360 |
| gtaacggccc gcgcgcgccg cccgccgggg gctcgcgcca gccacgaggg agcgtccgcg | 420 |
| gcccgcgcgc ccgcgcggcg gaggagaggt gttaagtgtg atgcttccat aatacatttg | 480 |
| gatgctgtca gctaagttca cttctgaact aaggggttcc tccaaatgtt ggctgaaatt | 540 |
| catcccaagg ctggtctgca ttacctattt cttttaagaa taaatttagt gggaatatca | 600 |
| gttccagtca tgggtaccaa actttttag tgacagagta cacacagagt ctgcaattca | 660 |
| taatggagct actgtactgg ctattggaag gaggagattc tgaagataag gaggtaaaac | 720 |
| ctgtttagaa attaaaaatg agttacgatt taaagaaaat tcagatgact cattgtgagt | 780 |
| gctagttctc ttgtaggatg ccactggaaa tgttgaaatg aaaaatattc agccgttggt | 840 |
| cttttgaaatt tcctgtgatg tgtttcaatc tagatgcaaa gaacatggaa aaatcaaagt | 900 |
| gctcgagtgg tttaaatatg ttttgggtat tcctgtttat agactataat acttttccaa | 960 |
| ttaaaatcct cagttgtcac gcagaagaag gttaagctgt atttgattgc cagttttact | 1020 |
| gaaaatgctt agtattttac agtatcacca aatatatttt gtttagccaa ggtataggaa | 1080 |
| aaataaaata aattgtatag gttgactttt ttctaaaatg tctttattgg attgaatgaa | 1140 |
| tgtttatacc tgaaaaaaaa aggttcaaaa aaa | 1173 |

<210> SEQ ID NO 28
<211> LENGTH: 2229
<212> TYPE: DNA
<213> ORGANISM: Homo Sapiens

<400> SEQUENCE: 28

| | |
|---|---:|
| tgataagcaa catccaaata ttttgacccct gcttttagtg gttttttttca aatcttattt | 60 |
| tgagtcttac ttttagtcat agaatagcta ctgatttgat gcggtcttta actgacttaa | 120 |
| tattttttaca atttcaatat attttgcatt ggaatctcca gtaatgaata ttaaaatata | 180 |
| tgtacaatca tttgtagatg atatcaatta tattaagaca tttcagatgg gctattgtag | 240 |
| tatttaatgt gccgtatttt atggtagaat aattctcagt ctctggacat caagattgct | 300 |
| ttcagtggga atgaagatta atttacttca gtcctgattt tttaggcatc aatgcatgtt | 360 |
| ttcattttg tcagactttt accctctttt aatgtaattc tcaacttctt atggatttac | 420 |
| ttcccaatac ataaaatcct tcaaaacaag aatgataata atttttatac tttttataaa | 480 |
| aataaattta ttttttagtcc atcaaggtgt ctgaagattt tatgcctagg tatctccata | 540 |
| tctaacttga taaggaaaat aggataaaca atgctggtaa tagcaggaaa gtaagtattt | 600 |
| gaataagatg tcaaactgat atttcatgtg aacctaactc attttatggt aactaataat | 660 |
| tatcttattt aaatcaatag gtaaaacctg tttagaaatt aaaaatgagt tacgatttaa | 720 |
| agaaaattca gatgactcat tgtgagtgct agttctcttg taggatgcca ctggaaatgt | 780 |
| tgaaatgaaa aatgtaagta tatcttttgg tggaaaaaag gatagtctct aggacacaaa | 840 |
| attactgttt tatttttttc tcaggagttt gcctaagggt gtgacagatg atctctgtca | 900 |
| cttgtcttag ttgtgtcctg caataaactg gatgctttat aaaatactag acctgtgatt | 960 |

| | |
|---|---|
| tcgtatgctg taatatttca tttctccatc acccctccaa attatttctt agtttggagt | 1020 |
| aaaataataa atgtattata gtcaacatct cttgacccct ctttagtttc agctaaacta | 1080 |
| agcatgtgtg tttgtgtgtt cattttatag ttcatgtgta gaactatgtg aattaaattt | 1140 |
| aagaaacatg taaagtagag gaaatagttt tctggagaaa tttttccttt ttggatatta | 1200 |
| tgccctttc cattgctttt ctctgcttga aagcaaaaaa aagtacccta cccctgttct | 1260 |
| cctttaggga aaaactattc ctataaagta tttttaaatc gtgcaagtca ttgcctaggg | 1320 |
| ttagctaaaa catttctttt taaaaggag aaaatgccct ggctttaaca ttttcttgta | 1380 |
| tttgtatcta ttaagataaa cagtttactt tgatacagta cataccaatc tacttaattt | 1440 |
| tttttccagg attccttta ctatgtttgg tctgacctt tatgataact aatatggga | 1500 |
| acaaattagc atataattct attttccatg tgacctcaac cagttgcaga attgtaccac | 1560 |
| tactttaggg ggggcaattt gacagtttat gtagactata gcattaattg ttcccaaatg | 1620 |
| ttcagtgcat cctggctaat gtgttattga aggtgtttc acgtaagcag ttagaggaag | 1680 |
| cacttcaccc ctattactaa gttattaaaa tgcctcctaa aggtagcatt ttaaattagt | 1740 |
| atacataatt gattagtaat ttgtcttctc ccaagcataa aacagcatag cagagttaag | 1800 |
| tgtgaccagt gaagtataag atattaggga ttgatggtga caatgatcat agcaactaaa | 1860 |
| tggatttttt ttttcttta gattcagccg ttggtctttg aaatttcctg tgatgtgttt | 1920 |
| caatctagat gcaaagaaca tggaaaaatc aaagtgctcg agtggtttaa atatgttttg | 1980 |
| ggtattcctg tttatagact ataatacttt tccaattaaa atcctcagtt gtcacgcaga | 2040 |
| agaaggttaa gctgtatttg attgccagtt ttactgaaaa tgcttagtat tttacagtat | 2100 |
| caccaaatat attttgttta gccaaggtat aggaaaaata aaataaattg tataggttga | 2160 |
| cttttttcta aaatgtcttt attggattga atgaatgttt atacctgaaa aaaaaaggtt | 2220 |
| caaaaaaat | 2229 |

<210> SEQ ID NO 29
<211> LENGTH: 2097
<212> TYPE: DNA
<213> ORGANISM: Homo Sapiens

<400> SEQUENCE: 29

| | |
|---|---|
| tttaatagaa ggaaaatata aatttaatat ctgggcaatt gagacctta aacttacttt | 60 |
| aaaagtatga tcttgatgta tatgatactg ttttgtcttt gctatattaa cagaattaga | 120 |
| ggggtgttct gcaattcaaa taccttatat attccaaatt ttattctcta taatggactt | 180 |
| ttaaaataaa aggtatatgt gcttcaagag ggcaaaattt gaatcatgag ctaatttgct | 240 |
| aagcatcaga ttatagaaaa gcatccttga ttaaatttgga actgtgaaag ggggcgggta | 300 |
| aaactgtttt ctgcagaaat ttactagtgc agcaaccatt taaattaaat gtttgttaac | 360 |
| ataatagtga tggcattttc tcctccccct ccttgtggtt ttgtccaact agatgttaca | 420 |
| gtggcagttg cactgactgt taagtgttta aatgatgaca ccattatgtg aagtgatttt | 480 |
| gaaatgagag attccagcca agaattacat ctgctcccat ctccttcaaa tcatactctc | 540 |
| tggcagtaca gattatgatt gatttgtttg tgacagatt caggaaacag tcattgattt | 600 |
| ttcaatatttt taccttaaaa ttatttacag ttgtaaccat ggggaggtat tttcatgggc | 660 |
| tgtcagcccc tgaaagacta ggataatatt ccctgctctc tgacaagaca aattacctgt | 720 |
| aatgagtgca gtagctgaag ggtatacttt tattttaaaa tatgtcaata accccagtga | 780 |

| | |
|---|---|
| ctaaacgaat attgatttag cataatgaag cctgagtaac gtgaaaatga gcttttcaa | 840 |
| ggggcatggt aaagtctttc tttttagctg gttgtaagaa gcttttgatt cttttcagcc | 900 |
| agctggtagg aatatagaat tttataagca aaccatcagg aatgatagtg ttgtttctga | 960 |
| taagcaacat ccaaatattt tgaccctgct tttagtggtt tttttcaaat cttattttga | 1020 |
| gtcttacttt tagtcataga atagctactg atttgatgcg gtctttaact gacttaatat | 1080 |
| ttttacaatt tcaatatatt ttgcattgga atctccagta atgaatatta aaatatatgt | 1140 |
| acaatcattt gtagatgata tcaattatat taagacattt cagatgggct attgtagtat | 1200 |
| ttaatgtgcc gtattttatg gtagaataat tctcagtctc tggacatcaa gattgctttc | 1260 |
| agtgggaatg aagattaatt tacttcagtc ctgattttt aggcatcaat gcatgttttc | 1320 |
| attttgtca gacttttacc ctcttttaat gtaattctca acttcttatg gatttacttc | 1380 |
| ccaatacata aaatccttca aaacaagaat gataataatt tttatacttt ttataaaaat | 1440 |
| aaatttattt ttagtccatc aaggtgtctg aagattttat gcctaggtat ctccatatct | 1500 |
| aacttgataa ggaaaatagg ataaacaatg ctggtaatag caggaaagta agtatttgaa | 1560 |
| taagatgtca aactgatatt tcatgtgaac ctaactcatt ttatggtaac taataattat | 1620 |
| cttatttaaa tcaataggta aaacctgttt agaaattaaa aatgagttac gatttaaaga | 1680 |
| aaattcagat gactcattgt gagtgctagt tctcttgtag gatgccactg gaaatgttga | 1740 |
| aatgaaaaat attcagccgt tggtctttga aatttcctgt gatgtgtttc aatctagatg | 1800 |
| caaagaacat ggaaaaatca aagtgctcga gtggtttaaa tatgttttgg gtattcctgt | 1860 |
| ttatagacta aatacttttt ccaattaaaa tcctcagttg tcacgcagaa gaaggttaag | 1920 |
| ctgtatttga ttgccagttt tactgaaaat gcttagtatt ttacagtatc accaaatata | 1980 |
| ttttgtttag ccaaggtata ggaaaaataa aataaattgt ataggttgac ttttttctaa | 2040 |
| aatgtcttta ttggattgaa tgaatgttta tacctgaaaa aaaaaggttc aaaaaaa | 2097 |

<210> SEQ ID NO 30
<211> LENGTH: 1534
<212> TYPE: DNA
<213> ORGANISM: Homo Sapiens

<400> SEQUENCE: 30

| | |
|---|---|
| tctcggcgcc agaggggcgg ggaggggcgg ggtctcgatc gcgctattgt catggagacg | 60 |
| ggaagctggc tgcagcggcg gcggggaccg tggggccgag gtggctgcca gccggccaat | 120 |
| gtctaagcga ggcggagcgg cccaggcggc ccgagcctgg gggagcgcgc agccggccag | 180 |
| tggcggcctc gccggcggcc tcttcccggg ctcgcagtag gcccgagtcg tcgccgggag | 240 |
| ctcctgggag cagcgtcccc gccctgctcc cctcgctccc gctcttgcg gccccacggc | 300 |
| ccctcagcgc ccgcccccgg ctccgcccgc cgcagccgca gccctggcg ctaacggtcg | 360 |
| gtaacgcccc gcgcgcgccg cccgccgggg gctcgcgcca gccacgaggg agcgtccgcg | 420 |
| gcccgcgcgc ccgcgcggcg gaggagaggt gttaagtgtg atgcttccat aatacatttg | 480 |
| gatgctgtca gctaagttca cttctgaact aaggggttcc tccaaatgtt ggctgaaatt | 540 |
| catcccaagg ctggtctgca aagtctgcaa ttcataatgg agctactgta ctggctattg | 600 |
| gaaggaggag attctgaaga taaggaggta atattatctc ttttaaaaga atactttcct | 660 |
| ctgtaatcct gaatctttat tacatgtaag aactttgtgc agtagacagc aatttctttg | 720 |
| aatttggtat atggaaacaa ttttattttc ctctgctaag ttttgagcc tgcctcttct | 780 |
| agtgccatgg actgcattgg tagagctgag aaatatcatt tagccatact cagcacccTt | 840 |

```
aaaatagctt ctttctgaga attagatctg tgaaggtgtc ctgcacagtt cttgtagatg    900
tcattttagt ttgtggttga cgtgcatgca ttgcatcctg gctaatgtgt tattgaaggt    960
gttttcacgt aagcagttag aggaagcact tcacccctat tactaagtta ttaaaatgcc   1020
tcctaaaggt agcattttaa attagtatac ataattgatt agtaatttgt cttctcccaa   1080
gcataaaaca gcatagcaga gttaagtgtg accagtgaag tataagatat tagggattga   1140
tggtgacaat gatcatagca actaaatgga ttttttttt cttttagatt cagccgttgg   1200
tctttgaaat ttcctgtgat gtgtttcaat ctagatgcaa agaacatgga aaaatcaaag   1260
tgctcgagtg gtttaaatat gttttgggta ttcctgttta tagactataa tacttttcca   1320
attaaaatcc tcagttgtca cgcagaagaa ggttaagctg tatttgattg ccagttttac   1380
tgaaaatgct tagtatttta cagtatcacc aaatatattt tgtttagcca aggtatagga   1440
aaaataaaat aaattgtata ggttgacttt tttctaaaat gtctttattg gattgaatga   1500
atgtttatac ctgaaaaaaa aaggttcaaa aaaa                              1534
```

<210> SEQ ID NO 31
<211> LENGTH: 1087
<212> TYPE: DNA
<213> ORGANISM: Homo Sapiens

<400> SEQUENCE: 31

```
tctcggcgcc agaggggcgg ggaggggcgg ggtctcgatc gcgctattgt catggagacg     60
ggaagctggc tgcagcggcg gcgggaccg tggggccgag gtggctgcca gccggccaat    120
gtctaagcga ggcggagcgg cccaggcggc ccgagcctgg gggagcgcgc agccggccag    180
tggcggcctc gccggcggcc tcttcccggg ctcgcagtag gcccgagtcg tcgccgggag    240
ctcctgggag cagcgtcccc gccctgctcc cctcgctccc gcctcttgcg gccccacggc    300
ccctcagcgc ccgccccgg ctccgcccgc cgcagccgca gccctggcg ctaacggtcg      360 gtaacggccc gcgcgcgccg cccgccgggg gctcgcgcca gccacgaggg agcgtccgcg    420
gcccgcgcgc ccgcgcggcg gaggagaggt gttaagtgtg atgcttccat aatacatttg    480
gatgctgtca gctaagttca cttctgaact aaggggttcc tccaaatgtt ggctgaaatt    540
catcccaagg ctggtctgca aagtctgcaa ttcataatgg agctactgta ctggctattg    600
gaaggaggag attctgaaga taaggaggta aaacctgttt agaaattaaa atgagttac    660 gatttaaaga aaattcagat gactcattgt gagtgctagt tctcttgtag gatgccactg    720
gaaatgttga aatgaaaaat attcagccgt tggtctttga aatttcctgt gatgtgtttc    780
aatctagatg caaagaacat ggaaaaatca agtgctcga gtggtttaaa tatgttttgg    840
gtattcctgt ttatagacta taatactttt ccaattaaaa tcctcagttg tcacgcagaa    900
gaaggttaag ctgtatttga ttgccagttt tactgaaaat gcttagtatt ttacagtatc    960
accaaatata ttttgtttag ccaaggtata ggaaaaataa aataaattgt ataggttgac   1020 tttttctaa aatgtcttta ttggattgaa tgaatgttta tacctgaaaa aaaaaggttc   1080
aaaaaaa                                                            1087
```

<210> SEQ ID NO 32
<211> LENGTH: 249
<212> TYPE: DNA
<213> ORGANISM: Homo Sapiens

<400> SEQUENCE: 32

```
agccgttggt ctttgaaatt tcctgtgatg tgtttcaatc tagatgcaaa gaacatggaa      60
aaatcaaagt gctcgagtgg tttaaatatg ttttgggtat tcctgtttat agactataat     120
acttttccaa ttaaaatcct cagttgtcac gcagaagaag gttaagctgt atttgattgc     180
cagttttact gaaaatgctt agtattttac agtatcacca aatatatttt gtttagccaa     240
ggtatagga                                                             249
```

<210> SEQ ID NO 33
<211> LENGTH: 273
<212> TYPE: DNA
<213> ORGANISM: Homo Sapiens

<400> SEQUENCE: 33

```
tgctgtcagc taagttcact tctgaactaa ggggttcctc caaatgttgg ctgaaattca      60
tcccaaggct ggtctgcaaa gtctgcaatt cataatggag ctactgtact ggctattgga     120
aggaggagat tctgaagata aggaggtaaa acctgtttag aaattaaaaa tgagttacga     180
tttaaagaaa attcagatga ctcattgtga gtgctagttc tcttgtagga tgccactgga     240
aatgttgaaa tgaaaaatat tcagccgttg gtc                                  273
```

<210> SEQ ID NO 34
<211> LENGTH: 34
<212> TYPE: DNA
<213> ORGANISM: Artificial sequence
<220> FEATURE:
<223> OTHER INFORMATION: Synthetic

<400> SEQUENCE: 34

```
taactggaat tcatgttggc tgaaattcat ccca                                  34
```

<210> SEQ ID NO 35
<211> LENGTH: 56
<212> TYPE: DNA
<213> ORGANISM: Artificial sequence
<220> FEATURE:
<223> OTHER INFORMATION: Synthetic

<400> SEQUENCE: 35

```
cacgataagc ttttattata gtctataaac aggaataccc aaaacatatt taaacc          56
```

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36

```
acacggcttt ccggagtaga                                                  20
```

<210> SEQ ID NO 37
<211> LENGTH: 28
<212> TYPE: DNA
<213> ORGANISM: Artificial sequence
<220> FEATURE:
<223> OTHER INFORMATION: Synthetic

<400> SEQUENCE: 37

```
aacaggtttt acctccttat cttcagaa                                         28
```

<210> SEQ ID NO 38
<211> LENGTH: 222

-continued

<212> TYPE: DNA
<213> ORGANISM: Homo Sapiens

<400> SEQUENCE: 38
gacacggctt tccggagtag agcccttgga ggtgttaagt gtgatgcttc cataatacat    60
ttggatgctg tcagctaagt tcacttctga actaaggggt tcctccaaat gttggctgaa   120
attcatccca aggctggtct gcaaagtctg caattcataa tggagctact gtactggcta   180
ttggaaggag gagattctga agataaggag gtaaaacctg tt                      222

<210> SEQ ID NO 39
<211> LENGTH: 222
<212> TYPE: DNA
<213> ORGANISM: Homo Sapiens

<400> SEQUENCE: 39
gacacggctt tccggagtag agcccttgga ggtgttaagt gtgatgcttc cataatacat    60
ttggatgctg tcagctaagt tcacttctga actaaggggt tcctccaaat gttggctgaa   120
attcatccca aggctggtct gcaaagtctg caattcataa tggagctact gtactggcta   180
ttggaaggag gagattctga agataaggag gtaaaacctg tt                      222

<210> SEQ ID NO 40
<211> LENGTH: 20
<212> TYPE: DNA
<213> ORGANISM: Artificial sequence
<220> FEATURE:
<223> OTHER INFORMATION: Synthetic

<400> SEQUENCE: 40
acacggcttt ccggagtaga                                                20

<210> SEQ ID NO 41
<211> LENGTH: 26
<212> TYPE: DNA
<213> ORGANISM: Artificial sequence
<220> FEATURE:
<223> OTHER INFORMATION: Synthetic

<400> SEQUENCE: 41
ggcatcctac aagagaactc cttatc                                         26

<210> SEQ ID NO 42
<211> LENGTH: 226
<212> TYPE: DNA
<213> ORGANISM: Homo Sapiens

<400> SEQUENCE: 42
acacggcttt ccggagtaga gcccttggag gtgttaagtg tgatgcttcc ataatacatt    60
tggatgctgt cagctaagtt cacttctgaa ctaaggggtt cctccaaatg ttggctgaaa   120
ttcatcccaa ggctggtctg caaagtctgc aattcataat ggagctactg tactggctat   180
tggaaggagg agattctgaa gataaggagt tctcttgtag gatgcc                  226

<210> SEQ ID NO 43
<211> LENGTH: 226
<212> TYPE: DNA
<213> ORGANISM: Homo Sapiens

<400> SEQUENCE: 43
acacggcttt ccggagtaga gcccttggag gtgttaagtg tgatgcttcc ataatacatt    60

```
tggatgctgt cagctaagtt cacttctgaa ctaaggggtt cctccaaatg ttggctgaaa      120
ttcatcccaa ggctggtctg caaagtctgc aattcataat ggagctactg tactggctat      180
tggaaggagg agattctgaa gataaggagt tctcttgtag gatgcc                     226
```

```
<210> SEQ ID NO 44
<211> LENGTH: 25
<212> TYPE: DNA
<213> ORGANISM: Artificial sequence
<220> FEATURE:
<223> OTHER INFORMATION: Synthetic

<400> SEQUENCE: 44
gctgacagca tccaaatgta ttatg                                            25
```

```
<210> SEQ ID NO 45
<211> LENGTH: 29
<212> TYPE: DNA
<213> ORGANISM: Artificial sequence
<220> FEATURE:
<223> OTHER INFORMATION: Synthetic

<400> SEQUENCE: 45
tttttgagaa gtgtatcatc taggaagaa                                        29
```

```
<210> SEQ ID NO 46
<211> LENGTH: 27
<212> TYPE: DNA
<213> ORGANISM: Artificial sequence
<220> FEATURE:
<223> OTHER INFORMATION: Synthetic

<400> SEQUENCE: 46
acatatttaa accactcgag cactttg                                          27
```

```
<210> SEQ ID NO 47
<211> LENGTH: 398
<212> TYPE: DNA
<213> ORGANISM: Homo Sapiens

<400> SEQUENCE: 47
ctttttgaga agtgtatcat ctaggaagaa aatcaaatgg agtattggta attaaattgt      60
aattccatga aggaaggaag tggtgcaaaa gatgaagcta actattcctg ttttctttt      120 taagagtctg caattcataa tggagctact gtactggcta ttggaaggag gagattctga      180
agataaggag gtaaaacctg tttagaaatt aaaaatgagt tacgatttaa agaaaattca      240
gatgactcat tgtgagtgct agttctcttg taggatgcca ctggaaatgt tgaaatgaaa      300 atattcagc cgttggtctt tgaaatttcc tgtgatgtgt tcaatctag atgcaaagaa       360 catggaaaaa tcaaagtgct cgagtggttt aaatatgt                              398
```

```
<210> SEQ ID NO 48
<211> LENGTH: 398
<212> TYPE: DNA
<213> ORGANISM: Homo Sapiens

<400> SEQUENCE: 48
ctttttgaga agtgtatcat ctaggaagaa aatcaaatgg agtattggta attaaattgt      60
aattccatga aggaaggaag tggtgcaaaa gatgaagcta actattcctg ttttctttt      120 taagagtctg caattcataa tggagctact gtactggcta ttggaaggag gagattctga      180
agataaggag gtaaaacctg tttagaaatt aaaaatgagt tacgatttaa agaaaattca      240
```

```
gatgactcat tgtgagtgct agttctcttg taggatgcca ctggaaatgt tgaaatgaaa        300
aatattcagc cgttggtctt tgaaatttcc tgtgatgtgt ttcaatctag atgcaaagaa        360
catggaaaaa tcaaagtgct cgagtggttt aaatatgt                                398
```

```
<210> SEQ ID NO 49
<211> LENGTH: 22
<212> TYPE: DNA
<213> ORGANISM: Artificial sequence
<220> FEATURE:
<223> OTHER INFORMATION: Synthetic

<400> SEQUENCE: 49
ggatcgactc cacatacaag ca                                                 22

<210> SEQ ID NO 50
<211> LENGTH: 205
<212> TYPE: DNA
<213> ORGANISM: Homo Sapiens

<400> SEQUENCE: 50
cagccacgag ggagcgtccg cggcccgcgc gcccgcgcgg cggaggagag gtgttaagtg        60
tgatgcttcc ataatacatt tggatgctgt cagctaagtt cacttctgaa ctaaggggtt       120
cctccaaatg ttggctgaaa ttcatcccaa ggctggtctg caagtgagtg tctgcacaca       180
gtttgcttgt atgtggagtc gatcc                                             205

<210> SEQ ID NO 51
<211> LENGTH: 205
<212> TYPE: DNA
<213> ORGANISM: Homo Sapiens

<400> SEQUENCE: 51
cagccacgag ggagcgtccg cggcccgcgc gcccgcgcgg cggaggagag gtgttaagtg        60
tgatgcttcc ataatacatt tggatgctgt cagctaagtt cacttctgaa ctaaggggtt       120
cctccaaatg ttggctgaaa ttcatcccaa ggctggtctg caagtgagtg tctgcacaca       180
gtttgcttgt atgtggagtc gatcc                                             205

<210> SEQ ID NO 52
<211> LENGTH: 22
<212> TYPE: DNA
<213> ORGANISM: Artificial sequence
<220> FEATURE:
<223> OTHER INFORMATION: Synthetic

<400> SEQUENCE: 52
atgttggctg aaattcatcc ca                                                 22

<210> SEQ ID NO 53
<211> LENGTH: 22
<212> TYPE: DNA
<213> ORGANISM: Artificial sequence
<220> FEATURE:
<223> OTHER INFORMATION: Synthetic

<400> SEQUENCE: 53
ttccagtggc atcctcctta tc                                                 22

<210> SEQ ID NO 54
<211> LENGTH: 115
<212> TYPE: DNA
```

<213> ORGANISM: Homo Sapiens

<400> SEQUENCE: 54
atgttggctg aaattcatcc caaggctggt ctgcaaagtc tgcaattcat aatggagcta     60
ctgtactggc tattggaagg aggagattct gaagataagg aggatgccac tggaa         115

<210> SEQ ID NO 55
<211> LENGTH: 115
<212> TYPE: DNA
<213> ORGANISM: Homo Sapiens

<400> SEQUENCE: 55
atgttggctg aaattcatcc caaggctggt ctgcaaagtc tgcaattcat aatggagcta     60
ctgtactggc tattggaagg aggagattct gaagataagg aggatgccac tggaa         115

<210> SEQ ID NO 56
<211> LENGTH: 22
<212> TYPE: DNA
<213> ORGANISM: Artificial sequence
<220> FEATURE:
<223> OTHER INFORMATION: Synthetic

<400> SEQUENCE: 56
atgttggctg aaattcatcc ca                                              22

<210> SEQ ID NO 57
<211> LENGTH: 30
<212> TYPE: DNA
<213> ORGANISM: Artificial sequence
<220> FEATURE:
<223> OTHER INFORMATION: Synthetic

<400> SEQUENCE: 57
tctgtgtgta ctctgtcact aaaaagttt                                       30

<210> SEQ ID NO 58
<211> LENGTH: 124
<212> TYPE: DNA
<213> ORGANISM: Homo Sapiens

<400> SEQUENCE: 58
atgttggctg aaattcatcc caaggctggt ctgcaattac ctatttcttt taagaataaa     60
tttagtggga atatcagttc cagtcatggg taccaaactt ttttagtgac agagtacaca    120
caga                                                                 124

<210> SEQ ID NO 59
<211> LENGTH: 124
<212> TYPE: DNA
<213> ORGANISM: Homo Sapiens

<400> SEQUENCE: 59
atgttggctg aaattcatcc caaggctggt ctgcaattac ctatttcttt taagaataaa     60
tttagtggga atatcagttc cagtcatggg taccaaactt ttttagtgac agagtacaca    120
caga                                                                 124

<210> SEQ ID NO 60
<211> LENGTH: 27
<212> TYPE: DNA
<213> ORGANISM: Artificial sequence
<220> FEATURE:
<223> OTHER INFORMATION: Synthetic

```
<400> SEQUENCE: 60
taagatatta gggattgatg gtgacaa                                          27

<210> SEQ ID NO 61
<211> LENGTH: 27
<212> TYPE: DNA
<213> ORGANISM: Artificial sequence
<220> FEATURE:
<223> OTHER INFORMATION: Synthetic

<400> SEQUENCE: 61
acatatttaa accactcgag cactttg                                          27

<210> SEQ ID NO 62
<211> LENGTH: 160
<212> TYPE: DNA
<213> ORGANISM: Homo Sapiens

<400> SEQUENCE: 62
taagatatta gggattgatg gtgacaatga tcatagcaac taaatggatt ttttttttct      60
tttagattca gccgttggtc tttgaaattt cctgtgatgt gtttcaatct agatgcaaag     120
aacatggaaa aatcaaagtg ctcgagtggt ttaaatatgt                           160

<210> SEQ ID NO 63
<211> LENGTH: 159
<212> TYPE: DNA
<213> ORGANISM: Homo Sapiens

<400> SEQUENCE: 63
taagatatta gggattgatg gtgacaatga tcatagcaac taaatggatt tttttttctt      60
ttagattcag ccgttggtct tgaaatttc ctgtgatgtg tttcaatcta gatgcaaaga     120
acatggaaaa atcaaagtgc tcgagtggtt taaatatgt                            159

<210> SEQ ID NO 64
<211> LENGTH: 28
<212> TYPE: DNA
<213> ORGANISM: Artificial sequence
<220> FEATURE:
<223> OTHER INFORMATION: Synthetic

<400> SEQUENCE: 64
tgcctaggta tctccatatc taacttga                                         28

<210> SEQ ID NO 65
<211> LENGTH: 27
<212> TYPE: DNA
<213> ORGANISM: Artificial sequence
<220> FEATURE:
<223> OTHER INFORMATION: Synthetic

<400> SEQUENCE: 65
acatatttaa accactcgag cactttg                                          27

<210> SEQ ID NO 66
<211> LENGTH: 306
<212> TYPE: DNA
<213> ORGANISM: Homo Sapiens

<400> SEQUENCE: 66
tgcctaggta tctccatatc taacttgata aggaaaatag gataaacaat gctggtaata      60
```

```
tttatggtaa ctaataatta tcttatttaa atcaataggt aaaacctgtt tagaaattaa     120
aaatgagtta cgatttaaag aaaattcaga tgactcattg tgagtgctag ttctcttgta     180
ggatgccact ggaaatgttg aaatgaaaaa tattcagccg ttggtctttg aaatttcctg     240
tgatgtgttt caatctagat gcaaagaaca tggaaaaatc aaagtgctcg agtggtttaa     300
atatgt                                                                306
```

<210> SEQ ID NO 67
<211> LENGTH: 366
<212> TYPE: DNA
<213> ORGANISM: Homo Sapiens

<400> SEQUENCE: 67

```
tgcctaggta tctccatatc taacttgata aggaaaatag ataaacaat gctggtaata      60 gcaggaaagt aagtatttga ataagatgtc aaactgatat tcatgtgaa cctaactcat     120 tttatggtaa ctaataatta tcttatttaa atcaataggt aaaacctgtt tagaaattaa     180
aaatgagtta cgatttaaag aaaattcaga tgactcattg tgagtgctag ttctcttgta     240
ggatgccact ggaaatgttg aaatgaaaaa tattcagccg ttggtctttg aaatttcctg     300
tgatgtgttt caatctagat gcaaagaaca tggaaaaatc aaagtgctcg agtggtttaa     360
atatgt                                                                366
```

<210> SEQ ID NO 68
<211> LENGTH: 22
<212> TYPE: DNA
<213> ORGANISM: Artificial sequence
<220> FEATURE:
<223> OTHER INFORMATION: Synthetic

<400> SEQUENCE: 68

```
atgttggctg aaattcatcc ca                                               22
```

<210> SEQ ID NO 69
<211> LENGTH: 28
<212> TYPE: DNA
<213> ORGANISM: Artificial sequence
<220> FEATURE:
<223> OTHER INFORMATION: Synthetic

<400> SEQUENCE: 69

```
tgctgagtat ggctaaatga tatttctc                                         28
```

<210> SEQ ID NO 70
<211> LENGTH: 310
<212> TYPE: DNA
<213> ORGANISM: Homo Sapiens

<400> SEQUENCE: 70

```
atgttggctg aaattcatcc caaggctggt ctgcaaagtc tgcaattcat aatggagcta      60
ctgtactggc tattggaagg aggagattct gaagataagg aggtaatatt atctctttta     120
aaagaatact ttcctctgta atcctgaatc tttattacat gtaagaactt tgtgcagtag     180
acagcaattt ctttgaattt ggtatatgga acaattttta ttttcctctg ctaagttttt     240
gagcctgcct cttctagtgc catggactgc attggtagag ctgagaaata tcatttagcc     300
atactcagca                                                            310
```

<210> SEQ ID NO 71
<211> LENGTH: 310

<212> TYPE: DNA
<213> ORGANISM: Homo Sapiens

<400> SEQUENCE: 71

```
atgttggctg aaattcatcc caaggctggt ctgcaaagtc tgcaattcat aatggagcta      60
ctgtactggc tattggaagg aggagattct gaagataagg aggtaatatt atctctttta     120
aaagaatact ttcctctgta atcctgaatc tttattacat gtaagaactt tgtgcagtag     180
acagcaattt ctttgaattt ggtatatgga aacaatttta ttttcctctg ctaagttttt     240
gagcctgcct cttctagtgc catggactgc attggtagag ctgagaaata tcatttagcc     300
atactcagca                                                             310
```

<210> SEQ ID NO 72
<211> LENGTH: 17
<212> TYPE: DNA
<213> ORGANISM: Artificial sequence
<220> FEATURE:
<223> OTHER INFORMATION: Synthetic

<400> SEQUENCE: 72

```
cagccacgag ggagcgt                                                      17
```

<210> SEQ ID NO 73
<211> LENGTH: 28
<212> TYPE: DNA
<213> ORGANISM: Artificial sequence
<220> FEATURE:
<223> OTHER INFORMATION: Synthetic

<400> SEQUENCE: 73

```
aacaggtttt acctccttat cttcagaa                                          28
```

<210> SEQ ID NO 74
<211> LENGTH: 240
<212> TYPE: DNA
<213> ORGANISM: Homo Sapiens

<400> SEQUENCE: 74

```
agccacgagg gagcgtccgc ggcccgcgcg cccgcgcggc ggaggagagg tgttaagtgt      60
gatgcttcca taatacattt ggatgctgtc agctaagttc acttctgaac taagggttc     120
ctccaaatgt tggctgaaat tcatcccaag gctggtctgc aaagtctgca attcataatg    180
gagctactgt actggctatt ggaaggagga gattctgaag ataaggaggt aaaacctgtt    240
```

<210> SEQ ID NO 75
<211> LENGTH: 240
<212> TYPE: DNA
<213> ORGANISM: Homo Sapiens

<400> SEQUENCE: 75

```
agccacgagg gagcgtccgc ggcccgcgcg cccgcgcggc ggaggagagg tgttaagtgt      60
gatgcttcca taatacattt ggatgctgtc agctaagttc acttctgaac taagggttc     120
ctccaaatgt tggctgaaat tcatcccaag gctggtctgc aaagtctgca attcataatg    180
gagctactgt actggctatt ggaaggagga gattctgaag ataaggaggt aaaacctgtt    240
```

<210> SEQ ID NO 76
<211> LENGTH: 40
<212> TYPE: DNA
<213> ORGANISM: Homo Sapiens

<400> SEQUENCE: 76

```
taaaatgtct ttattggatt gaatgaatgt ttatacctga                                40
```

<210> SEQ ID NO 77
<211> LENGTH: 68
<212> TYPE: DNA
<213> ORGANISM: Homo Sapiens

<400> SEQUENCE: 77

```
aggttaagct gtatttgatt gccagtttta ctgaaaatgc ttagtatttt acagtatcac        60
caaatata                                                                   68
```

<210> SEQ ID NO 78
<211> LENGTH: 140
<212> TYPE: DNA
<213> ORGANISM: Homo Sapiens

<400> SEQUENCE: 78

```
aaatttcctg tgatgtgttt caatctagat gcaaagaaca tggaaaaatc aaagtgctcg        60
agtggtttaa atatgttttg ggtattcctg tttatagact ataatacttt tccaattaaa       120
atcctcagtt gtcacgcaga                                                    140
```

<210> SEQ ID NO 79
<211> LENGTH: 816
<212> TYPE: DNA
<213> ORGANISM: Homo Sapiens

<400> SEQUENCE: 79

```
gcctaagggt gtgacagatg atctctgtca cttgtcttag ttgtgtcctg caataaactg        60
gatgctttat aaaatactag acctgtgatt tcgtatgctg taatatttca tttctccatc       120
acccctccaa attatttctt agtttggagt aaaataataa atgtattata gtcaacatct       180
cttgacccct ctttagtttc agctaaacta agcatgtgtg tttgtgtgtt cattttatag       240
ttcatgtgta gaactatgtg aattaaattt aagaaacatg taaagtagag gaaatagttt       300
tctggagaaa ttttttcctt ttggatatta tgccctttc cattgctttt ctctgcttga       360
aagcaaaaaa aagtacccta cccctgttct cctttaggga aaaactattc ctataaagta       420
tttttaaatc gtgcaagtca ttgcctaggg ttagctaaaa catttctttt taaaaggag        480 aaaatgccct ggctttaaca ttttcttgta tttgtatcta ttaagataaa cagtttactt       540
tgatacagta cataccaatc tacttaattt ttttttccagg attccttta ctatgtttgg      600 tctgaccttt tatgataact taatatggga acaaattagc atataattct attttccatg       660
tgacctcaac cagttgcaga attgtaccac tactttaggg ggggcaattt gacagtttat       720
gtagactata gcattaattg ttcccaaatg ttcagtgcat cctggctaat gtgttattga       780
aggtgttttc acgtaagcag ttagaggaag cacttc                                  816
```

<210> SEQ ID NO 80
<211> LENGTH: 30
<212> TYPE: DNA
<213> ORGANISM: Homo Sapiens

<400> SEQUENCE: 80

```
gatgccactg gaaatgttga aatgaaaaat                                          30
```

<210> SEQ ID NO 81
<211> LENGTH: 34

<212> TYPE: DNA
<213> ORGANISM: Homo Sapiens

<400> SEQUENCE: 81
gaaaattcag atgactcatt gtgagtgcta gttc 34

<210> SEQ ID NO 82
<211> LENGTH: 635
<212> TYPE: DNA
<213> ORGANISM: Homo Sapiens

<400> SEQUENCE: 82 ttcaagggc atggtaaagt cttcttttt agctggttgt aagaagcttt tgattctttt 60
cagccagctg gtaggaatat agaattttat aagcaaacca tcaggaatga tagtgttgtt 120
tctgataagc aacatccaaa tatttgacc ctgcttttag tggttttttt caaatcttat 180
tttgagtctt acttttagtc atagaatagc tactgatttg atgcggtctt taactgactt 240
aatattttta caattcaat atattttgca ttggaatctc cagtaatgaa attaaaaata 300
tatgtacaat catttgtaga tgatatcaat tatattaaga catttcagat gggctattgt 360
agtatttaat gtgccgtatt ttatggtaga ataattctca gtctctggac atcaagattg 420
ctttcagtgg gaatgaagat taatttactt cagtcctgat tttttaggca tcaatgcatg 480
ttttcatttt tgtcagactt ttaccctctt ttaatgtaat tctcaacttc ttatggattt 540
acttcccaat acataaatc cttcaaaaca agaatgataa taattttat actttttata 600
aaaataaatt tatttttagt ccatcaaggt gtctg 635

<210> SEQ ID NO 83
<211> LENGTH: 36
<212> TYPE: DNA
<213> ORGANISM: Homo Sapiens

<400> SEQUENCE: 83
gcaattcata atggagctac tgtactggct attgga 36

<210> SEQ ID NO 84
<211> LENGTH: 104
<212> TYPE: DNA
<213> ORGANISM: Homo Sapiens

<400> SEQUENCE: 84
gtgtgatgct tccataatac atttggatgc tgtcagctaa gttcacttct gaactaaggg 60
gttcctccaa atgttggctg aaattcatcc caaggctggt ctgc 104

<210> SEQ ID NO 85
<211> LENGTH: 177
<212> TYPE: DNA
<213> ORGANISM: Homo Sapiens

<400> SEQUENCE: 85
ccgaccagac gtcccgtggg ctagggcctg ggcctcgggc cgcgtcggcg ccggtcgagc 60
ctctccgggt gtcggggttc ggggcgggcg cgcgtgggcg tggctcctct gtccacgcct 120
gttcccttcg tcgccgcggc tctcgtccgg gacacggctt tccggagtag agcccctt 177

<210> SEQ ID NO 86
<211> LENGTH: 318
<212> TYPE: DNA
<213> ORGANISM: Homo Sapiens

```
<400> SEQUENCE: 86
aggtggctgc cagccggcca atgtctaagc gaggcggagc ggcccaggcg gcccgagcct      60
gggggagcgc gcagccggcc agtggcggcc tcgccggcgg cctcttcccg ggctcgcagt     120
aggcccgagt cgtcgccggg agctcctggg agcagcgtcc ccgccctgct ccccctcgctc    180 ccgcctcttg cggccccacg gcccctcagc gcccgccccc ggctccgccc gccgcagccg     240
cagcccctgg cgctaacggt cggtaacggc ccgcgcgcgc cgcccgccgg gggctcgcgc     300
cagccacgag ggagcgtc                                                    318

<210> SEQ ID NO 87
<211> LENGTH: 94
<212> TYPE: DNA
<213> ORGANISM: Homo Sapiens

<400> SEQUENCE: 87
ggcctgagcg gttcagacta cattctccga gagcccctgg gtccgcccag cccagtgcct     60
gacacctcct tcacctatga ttgggcgctg gcct                                  94

<210> SEQ ID NO 88
<211> LENGTH: 276
<212> TYPE: DNA
<213> ORGANISM: Homo Sapiens

<400> SEQUENCE: 88
gtatagcaca gcatcacaac ctggatactg acattgatgc agtcaagaca gagaacattt     60
atatcatgag gaggatccct cattaccgcc ctttgatatc caccctact tccagaccat      120 ctcactcctc ccttaaccct ggcaaccact agcatgttct ccatttctat aaatttgcct    180
ttataggaat gttatataat tgcaattaaa gtgtgtaacc ttttgggt tgactcaccc      240 ggcatcattt tctggagatt cagcttatat gtgtca                               276

<210> SEQ ID NO 89
<211> LENGTH: 34
<212> TYPE: DNA
<213> ORGANISM: Artificial sequence
<220> FEATURE:
<223> OTHER INFORMATION: Synthetic

<400> SEQUENCE: 89
taactggaat tcatgttggc tgaaattcat ccca                                  34

<210> SEQ ID NO 90
<211> LENGTH: 56
<212> TYPE: DNA
<213> ORGANISM: Artificial sequence
<220> FEATURE:
<223> OTHER INFORMATION: Synthetic

<400> SEQUENCE: 90
cacgataagc ttttattata gtctataaac aggaataccc aaaacatatt taaacc         56

<210> SEQ ID NO 91
<211> LENGTH: 34
<212> TYPE: DNA
<213> ORGANISM: Artificial sequence
<220> FEATURE:
<223> OTHER INFORMATION: Synthetic

<400> SEQUENCE: 91
taactggaat tcatgttggc tgaaattcat ccca                                  34
```

<210> SEQ ID NO 92
<211> LENGTH: 56
<212> TYPE: DNA
<213> ORGANISM: Artificial sequence
<220> FEATURE:
<223> OTHER INFORMATION: Synthetic

<400> SEQUENCE: 92
cacgataagc ttttattata gtctataaac aggaataccc aaaacatatt taaacc                    56

<210> SEQ ID NO 93
<211> LENGTH: 20
<212> TYPE: DNA
<213> ORGANISM: Artificial sequence
<220> FEATURE:
<223> OTHER INFORMATION: Synthetic

<400> SEQUENCE: 93
acacggcttt ccggagtaga                                                            20

<210> SEQ ID NO 94
<211> LENGTH: 28
<212> TYPE: DNA
<213> ORGANISM: Artificial sequence
<220> FEATURE:
<223> OTHER INFORMATION: Synthetic

<400> SEQUENCE: 94
aacaggtttt acctccttat cttcagaa                                                   28

<210> SEQ ID NO 95
<211> LENGTH: 18
<212> TYPE: DNA
<213> ORGANISM: Artificial sequence
<220> FEATURE:
<223> OTHER INFORMATION: Synthetic

<400> SEQUENCE: 95
ggcggaggag aggtgagc                                                              18

<210> SEQ ID NO 96
<211> LENGTH: 25
<212> TYPE: DNA
<213> ORGANISM: Artificial sequence
<220> FEATURE:
<223> OTHER INFORMATION: Synthetic

<400> SEQUENCE: 96
gctgacagca tccaaatgta ttatg                                                      25

<210> SEQ ID NO 97
<211> LENGTH: 18
<212> TYPE: DNA
<213> ORGANISM: Artificial sequence
<220> FEATURE:
<223> OTHER INFORMATION: Synthetic

<400> SEQUENCE: 97
ggcggaggag aggtgagc                                                              18

<210> SEQ ID NO 98
<211> LENGTH: 17
<212> TYPE: DNA
<213> ORGANISM: Artificial sequence
<220> FEATURE:

-continued

<223> OTHER INFORMATION: Synthetic

<400> SEQUENCE: 98
cagccacgag ggagcgt                                                    17